US008449868B2

(12) United States Patent
Jennings et al.

(10) Patent No.: US 8,449,868 B2
(45) Date of Patent: May 28, 2013

(54) PREPARATION OF CATIONIC NANOPARTICLES AND PERSONAL CARE COMPOSITIONS COMPRISING SAID NANOPARTICLES

(75) Inventors: John Jennings, Moycullen (IE); Dietmar Hüglin, Weil am Rhein (DE); Jianwen Mao, New Milford, CT (US); Andreas Mühlebach, Frick (CH)

(73) Assignee: BASF SE, Ludwigshafen (DE)

( * ) Notice: Subject to any disclaimer, the term of this patent is extended or adjusted under 35 U.S.C. 154(b) by 907 days.

(21) Appl. No.: 12/378,567

(22) Filed: Feb. 17, 2009

(65) Prior Publication Data
US 2009/0214447 A1 Aug. 27, 2009

Related U.S. Application Data
(60) Provisional application No. 61/066,599, filed on Feb. 21, 2008.

(51) Int. Cl.
*A61K 8/02* (2006.01)
*A61Q 19/00* (2006.01)
*A61Q 5/00* (2006.01)
*A61Q 11/00* (2006.01)
*A61Q 15/00* (2006.01)
*A61Q 9/02* (2006.01)
*A61Q 5/02* (2006.01)
*A61Q 5/04* (2006.01)
*A61Q 5/10* (2006.01)
*A61Q 5/08* (2006.01)
*A61Q 3/02* (2006.01)
*A61Q 1/06* (2006.01)
*A61Q 1/10* (2006.01)
*A61Q 17/04* (2006.01)
*A01N 25/00* (2006.01)
*A01P 1/00* (2006.01)

(52) U.S. Cl.
USPC ............. 424/49; 514/772; 514/769; 514/770; 514/785; 510/130; 510/141; 510/119; 424/70.1; 424/65; 424/73; 424/70.2; 424/62; 424/61; 424/64; 424/63; 424/70.7; 424/59

(58) Field of Classification Search
USPC .......................................................... 424/49
See application file for complete search history.

(56) References Cited

U.S. PATENT DOCUMENTS

| | | | |
|---|---|---|---|
| 5,354,564 A | 10/1994 | Borish et al. ................. 424/490 |
| 6,447,764 B1 | 9/2002 | Bayer et al. | |
| 6,548,121 B1 | 4/2003 | Bauer et al. ................... 427/509 |
| 6,663,952 B1 | 12/2003 | Mehnert et al. ............... 428/327 |
| 7,494,502 B2 * | 2/2009 | Cumbie ........................... 607/88 |
| 2002/0128336 A1 | 9/2002 | Kolb et al. ..................... 521/50 |
| 2003/0095943 A1 | 5/2003 | Barbuzzi et al. | |
| 2003/0203009 A1 | 10/2003 | MacDonald ................... 424/443 |
| 2003/0235685 A1 | 12/2003 | Lofton et al. ................. 428/327 |
| 2004/0010864 A1 | 1/2004 | Vic et al. ............................ 8/405 |
| 2004/0033270 A1 | 2/2004 | Kropf et al. .................... 424/642 |
| 2004/0067208 A1* | 4/2004 | Lennon et al. .................. 424/59 |
| 2004/0127580 A1* | 7/2004 | Baran, Jr. ........................ 516/22 |
| 2004/0171515 A1 | 9/2004 | Hamers et al. ................ 510/504 |
| 2004/0237833 A1 | 12/2004 | Sepeur et al. ................. 427/521 |
| 2004/0247690 A1 | 12/2004 | Yang | |
| 2004/0250354 A1 | 12/2004 | Hamers et al. ..................... 8/137 |
| 2005/0084438 A1 | 4/2005 | Do et al. ................... 423/244.02 |
| 2005/0085144 A1 | 4/2005 | MacDonald et al. ........... 422/59 |
| 2005/0234416 A1 | 10/2005 | Kropf et al. .................... 604/367 |
| 2006/0160715 A1 | 7/2006 | Barraza et al. ................ 510/276 |
| 2006/0210726 A1 | 9/2006 | Jones et al. .................... 428/1.1 |
| 2006/0263898 A1 | 11/2006 | Paget et al. .................... 436/166 |
| 2006/0269441 A1 | 11/2006 | Ochomogo et al. ............. 422/28 |
| 2007/0049678 A1 | 3/2007 | Kim et al. ...................... 524/430 |
| 2007/0155882 A1 | 7/2007 | Yamaguchi et al. ........... 524/409 |
| 2007/0207052 A1 | 9/2007 | Quellet et al. | |
| 2008/0090019 A1 | 4/2008 | Sepeur et al. ................. 427/521 |
| 2008/0260851 A1 | 10/2008 | Somasundaran et al. ..... 424/501 |
| 2008/0268035 A1 | 10/2008 | Kim et al. | |
| 2008/0280138 A1 | 11/2008 | Currie et al. .................. 428/402 |
| 2009/0053448 A1 | 2/2009 | Paiva et al. ................... 428/41.3 |
| 2010/0178512 A1 | 7/2010 | Giesenberg et al. | |

FOREIGN PATENT DOCUMENTS

| | | | |
|---|---|---|---|
| EP | 1146057 | 10/2001 | |
| EP | 1005477 | 6/2002 | |
| SU | 1643558 | 4/1991 | |
| WO | 00/22039 | 4/2000 | |
| WO | 00/24527 | 5/2000 | |
| WO | 02087523 | 7/2002 | |
| WO | 02/062881 | 8/2002 | |
| WO | WO03/002652 A1 * | 1/2003 | ................... 428/32.1 |
| WO | 03/048258 | 6/2003 | |
| WO | 03055588 | 10/2003 | |
| WO | 2004041991 | 5/2004 | |
| WO | 2004/090053 | 10/2004 | |
| WO | 2006/007286 | 1/2006 | |

(Continued)

OTHER PUBLICATIONS

Harald Suhr, Plasma Chemistry and Plasma Processing, vol. 3, No. 1, 1983.

(Continued)

*Primary Examiner* — Fereydoun G Sajjadi
*Assistant Examiner* — Audrea Buckley
(74) *Attorney, Agent, or Firm* — Shiela A. Loggins

(57) ABSTRACT

The present invention is directed to cationic nanoparticles, methods to make them, and the use of compositions containing said nanoparticles in personal care compositions or formulations. The nanoparticles are useful in personal care applications and impart antimicrobial properties to home and personal care products containing them. These cationic nanoparticles also contribute useful conditioning properties to hair-care and skin-care products.

30 Claims, No Drawings

FOREIGN PATENT DOCUMENTS

| | | |
|---|---|---|
| WO | 2006/016800 | 2/2006 |
| WO | 2006/044375 | 4/2006 |
| WO | 2006/052285 | 5/2006 |
| WO | 2007046632 | 4/2007 |
| WO | WO2007/048722 A2 * | 5/2007 ..................... 424/49 |
| WO | 2008068154 | 6/2008 |

OTHER PUBLICATIONS

J.F. Friedrich, et al. Surface and Coatings Technology, 59 (1993) 371-378.

* cited by examiner

PREPARATION OF CATIONIC NANOPARTICLES AND PERSONAL CARE COMPOSITIONS COMPRISING SAID NANOPARTICLES

This application takes the benefit of U.S. Provisional Application No. 61/066,599, filed Feb. 21, 2008, herein incorporated entirely by reference.

BACKGROUND OF THE INVENTION

The present invention relates to cationic nanoparticles and personal care compositions comprising said cationic nanoparticles. The present invention also relates to methods for using such cationic nanoparticles to treat various substrates and surfaces; for example, hair, skin, etc.

The treatment of substrates with nanoparticles is described, for example, in WO04/090053 (antistatic laminate) and WO06/016800 (hydrophilic coating), where compositions of nanoparticles together with additional monomers and additional photoinitiators are applied on the substrates, and then the so coated surfaces of the substrates are hardened to graft the nanoparticles on the substrates.

The production of low-temperature plasmas and the plasma-assisted deposition of thin organic or inorganic layers, both under vacuum conditions and under normal pressure, have been known for some time. Fundamental principles and applications are described, for example, by H. Suhr, Plasma Chem. Plasma Process 3(1), 1, (1983). Plastics surfaces can be subjected to a plasma treatment and, as a result, a certain finish subsequently applied exhibits improved adhesion to the plastics substrate especially after low pressure treatment (see J. Friedrich et al., Surf. Coat. Technol. 59, 371 (1993)).

WO 00/24527 describes the plasma treatment of substrates with immediate vapour-deposition and grafting-on of photoinitiators in vacuo.

WO03/048258 and WO06/044375 each describe the application of methacryloyloxypropyl-modified silica particles in combination with a photoinitiator to a pre-treated plastics surface with irradiation drying. WO00/22039 teaches the curing of mixtures containing silica-nanoparticles, modifying agent and certain oligomers by electron beam or, in combination with a photoinitiator, by UV radiation.

US 2003/0235685 discloses polymeric nanoparticles in aqueous adhesives formulations, herein incorporated by reference in its entirety.

US 2004/0250354 discloses methods for treating surfaces of textile and non-textile with hydrophilic nanoparticles based on uncrosslinked polymers, herein incorporated by reference in its entirety.

US 2005/0085144 discloses coatings of nanoparticles containing metal ions having good gas absorbing properties, herein incorporated by reference in its entirety.

US 2004/0033270 discloses hygiene products containing nanosized zinc oxide particles, herein incorporated by reference in its entirety.

Copending application PCT/EP 2007/062800, filed Nov. 26, 2007, discloses a process for the surface modification of substrates with functionalized nanoparticles.

US 2004/0010864 discloses a method for treating human keratin fibers with metallic particles coated with organosulfur compounds, herein incorporated by reference in its entirety.

US 2003/0203009 discloses nanoparticles modified with metal ions for odor removal, herein incorporated by reference in its entirety.

US 2005/0084438 discloses a method for reducing odor using metal-modified silica particles, herein incorporated by reference in its entirety.

US 2004/0171515 discloses methods for treating surfaces of textile and non-textile with hydrophilic nanoparticles based on crosslinked polymers, herein incorporated by reference in its entirety.

U.S. Pat. No. 5,354,564 discloses personal care compositions of silicone particles wherein said particles have a surface modifier adsorbed onto the particle surface, herein incorporated by reference in its entirety.

US 2005/0234416 discloses hygiene products containing nanosized zinc oxide particles, herein incorporated by reference in its entirety.

US 2006/0160715 discloses laundry treatment compositions comprising organic/inorganic nanoparticles, herein incorporated by reference in its entirety.

WO 2006/052285 discloses polymeric nanoparticles for extraction and release of compounds.

US 2007/0049678 discloses thermoplastic nanocomposites comprising rubber-modified graft copolymer and metal oxide nanoparticles, herein incorporated by reference in its entirety.

WO 2002/062881 discloses foaming compositions for pressure-sensitive adhesives comprising nanoparticles.

WO 2006/007286 discloses polymerizable compositions comprising nanoparticles.

US 2006/0269441 discloses nanoparticle silica Pickering emulsions, herein incorporated by reference in its entirety.

US 2006/0263898 discloses nanoparticles bound to pro-perfume or pro-drug moieties, herein incorporated by reference in its entirety.

Accordingly, there is still a need for cationic nanoparticles that provide excellent conditioning properties in personal care products. The cationic nanoparticles of this present invention provide the extra conditioning benefits required in a personal care product. These cationic nanoparticles also contribute useful antimicrobial properties to personal care products and compositions.

SUMMARY OF THE INVENTION

The present invention is directed to personal care compositions comprising cationic nanoparticles, methods to make them, and the use of compositions containing said cationic nanoparticles in personal care products. The cationic nanoparticles are useful in personal care applications. The cationic nanoparticles of this present invention provide the extra conditioning benefits required in a personal care product. These cationic nanoparticles also contribute useful conditioning properties to hair-care and skin-care products.

The cationic nanoparticles of the instant invention also contribute useful antimicrobial properties to personal care products and compositions containing said cationic nanoparticles.

Another embodiment of the instant invention is a method for the conditioning treatment of mammalian keratin-containing fibers, wherein said method comprises contacting said fibers with an effective amount of a personal care composition or formulation comprising one or more cationic nanoparticles of formula (I).

Another embodiment of the instant invention is a method for the conditioning treatment of mammalian skin, wherein said method comprises contacting said skin with an effective amount of a personal care composition or formulation comprising one or more cationic nanoparticles of formula (I).

DETAILED DESCRIPTION OF THE INVENTION

The present invention provides a personal care composition comprising:
(a) an effective amount of at least one cationic nanoparticle of formula (I)
wherein

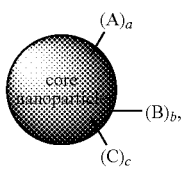

(I)

said cationic nanoparticle core comprises an inorganic or organic material and where
A is an organic substituent covalently bound to the core nanoparticle surface and containing at least one cationic group L;
B is an organic substituent covalently bound to the core nanoparticle surface and containing at least one cationic moiety G;
C is an organic substituent covalently bound to the core nanoparticle surface containing at least one functional group Z;
a is a number from 1 to $n_a$;
b is a number from 0 to $n_b$;
c is a number from 0 to $n_c$;
where the sum of $n_a+n_b+n_c$ is a number from 1 up to $n_t$, where $n_t$ is limited by the geometry and surface area of the core nanoparticle and the steric requirements of the respective substituents A, B, C; and
(b) a cosmetically acceptable adjuvant.

Another embodiment of the instant invention is a personal care composition comprising cationic nanoparticles of formula (I) wherein the organic substituent covalently bound to the core nanoparticle surface is

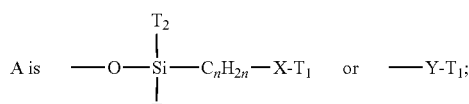

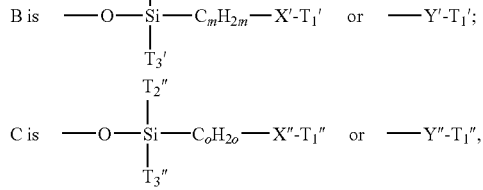

where

X, Y, X', Y', X" and Y", and n, m, o, $T_1$, $T_1'$, $T_1''$, $T_2$, $T_2'$, $T_2''$, $T_3$, $T_3'$, $T_3''$ are as defined below.

Another embodiment of the instant invention is a personal care composition comprising a cationic nanoparticle of formula (I) wherein said cationic nanoparticle core of formula (I) comprises an inorganic material wherein the organic substituent covalently bound to the core nanoparticle surface is A, B, and/or C wherein

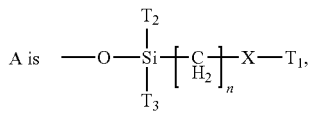

A is

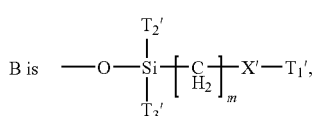

B is

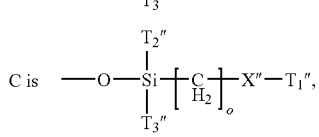

C is

X, X' and X" are independently of one another —O—, —S—, —$NR_1$—, —$NR_{101}$—, —OCO—, —SCO—, —$NR_1$CO—, —OCOO—, —OCO$NR_1$—, —$NR_1$COO—, —$NR_1$CONR$_2$— or a single bond;

n, m or o are independently of each other numbers from 0 to 8, and if n is 0, then X is a single bond;
if m is 0, then X' is a single bond;
if o is 0, then X" is a single bond;

$R_1$ and $R_2$ are independently of one another hydrogen, $C_1$-$C_{25}$ alkyl, $C_3$-$C_{25}$ alkyl which is interrupted by oxygen or sulfur, $C_6$-$C_{12}$ aryl or R;

$R_{101}$ is $C_1$-$C_{24}$acyl;

$T_1$ has the meaning of R and contains at least one cationic group L;

$T_1'$ has the meaning of R and contains at least one cationic moiety G;

$T_1''$ has the meaning of R and contains at least one moiety Z;

$T_2$, $T_2'$, $T_2''$, $T_3$, $T_3'$, $T_3''$ are independently of one another hydrogen, $C_1$-$C_{25}$alkyl, $C_3$-$C_{25}$alkyl which is interrupted by oxygen or sulphur, $C_2$-$C_{24}$alkenyl, phenyl, $C_7$-$C_9$phenylalkyl, —OR$_3$,

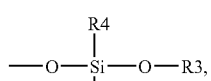

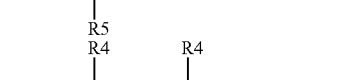

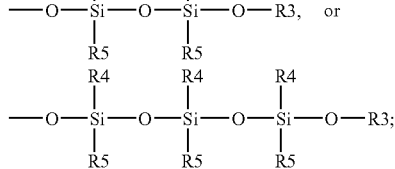

$R_3$ is hydrogen, $C_1$-$C_{25}$alkyl, $C_3$-$C_{25}$alkyl which is interrupted by oxygen or sulphur, $C_2$-$C_{24}$alkenyl, phenyl, $C_7$-$C_9$phenylalkyl,

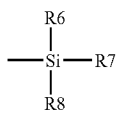

or nanoparticle surface;

$R_4$ and $R_5$ independently of each other are hydrogen, $C_1$-$C_{25}$alkyl, $C_3$-$C_{25}$alkyl which is interrupted by oxygen or sulphur, $C_2$-$C_{24}$alkenyl, phenyl, $C_7$-$C_9$phenylalkyl or —$OR_3$;

$R_6$, $R_7$ and $R_8$ independently of each other are hydrogen, $C_1$-$C_{25}$alkyl, $C_3$-$C_{25}$alkyl which is interrupted by oxygen or sulphur, $C_2$-$C_{24}$alkenyl, phenyl or $C_7$-$C_9$phenylalkyl;

R is $C_1$-$C_{20}$alkyl, $C_5$-$C_{12}$cycloalkyl, $C_2$-$C_{20}$alkenyl, $C_5$-$C_{12}$cycloalkenyl, $C_2$-$C_{20}$alkynyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D or, provided that X', X', or X", has the meaning of a single bond, R can be L, G, or Z;

D is L, G, Z, $R_9$, $OR_9$, $SR_9$, $NR_9R_{10}$, halogen, $NO_2$, CN, O-glycidyl, O-vinyl, O-allyl, $COR_9$, $NR_9COR_{10}$, $COOR_9$, $OCOR_9$, $CONR_9R_{10}$, $OCOOR_9$, $OCONR_9R_{10}$, $NR_9COOR_{10}$, $SO_3H$, $COOM_C$, $COO^-$, $SO_3^-$ or $SO_3M_C$, phenyl, $C_7$-$C_9$alkylphenyl;

E is O, S, COO, OCO, CO, $NR_9$, $NCOR_9$, $NR_9CO$, $CONR_9$, OCOO, OCONR_9, $NR_9COO$, $SO_2$, SO,

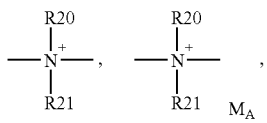

$CR_9$=$CR_{10}$ or

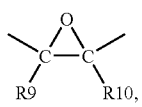

C≡C, N=C—$R_9$, $R_9$C=N, $C_5$-$C_{12}$Cycloalkylene, phenylene and/or phenylene substituted by D;

L and G are independently

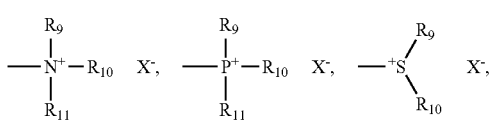

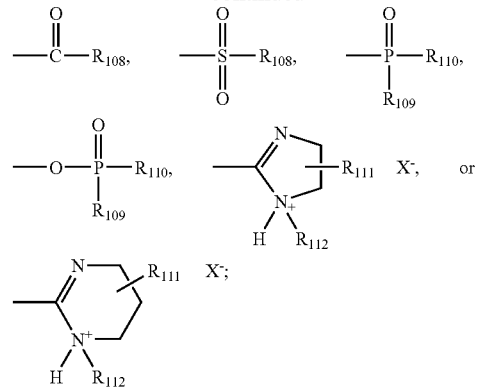

$R_9$, $R_{10}$ or $R_{11}$ independently of one another are hydrogen, $C_1$-$C_{25}$alkyl, benzyl, or phenyl;

$R_{20}$ and $R_{21}$ independently of one another are hydrogen, $C_1$-$C_{25}$alkyl, benzyl, or phenyl;

$R_{108}$, $R_{109}$ and $R_{110}$ are each independently of the others hydroxyl,

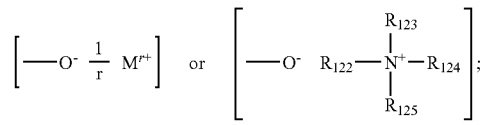

$R_{111}$ is hydrogen or $C_1$-$C_{25}$alkyl;

$R_{112}$ is hydrogen or $C_1$-$C_{25}$alkyl, $C_3$-$C_{25}$alkyl interrupted by oxygen, sulfur or by

or $C_2$-$C_{24}$alkenyl;

$R_{122}$, $R_{123}$, $R_{124}$ and $R_{125}$ are each independently of the others hydrogen, $C_1$-$C_{25}$alkyl or hydroxyl-substituted $C_2$-$C_{24}$alkyl;

M is an r-valent metal cation;

$X^-$ is fluoride, chloride, bromide, iodide, nitrite, nitrate, hydroxide, acetate, hydrogen sulfate, sulfate, methyl sulfate or mixtures thereof;

r is 1, 2 or 3;

Z is halogen, CN, $NO_2$, or a cationic moiety, anionic moiety, hydrophilic moiety, hydrophobic moiety, polysiloxane moiety, polyhalogenated moiety, polyethyleneglycol moiety, polypropyleneglycol moiety, metal complex or a polymer;

$M_C$ is an inorganic or organic cation; and $M_A$ is an inorganic or organic anion.

Another embodiment of the instant invention is a personal care composition comprising a cationic nanoparticle of formula (I) wherein said cationic nanoparticle core of formula (I) comprises an inorganic material wherein the organic substituent covalently bound to the core nanoparticle surface is A, B, and/or C

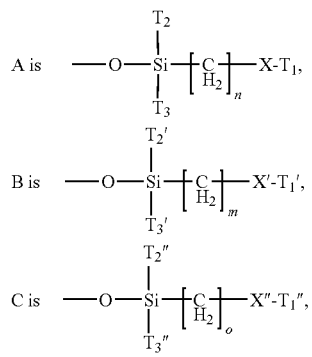

X, X' and X" are independently of one another —O—, —NR$_1$—, —NR$_{101}$—, —OCO—, —NR$_1$CO—, —OCOO—, —NR$_1$COO— or a single bond;

n, m or o are independently of each other numbers from 0 to 6, and if n is 0, then X is a single bond;

if m is 0, then X' is a single bond;

if o is 0, then X" is a single bond;

$R_1$ and $R_2$ are independently of one another hydrogen, $C_1$-$C_{18}$ alkyl, $C_3$-$C_{25}$ alkyl which is interrupted by oxygen, $C_6$-$C_{12}$ aryl or R;

$R_{101}$ is $C_1$-$C_{18}$acyl;

$T_1$ has the meaning of R and contains at least one cationic group L;

$T_1'$ has the meaning of R and contains at least one cationic moiety G;

$T_1''$ has the meaning of R and contains at least one moiety Z;

$T_2$, $T_2'$, $T_2''$, $T_3$, $T_3'$, $T_3''$ are independently of one another $C_1$-$C_{18}$alkyl, $C_3$-$C_{25}$alkyl which is interrupted by oxygen, $C_2$-$C_{24}$alkenyl, phenyl, $C_7$-$C_9$phenylalkyl, or —OR$_3$;

$R_3$ is hydrogen, $C_1$-$C_{18}$alkyl, $C_3$-$C_{25}$alkyl which is interrupted by oxygen, $C_2$-$C_{24}$alkenyl, phenyl, $C_7$-$C_9$phenylalkyl, or nanoparticle surface;

R is $C_1$-$C_{18}$alkylm $C_5$-$C_{12}$cycloalkyl, $C_2$-$C_{20}$alkenyl, $C_5$-$C_{12}$cycloalkenyl, $C_6$-$C_{14}$aryl, $C_1$-$C_{18}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D or, provided that X, X', or X", has the meaning of a single bond, R can be L, G, or Z;

D is L, G, Z, $R_9$, OR$_9$, SR$_9$, NR$_9$R$_{10}$, Cl, Br, I, NO$_2$, CN, COR$_9$, NR$_9$COR$_{10}$, COOR$_9$, OCOR$_9$, CONR$_9$R$_{10}$, OCOOR$_9$, OCONR$_9$R$_{10}$, NR$_9$COOR$_{10}$, SO$_3$H, COOM$_C$, COO$^-$, SO$_3^-$ or SO$_3$M$_C$, phenyl, $C_7$-$C_9$alkylphenyl;

E is O, S, COO, OCO, CO, NR$_9$, NCOR$_9$, NR$_9$CO, CONR$_9$, OCOO, OCONR$_9$, NR$_9$COO, SO$_2$, SO,

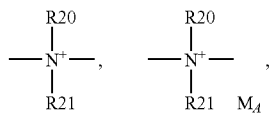

$C_5$-$C_{12}$Cycloalkylene, phenylene and/or phenylene substituted by D;

L and G are independently

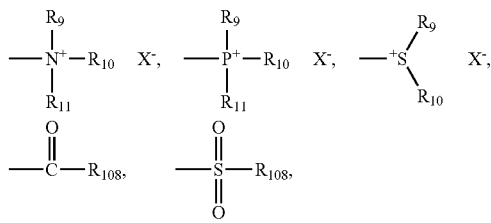

$R_9$, $R_{10}$ or $R_{11}$ independently of one another are hydrogen, $C_1$-$C_{25}$alkyl, benzyl, or phenyl;

$R_{20}$ and $R_{21}$ independently of one another are hydrogen, $C_1$-$C_{25}$alkyl, benzyl, or phenyl;

$R_{108}$ is hydroxyl,

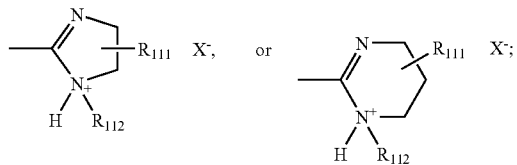

$R_{111}$ is hydrogen or $C_1$-$C_{18}$alkyl;

$R_{112}$ is hydrogen or $C_1$-$C_{18}$alkyl, $C_3$-$C_{25}$alkyl interrupted by oxygen or by

or $C_2$-$C_{24}$alkenyl;

$R_{122}$, $R_{123}$, $R_{124}$ and $R_{125}$ are each independently of the others hydrogen, $C_1$-$C_{18}$alkyl or hydroxyl-substitued $C_2$-$C_{24}$alkyl;

M is an r-valent metal cation;

X$^-$ is fluoride, chloride, bromide, iodide, nitrite, nitrate, hydroxide, acetate, hydrogen sulfate, sulfate, methyl sulfate or mixtures thereof;

r is 1, 2 or 3;

Z is halogen, CN, NO$_2$, or a cationic moiety, anionic moiety, hydrophilic moiety, hydrophobic moiety, polysiloxane moiety, polyethyleneglycol moiety, or, polypropyleneglycol moiety;

M$_C$ is an inorganic or organic cation; and

M$_A$ is an inorganic or organic anion.

Another embodiment of the instant invention is a personal care composition comprising a cationic nanoparticle of formula (I) wherein said cationic nanoparticle core of formula (I) comprises an inorganic material wherein the organic substituent covalently bound to the core nanoparticle surface is A, B, and/or C

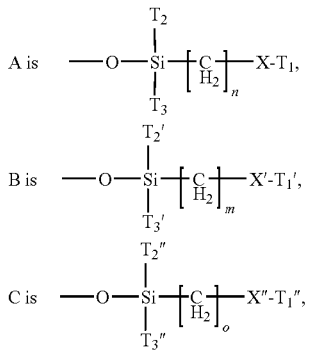

X, X' and X" are independently of one another —O—, —NR$_1$—, —NR$_{101}$—, —OCO—, NR$_1$COO— or a single bond;

n, m or o is independently of each other numbers from 1 to 3;

R$_1$ is hydrogen, C$_1$-C$_{18}$ alkyl, C$_3$-C$_{25}$ alkyl which is interrupted by oxygen, C$_6$-C$_{12}$ aryl or R;

R$_{101}$ is C$_1$-C$_{18}$acyl;

T$_1$ has the meaning of R and contains at least one cationic group L;

T$_1$' has the meaning of R and contains at least one cationic moiety G;

T$_1$" has the meaning of R and contains at least one moiety Z;

T$_2$, T$_2$', T$_2$", T$_3$, T$_3$', T$_3$" are independently of one another C$_1$-C$_{18}$alkyl, C$_3$-C$_{25}$alkyl which is interrupted by oxygen, phenyl, C$_7$-C$_9$phenylalkyl, or —OR$_3$;

R$_3$ is C$_1$-C$_{18}$alkyl, C$_3$-C$_{25}$alkyl which is interrupted by oxygen, phenyln, C$_7$-C$_9$phenylalkyl, or nanoparticle surface;

R is C$_1$-C$_{18}$alkyl, C$_5$-C$_{12}$cycloalkyl, C$_6$-C$_{14}$aryl, C$_1$-C$_{18}$alkyl substituted by one or more D, C$_2$-C$_{20}$alkyl interrupted by one or more E, C$_2$-C$_{20}$alkyl substituted by one or more D and interrupted by one or more E, C$_5$-C$_{12}$cycloalkyl substituted by one or more D, C$_2$-C$_{12}$cycloalkyl interrupted by one or more E, C$_2$-C$_{12}$cycloalkyl substituted by one or more D and interrupted by one or more E, or C$_6$-C$_{14}$aryl substituted by one or more D; or, provided that X, X', or X", has the meaning of a single bond, R can be L, G, or Z;

D is L, G, Z, R$_9$, OR$_9$, NR$_9$R$_{10}$, Cl, Br, I, NR$_9$COR$_{10}$, COOR$_9$, OCOR$_9$, CONR$_9$R$_{10}$, OCONR$_9$R$_{10}$, NR$_9$COOR$_{10}$, SO$_3$H, COOM$_C$, COO$^-$, SO$_3^-$ or SO$_3$M$_C$, phenyl, C$_7$-C$_9$alkylphenyl;

E is O, COO, CO, NR$_9$, NCOR$_9$, NR$_9$CO, CONR$_9$, OCOO, OCONR$_9$, NR$_9$COO, SO$_2$, SO,

C$_5$-C$_{12}$Cycloalkylene, phenylene and/or phenylene substituted by D;

L and G are independently

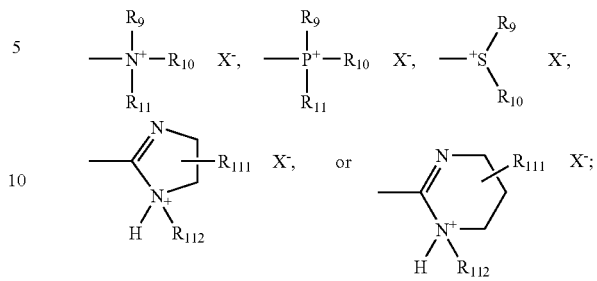

R$_9$, R$_{10}$ or R$_{11}$, independently of one another are hydrogen, C$_1$-C$_{18}$alkyl, benzyl, or phenyl;

R$_{20}$ and R$_{21}$ independently of one another are hydrogen, C$_1$-C$_{18}$alkyl, benzyl, or phenyl;

R$_{111}$ is hydrogen or C$_1$-C$_{18}$alkyl;

R$_{112}$ is hydrogen or C$_1$-C$_{18}$alkyl, C$_3$-C$_{25}$alkyl interrupted by oxygen or

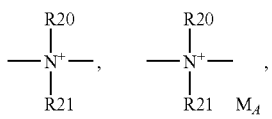

X$^-$ is fluoride, chloride, bromide, iodide, nitrite, nitrate, hydroxide, acetate, hydrogen sulfate, sulfate, methyl sulfate or mixtures thereof;

Z is halogen or a cationic moiety, anionic moiety, hydrophilic moiety, hydrophobic moiety, polysiloxane moiety, polyethyleneglycol moiety, or, polypropyleneglycol moiety;

M$_C$ is an inorganic or organic cation; and

M$_A$ is an inorganic or organic anion.

Another embodiment of the instant invention is a personal care composition wherein said cationic nanoparticle core of formula (I) comprises an inorganic material selected from the group consisting of silicon oxide, Al$_2$O$_3$, TiO$_2$, silicon oxide-coated TiO$_2$, ZnO, SnO$_2$, ZrO$_2$, Ag, Au, Cu, Sb—SnO$_2$, Fe$_2$O$_3$, magnetite, IndiumTinOxide, antimony-doped tin oxide, indium oxide, antimony oxide, fluorine-doped tin oxide, phosphorous-doped tin oxide, zinc antimonite, indium doped zinc oxide and mixtures thereof.

Another embodiment of the instant invention is a personal care composition wherein said cationic nanoparticle core of formula (I) comprises an inorganic material selected from the group consisting of silicon oxide, Al$_2$O$_3$, TiO$_2$, ZnO, SnO$_2$, ZrO$_2$, Sb—SnO$_2$, Fe$_2$O$_3$, magnetite, IndiumTinOxide (ITO), antimony-doped tin oxide (ATO), indium oxide and mixtures thereof.

Another embodiment of the instant invention is a personal care composition wherein said cationic nanoparticle core of formula (I) comprises an inorganic material selected from the group consisting of silicon oxide, Al$_2$O$_3$, TiO$_2$, ZnO, SnO$_2$, ZrO$_2$, Fe$_2$O$_3$, magnetite, IndiumTinOxide (ITO), antimony-doped tin oxide (ATO) and mixtures thereof.

Another embodiment of the instant invention is a personal care composition wherein said cationic nanoparticle core of formula (I) comprises an inorganic material selected from the group consisting of silicon oxide, Al$_2$O$_3$, and mixtures thereof.

Another embodiment of the instant invention is a personal care composition wherein said cationic nanoparticle core of formula (I) comprises an inorganic material selected from the group silicon oxide and its amorphous form.

Another embodiment of the instant invention is a personal care composition comprising a cationic nanoparticle of formula (I) wherein said cationic nanoparticle core of formula (I) comprises an organic material wherein the organic substituent covalently bound to the core nanoparticle surface is A, B, and/or C A is —Y-$T_1$, B is —Y'-$T_1$', C is —Y"-$T_1$";

Y, Y' and Y" are independently of one another $C_1$-$C_{25}$ alkylene, —O—, —S—, —$NR_1$—, —OCO—, —SCO—, —$NR_1$CO—, —OCOO—, —OCON$R_1$—, —$NR_1$COO—, —$NR_1$CON$R_2$—, —COO—, —CON$R_1$—, —CO— or a single bond;

$T_1$ has the meaning of R and contains at least one cationic group L;

$T_1$' has the meaning of R and contains at least one cationic moiety G;

$T_1$" has the meaning of R and contains at least one moiety Z;

$R_1$ and $R_2$ are independently of one another hydrogen, $C_1$-$C_{25}$ alkyl, $C_3$-$C_{25}$ alkyl which is interrupted by oxygen or sulfur, $C_6$-$C_{12}$ aryl or R;

R is $C_1$-$C_{20}$alkyl, $C_5$-$C_{12}$cycloalkyl, $C_2$-$C_{20}$alkenyl, $C_5$-$C_{12}$cycloalkenyl, $C_2$-$C_{20}$alkynyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D or, provided that Y, Y', or Y", has the meaning of a single bond, R can be L, G, or Z;

D is L, G, Z, $R_9$, $OR_9$, $SR_9$, $NR_9R_{10}$, halogen, $NO_2$, CN, O-glycidyl, O-vinyl, O-allyl, $COR_9$, $NR_9COR_{10}$, $COOR_9$, $OCOR_9$, $CONR_9R_{10}$, $OCOOR_9$, $OCONR_9R_{10}$, $NR_9COOR_{10}$, $SO_3H$, $COOM_C$, $COO^-$, $SO_3^-$ or $SO_3M_C$, phenyl, $C_7$-$C_9$alkylphenyl;

E is O, S, COO, OCO, CO, $NR_9$, $NCOR_9$, $NR_9CO$, $CONR_9$, OCOO, OCON$R_9$, $NR_9COO$, $SO_2$, SO,

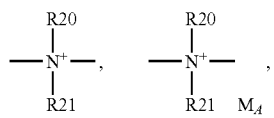

$CR_9=CR_{10}$ or

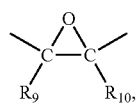

C≡C, N═C—$R_9$, $R_9$C═N, $C_5$-$C_{12}$Cycloalkylene, phenylene and/or phenylene substituted by D;

L and G are independently

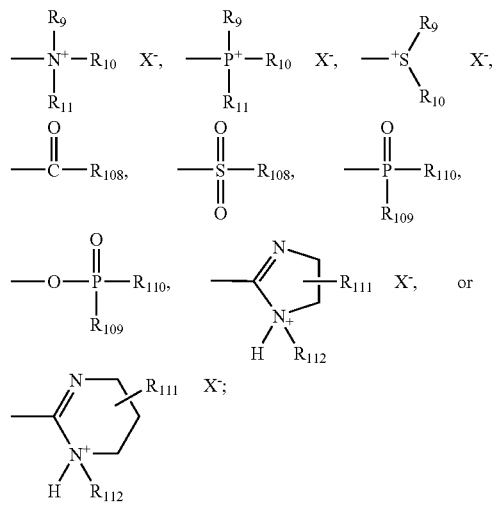

$R_9$, $R_{10}$ or $R_{11}$, independently of one another are hydrogen, $C_1$-$C_{25}$alkyl, benzyl, or phenyl;

$R_{20}$ and $R_{21}$ independently of one another are hydrogen, $C_1$-$C_{25}$alkyl, benzyl, or phenyl;

$R_{108}$, $R_{109}$ and $R_{110}$ are each independently of the others hydroxyl,

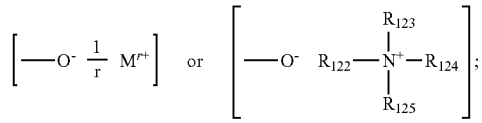

$R_{111}$ is hydrogen or $C_1$-$C_{25}$alkyl;

$R_{112}$ is hydrogen or $C_1$-$C_{25}$alkyl, $C_3$-$C_{25}$alkyl interrupted by oxygen, sulfur or by

or $C_2$-$C_{24}$alkenyl;

$R_{122}$, $R_{123}$, $R_{124}$ and $R_{125}$ are each independently of the others hydrogen, $C_1$-$C_{25}$alkyl or hydroxyl-substituted $C_2$-$C_{24}$alkyl;

M is an r-valent metal cation;

$X^-$ is fluoride, chloride, bromide, iodide, nitrite, nitrate, hydroxide, acetate, hydrogen sulfate, sulfate, methyl sulfate or mixtures thereof;

r is 1, 2 or 3;

Z is halogen, CN, $NO_2$, or a cationic moiety, anionic moiety, hydrophilic moiety, hydrophobic moiety, polysiloxane moiety, polyhalogenated moiety, polyethyleneglycol moiety, polypropyleneglycol moiety, metal complex or a polymer;

$M_C$ is an inorganic or organic cation; and $M_A$ is an inorganic or organic anion.

Another embodiment of the instant invention is a personal care composition comprising a cationic nanoparticle of formula (I) wherein said cationic nanoparticle core of formula (I)

comprises an organic material wherein the organic substituent covalently bound to the core nanoparticle surface is A, B, and/or C A is —Y-$T_1$,
B is —Y'-$T_1$',
C is —Y"-$T_1$";
Y, Y' and Y" are independently of one another $C_1$-$C_{18}$ alkylene, —O—, —S—, —$NR_1$—, —OCO—, —$NR_1$COO—, —COO—, —$CONR_1$—, —CO— or a single bond;
$T_1$ has the meaning of R and contains at least one cationic group L;
$T_1$' has the meaning of R and contains at least one cationic moiety G;
$T_1$" has the meaning of R and contains at least one moiety Z;
$R_1$ and $R_2$ are independently of one another hydrogen, $C_1$-$C_{18}$ alkyl, $C_3$-$C_{25}$ alkyl which is interrupted by oxygen or sulfur, $C_6$-$C_{12}$ aryl or R;
R is $C_1$-$C_{18}$alkyl, $C_5$-$C_{12}$cycloalkyl, $C_2$-$C_{20}$alkenyl, $C_5$-$C_{12}$cycloalkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D or, provided that Y, Y', or Y", has the meaning of a single bond, R can be L, G, or Z;
D is L, G, Z, $R_9$, $OR_9$, $NR_9R_{10}$, Cl, Br, I, $NO_2$, CN, $COR_9$, $NR_9COR_{10}$, $COOR_9$, $OCOR_9$, $CONR_9R_{10}$, $OCOOR_9$, $OCONR_9R_{10}$, $NR_9COOR_{10}$, $SO_3H$, $COOM_C$, $COO^-$, $SO_3^-$ or $SO_3M_C$, phenyl, $C_7$-$C_9$alkylphenyl;
E is O, COO, OCO, CO, $NR_9$, $NCOR_9$, $NR_9CO$, $CONR_9$, $OCONR_9$, $NR_9COO$, $SO_2$, SO,

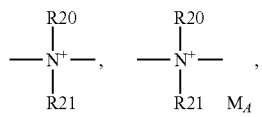

$C_5$-$C_{12}$Cycloalkylene, phenylene and/or phenylene substituted by D;
L and G are independently

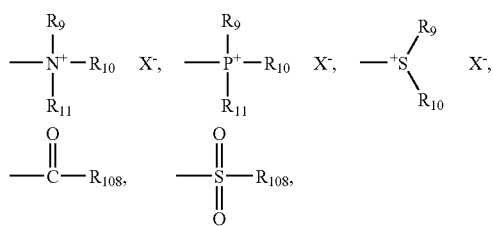

-continued

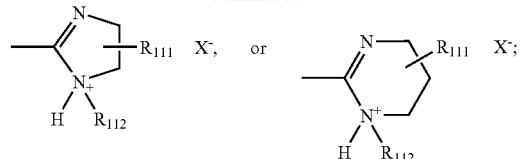

$R_9$, $R_{10}$ or $R_{11}$ independently of one another are hydrogen, $C_1$-$C_{18}$alkyl, benzyl, or phenyl;
$R_{20}$ and $R_{21}$ independently of one another are hydrogen, $C_1$-$C_{18}$alkyl, benzyl, or phenyl;
$R_{108}$ is hydroxyl, $$\left[-O^- \frac{1}{r} M^{r+}\right] \quad \text{or} \quad \left[-O^- R_{122}-\overset{R_{123}}{\underset{R_{125}}{N^+}}-R_{124}\right];$$

$R_{111}$ is hydrogen or $C_1$-$C_{18}$alkyl;
$R_{112}$ is hydrogen or $C_1$-$C_{18}$alkyl, $C_3$-$C_{25}$alkyl interrupted by oxygen, sulfur or by

$R_{122}$, $R_{123}$, $R_{124}$ and $R_{125}$ are each independently of the others hydrogen, $C_1$-$C_{25}$alkyl or hydroxyl-substituted $C_2$-$C_{24}$alkyl;
M is an r-valent metal cation;
$X^-$ is fluoride, chloride, bromide, iodide, nitrite, nitrate, hydroxide, acetate, hydrogen sulfate, sulfate, methyl sulfate or mixtures thereof;
r is 1, 2 or 3;
Z is halogen, CN, $NO_2$, or a cationic moiety, anionic moiety, hydrophilic moiety, hydrophobic moiety, polysiloxane moiety, polyethyleneglycol moiety, or polypropyleneglycol moiety;
$M_C$ is an inorganic or organic cation; and
$M_A$ is an inorganic or organic anion.

Another embodiment of the instant invention is a personal care composition comprising a cationic nanoparticle of formula (I) wherein said cationic nanoparticle core of formula (I) comprises an organic material wherein the organic substituent covalently bound to the core nanoparticle surface is A, B, and/or C A is —Y-$T_1$,
B is —Y'-$T_1$',
C is —Y"-$T_1$";
Y, Y' and Y" are independently of one another $C_1$-$C_{18}$ alkylene, —O—, —$NR_1$—, —OCO—, —$NR_1$CO—, —$OCONR_1$—, —$NR_1$COO—, —COO—, —$CONR_1$— or a single bond;
$T_1$ has the meaning of R and contains at least one cationic group L;
$T_1$' has the meaning of R and contains at least one cationic moiety G;
$T_1$" has the meaning of R and contains at least one moiety Z;
$R_1$ and $R_2$ are independently of one another hydrogen, $C_1$-$C_{18}$ alkyl, $C_3$-$C_{25}$ alkyl which is interrupted by oxygen or sulfur, $C_6$-$C_{12}$ aryl or R;

R is $C_1$-$C_{18}$alkyl, $C_5$-$C_{12}$cycloalkyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, or $C_6$-$C_{14}$aryl substituted by one or more D; or, provided that Y, Y', or Y'', has the meaning of a single bond, R can be L, G, or Z;

D is L, G, Z, $R_9$, $OR_9$, $NR_9R_{10}$, Cl, Br, I, $NO_2$, CN, $COR_9$, $NR_9COR_{10}$, $COOR_9$, $OCOR_9$, $CONR_9R_{10}$, $OCOOR_9$, $OCONR_9R_{10}$, $NR_9COOR_{10}$, $SO_3H$, $COOM_C$, $COO^-$, $SO_3^-$ $SO_3M_C$, phenyl, $C_7$-$C_9$alkylphenyl;

E is O, COO, OCO, CO, $NR_9$, $NCOR_9$, $NR_9CO$, $CONR_9$, $OCONR_9$, $NR_9COO$, $SO_2$, SO,

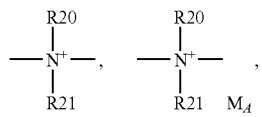

$C_5$-$C_{12}$Cycloalkylene, phenylene and/or phenylene substituted by D;

L and G are independently

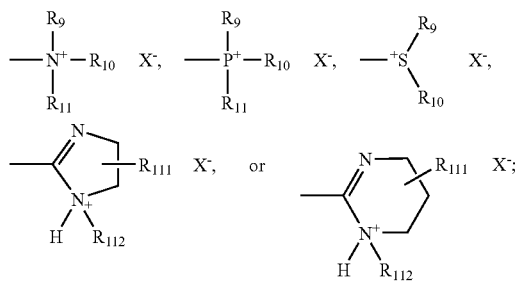

$R_9$, $R_{10}$ or $R_{11}$ independently of one another are hydrogen, $C_1$-$C_{18}$alkyl, benzyl, or phenyl;

$R_{20}$ and $R_{21}$ independently of one another are hydrogen, $C_1$-$C_{18}$alkyl, benzyl, or phenyl;

$R_{111}$ is hydrogen or $C_1$-$C_{18}$alkyl;

$R_{112}$ is hydrogen or $C_1$-$C_{18}$alkyl, $C_3$-$C_{25}$alkyl interrupted by oxygen, sulfur or by

$R_{122}$, $R_{123}$, $R_{124}$ and $R_{125}$ are each independently of the others hydrogen, $C_1$-$C_{25}$alkyl or hydroxyl-substituted $C_2$-$C_{24}$alkyl;

$X^-$ is fluoride, chloride, bromide, iodide, nitrite, nitrate, hydroxide, acetate, hydrogen sulfate, sulfate, methyl sulfate or mixtures thereof;

Z is halogen, CN, $NO_2$, or a cationic moiety, anionic moiety, hydrophilic moiety, hydrophobic moiety, polysiloxane moiety, polyethyleneglycol moiety, or polypropyleneglycol moiety;

$M_C$ is an inorganic or organic cation; and $M_A$ is an inorganic or organic anion.

Another embodiment of the instant invention is a personal care composition comprising a cationic nanoparticle of formula (I) wherein the core of said nanoparticle comprises an organic material which is a polymer comprised of monomeric repeating units. The polymer is a homopolymer, copolymer or terpolymer. The homopolymers, copolymers or terpolymers of the cationic nanoparticle core (organic material) are either crosslinked or not crosslinked.

Another embodiment of the instant invention is a personal care composition comprising a cationic nanoparticle of formula (I) wherein said cationic nanoparticle core comprises an organic material of formula (II)

wherein

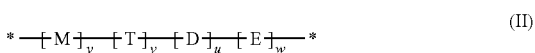

u, v, w, and y represent the percentage by weight that each repeating unit or derived monomer is contained within the organic material;

u, v, w, and y add up to total 100 weight percent relative to the total weight of the organic material;

u and w are independently from about 0 to about 94.9999% by weight of the organic material;

y is from about 5% to about 99.9999% by weight of the organic material;

v is from about 0.0001% to about 5% by weight of the organic material;

* is a terminal group, for example, a catalyst residue;

M, T, D and E are covalently bonded to each other;

M is derived from a monomer of formula (III)

T6, T7, and T8 are C1-C4 alkyl or hydrogen; Y and T1 are defined wherein the specification;

D and E are independently derived from monomers selected from the group consisting of acrylic acid, (meth)acrylic acid, acryloxypropionic acid, crotonic acid, itaconic acid, maleic acid, fumaric acid, citraconic acid, 2-acrylamido-2-methyl propane sulfonic acid, styrene sulfonic acid, vinyl sulfonic acid, sulfoethyl(meth)acrylate, sulfopropyl (meth)acrylate, 2-acrylamido-2-methyl propane sulfinic acid, styrene sulfinic acid, and vinyl sulfinic acid, 2-phosphoethyl (meth)acrylate, vinyl phosphoric acid, vinyl phosphinic acid, N,N-dimethylaminoethyl (meth)acrylate, N,N-diethylaminoethyl(meth)acrylate, N-t-butylaminoethyl(meth)acrylate, N,N-dimethylaminopropyl(meth)acrylamide, p-aminostyrene, N,N-cyclohexylallylamine, allylamine, diallylamine, dimethylallylamine, N-ethyldimethylallylamine, crotyl amines, N-ethylmethallylamine, 2-vinylpyridine, 4-vinylpyridine, vinyl imidazole, oxazolidinylethyl(meth)acrylate, vinylbenzylamines, vinylphenylamines, 2-morpholinoethyl(meth)acrylate, methacrylamidopropyl trimethyl ammonium chloride, diallyl dimethyl ammonium chloride, 2-trimethyl ammonium ethyl methacrylic chloride, dimethyl-N-(3-methacrylamidopropyl)-N-(3-sulfopropyl)ammonium betaine, methyl(meth)acrylate, ethyl(meth)acrylate, propyl(meth)acrylate, butyl(meth)acrylate, isobutyl(meth)acrylate, hexyl(meth)acrylate, cyclohexyl(meth)acrylate, 2-ethylhexyl(meth)acrylate, octyl(meth)acrylate, decyl(meth)acrylate, dodecyl(meth)acrylate, pentadecyl(meth)acrylate, hexadecyl(meth)acrylate, octadecyl(meth)acrylate, nonadecyl(meth)acrylate, styrene, alpha-methylstyrene, vinyltoluene, p-methylstyrene, ethylvinylbenzene, vinyinaphthalene, vinylxylenes, vinyl acetate, vinyl formamide, vinyl chloride, vinyl fluoride, vinyl bromide, vinylidene chloride, vinylidene fluoride, vinylidene bromide and mixtures thereof; and T is derived from monomers selected from the group consisting of divinyl benzene, trivinylbenzene, divinyltoluene, divinylpyridine, divinylnaphthalene divinylxylene, ethyleneglycol di(meth)acrylate, trimethylolpropane tri(meth)acrylate, diethyleneglycol divinyl ether, trivinylcyclohexane, allyl(meth)acrylate, diethyleneglycol di(meth)acrylate, propyleneglycol di(meth)acrylate, 2,2-dimethylpropane-1,3-di(meth)acrylate, 1,3-butylene glycol di(meth)acrylate, 1,4-butanediol di(meth)acrylate, 1,6-hexanediol di(meth)acrylate, tripropylene glycol di(meth)acrylate, triethylene glycol di(meth)acrylate, tetraethylene glycol di(meth)acrylate, polyethylene glycol di(meth)acrylates, polyethylene glycol 200 di(meth)acrylate, polyethylene glycol 600 di(meth)acrylate, ethoxylated bisphenol A di(meth)acrylate, poly(butanediol) di(meth)acrylate, pentaerythritol tri(meth)acrylate, trimethylolpropane triethoxy tri(meth)acrylate, glyceryl propoxy tri(meth)acrylate, pentaerythritol tetra(meth)acrylate, dipentaerythritol monohydroxypenta(meth)acrylate, divinyl silane, trivinyl silane, dimethyl divinyl silane, divinyl methyl silane, methyl trivinyl silane, diphenyl divinyl silane, divinyl phenyl silane, trivinyl phenyl silane, divinyl methyl phenyl silane, tetravinyl silane, dimethyl vinyl disiloxane, poly(methyl vinyl siloxane), poly(vinyl hydro siloxane), poly(phenyl vinyl siloxane), and mixtures thereof.

Another embodiment of the instant invention is a personal care composition comprising a cationic nanoparticle of formula (I) wherein said cationic nanoparticle core comprises an organic material of formula (II) wherein

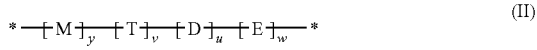
(II)

u, v, w, and y represent the percentage by weight that each repeating unit or derived monomer is contained within the organic material;

u, v, w, and y add up to total 100 weight percent relative to the total weight of the organic material;

u and w are independently from about 10% to about 84.99% by weight of the organic material;

y is from about 15% to about 89.99% by weight of the organic material;

v is from about 0.01% to about 5% by weight of the organic material;

M is derived from a monomer of formula (III)

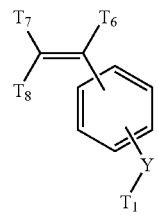
(III)

T6, T7, and T8 are methyl or hydrogen;

D and E are independently derived from monomers selected from the group consisting of acrylic acid, (meth)acrylic acid, acryloxypropionic acid, 2-acrylamido-2-methyl propane sulfonic acid, styrene sulfonic acid, vinyl sulfonic acid, sulfoethyl(meth)acrylate, sulfopropyl(meth)acrylate, 2-phosphoethyl(meth)acrylate, N,N-dimethylaminoethyl(meth)acrylate, N,N-diethylaminoethyl(meth)acrylate, N-t-butylaminoethyl(meth)acrylate, N,N-dimethylaminopropyl(meth)acrylamide, p-aminostyrene, N,N-cyclohexylallylamine, allylamine, diallylamine, dimethylallylamine, N-ethyldimethylallylamine, N-ethylmethallylamine, 2-vinylpyridine, 4-vinylpyridine, vinyl imidazole, methyl(meth)acrylate, ethyl(meth)acrylate, propyl(meth)acrylate, butyl(meth)acrylate, isobutyl(meth)acrylate, hexyl(meth)acrylate, cyclohexyl(meth)acrylate, 2-ethylhexyl(meth)acrylate, octyl(meth)acrylate, decyl(meth)acrylate, dodecyl(meth)acrylate, styrene, alpha-methylstyrene, vinyltoluene, p-methylstyrene, ethylvinylbenzene, vinylxylenes, vinyl acetate, vinyl formamide, vinyl chloride, and mixtures thereof;

T is derived from monomers selected from the group consisting of divinyl benzene, trivinylbenzene, divinyltoluene, divinylpyridine, divinylnaphthalene divinylxylene, ethyleneglycol di(meth)acrylate, trimethylolpropane tri(meth)acrylate, diethyleneglycol divinyl ether, trivinylcyclohexane, allyl(meth)acrylate, diethyleneglycol di(meth)acrylate, propyleneglycol di(meth)acrylate, 2,2-dimethylpropane-1,3-di(meth)acrylate, 1,3-butylene glycol di(meth)acrylate, 1,4-butanediol di(meth)acrylate, 1,6-hexanediol di(meth)acrylate, tripropylene glycol di(meth)acrylate, triethylene glycol di(meth)acrylate, tetraethylene glycol di(meth)acrylate, polyethylene glycol di(meth)acrylates, polyethylene glycol 200 di(meth)acrylate, polyethylene glycol 600 di(meth)acrylate, ethoxylated bisphenol A di(meth)acrylate, poly(butanediol) di(meth)acrylate, pentaerythritol tri(meth)acrylate, trimethylolpropane triethoxy tri(meth)acrylate, glyceryl propoxy tri(meth)acrylate, pentaerythritol tetra(meth)acrylate, dipentaerythritol monohydroxypenta(meth)acrylate, and mixtures thereof.

Another embodiment of the instant invention is a personal care composition comprising a cationic nanoparticle of formula (I) wherein said cationic nanoparticle core comprises an organic material of formula (II) wherein

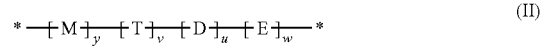
(II)

u, v, w, and y represent the percentage by weight that each repeating unit or derived monomer is contained within the organic material;

u, v, w, and y add up to total 100 weight percent relative to the total weight of the organic material;

u and w are independently from about 25% to about 74.9% by weight of the organic material;

y is from about 25% to about 74.9% by weight of the organic material;

v is from about 0.1% to about 5% by weight of the organic material;

M is derived from a monomer of formula (III)

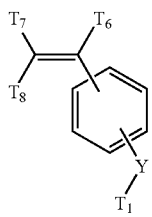

(III)

T6, T7, and T8 are hydrogen;

D and E are independently derived from monomers selected from the group consisting of acrylic acid, (meth)acrylic acid, N,N-dimethylaminoethyl(meth)acrylate, N,N-diethylaminoethyl(meth)acrylate, N-t-butylaminoethyl(meth)acrylate, N,N-dimethylaminopropyl(meth)acrylamide, p-aminostyrene, 2-vinylpyridine, 4-vinylpyridine, vinyl imidazole, methyl(meth)acrylate, ethyl(meth)acrylate, propyl(meth)acrylate, butyl(meth)acrylate, isobutyl(meth)acrylate, hexyl(meth)acrylate, cyclohexyl(meth)acrylate, 2-ethylhexyl(meth)acrylate, styrene, alpha-methylstyrene, vinyltoluene, p-methylstyrene, ethylvinylbenzene, vinyl acetate, and mixtures thereof; and T is derived from monomers selected from the group consisting of divinyl benzene, trivinylbenzene, divinyltoluene, divinylpyridine, ethyleneglycol di(meth)acrylate, trimethylolpropane tri(meth)acrylate, diethyleneglycol divinyl ether, trivinylcyclohexane, allyl(meth)acrylate, diethyleneglycol di(meth)acrylate, propyleneglycol di(meth)acrylate, 2,2-dimethylpropane-1,3-di(meth)acrylate, 1,3-butylene glycol di(meth)acrylate, 1,4-butanediol di(meth)acrylate, 1,6-hexanediol di(meth)acrylate, tripropylene glycol di(meth)acrylate, triethylene glycol di(meth)acrylate, tetraethylene glycol di(meth)acrylate, polyethylene glycol di(meth)acrylates, polyethylene glycol 200 di(meth)acrylate, polyethylene glycol 600 di(meth)acrylate, and mixtures thereof.

Another embodiment of the instant invention is a personal care composition comprising a cationic nanoparticle of formula (I) wherein said cationic nanoparticle core comprises an organic material of formula (II) wherein

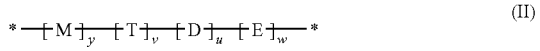

(II)

u and w are independently from about 35% to about 64.9% by weight of the organic material; and y is from about 35% to about 64.9% by weight of the organic material.

The term "(meth)acrylic" includes both acrylic and methacrylic and the term "(meth)acrylate" includes both acrylate and methacrylate. Likewise, the term "(meth)acrylamide" refers to both acrylamide and methacrylamide.

It should be clearly understood that in the actual polymers the various groups may be linked in any order. Thus both block and random copolymers and terpolymers are within the scope of the above formulae.

According to the instant invention, the cationic nanoparticles of formula (I) wherein said cationic nanoparticle core comprises an organic material, the weight average molecular weight of said organic material is from about 1,000 to about 10 million Daltons. Another embodiment of the instant invention is the cationic nanoparticles of formula (I) wherein the core of said nanoparticle comprises an organic material, the weight average molecular weight of said organic material having a weight average molecular weight from about 25,000 to about 5 million Daltons. Another embodiment of the instant invention is the cationic nanoparticles of formula (I) wherein the core of said nanoparticle comprises an organic material, the weight average molecular weight of said organic material having a weight average molecular weight from about 40,000 to about 4 million Daltons. Another embodiment of the instant invention is the cationic nanoparticles of formula (I) wherein the core of said nanoparticle comprises an organic material, the weight average molecular weight of said organic material having a weight average molecular weight from about 50,000 to about 2 million Daltons. Another embodiment of the instant invention is the cationic nanoparticles of formula (I) wherein the core of said nanoparticle comprises an organic material, the weight average molecular weight of said organic material having a weight average molecular weight from about 50,000 to about 1 million Daltons. Another embodiment of the instant invention is the cationic nanoparticles of formula (I) wherein the core of said nanoparticle comprises an organic material, the weight average molecular weight of said organic material having a weight average molecular weight from about 50,000 to about 500,000 Daltons. Another embodiment of the instant invention is the cationic nanoparticles of formula (I) wherein the core of said nanoparticle comprises an organic material, the weight average molecular weight of said organic material having a weight average molecular weight from about 50,000 to about 200,000 Daltons.

The preparation of the polymeric organic material (cationic nanoparticle core, organic material) can be carried out using various polymerization techniques such as solution, emulsion, microemulsion, inverse emulsion, and/or bulk polymerization, as well as other technologies that are available to those who are skilled in the art. The polymerizations can be carried out with or without free radical initiators and with various initiator concentrations. The polymeric organic material can also be prepared in such a way that the architecture of the resulting polymeric organic material is random, block, alternating or core-shell, and with or without the use of polymerization regulators such as nitroxyl ethers or other types of nitroxyl radicals.

Examples of the suitable initiators include, but are not limited to, persulfates such as ammonium persulfate (APS); peroxides such as hydrogen peroxide, t-butyl hydroperoxide, and t-butyl peroxy pivalate; azo initiators such as 2,2'-azobis(2-amidinopropane) dihydrochloride, 4,4'-azobis-4-cyanovaleric acid and 2,2'-azobisisobutyronitrile, and redox initiator systems such as t-butyl hydroperoxide/Fe(II) and ammonium persulfate/bisulfite.

The amount of the free radical initiator used in the polymerization process depends on the total monomer concentration and the type of monomers used, and may range from about 0.2 to about 5.0 wt % of total monomer charge to achieve more than 99% of total monomer conversion.

The polymerization is carried out in the substantial absence of oxygen. Oxygen can be removed from the reaction medium by applying vacuum with agitation or by purging with an inert gas such as nitrogen or argon. The polymerization can then be conducted under a blanket of the inert gas.

Organic substituents bond to the nanoparticle usually by reactive oxygen or sulfur groups (e.g. via —O—, or —S—) on the surface of said particle; while O-bondings as in the above formulae are more preferred in case of an oxydic nanoparticle. Organic substituents bind preferably through groups like e.g. —O—, —S—, —COO—, —OCO—, —NR$_1$CO—, —CONR$_1$ (as defined for Y) to an organic nanoparticle.

Generally, R as T$_1$ contains at least one cationic group L; R as T$_1$' contains at least one cationic moiety G; and R as T$_1$" contains at least one moiety Z; this is to be understood as R being identical with said moiety, or R being substituted by one or more of said moieties. While one class of residues R generally may contain more than one, and more than one type, of functional moiety, e.g. R containing L and G, R containing L and Z, R containing G and Z, R containing L and G and Z, important components from the personal care point of view especially are those wherein R as T$_1$ contains at least one cationic group L and no G and no Z;

R as T$_1$' contains at least one cationic moiety G and no L and no Z; and R as T$_1$" contains at least one moiety Z and no reactive group L and no G. The functional moieties L, G and Z thereby may bond directly to R, or may be bonded over a spacer group such as Q$_1$, Q$_2$ or Q$_3$.

Z may, for example, be selected from, halogen, CN, NO$_2$, alkyls, aryls, alkylaryls, 2,6-polysiloxanes, dialkylphenols, (per)halogenated alkyls, (per)halogenated aryls, (per)halogenated alkylaryls, polyethyleneglycols, polypropyleneglycols, hydroxylated alkyls, hydroxylated aryls, hydroxylated alkylaryls, ammonium salts, phosphonium salts, sulphonium salts, amines, carboxylates, cationic groups, anionic groups, sulfides, polycyclic groups, heterocyclic groups, metal complexes or a polymer, each including derivatives thereof. Of special interest is Z as: a polysiloxane moiety, e.g. selected from polydimethylsiloxanes (characterized by containing the structural unit

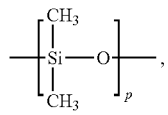

see below), and derivatives thereof;

a halogenated moiety e.g. selected from halogenated alkyls, halogenated aryls, halogenated alkylaryls, perhalogenated moieties such as perhalogenated alkyls, perhalogenated aryls, perhalogenated alkylaryls;

a cationic moiety or ammonium moiety e.g. selected from ammonium salts, phosphonium salts, sulphonium salts; or an anionic moiety.

Z may be, for example, (per)halogenated moieties include —(CF$_2$)$_f$—CF$_3$, where f is a number from 0 to 100;

examples for polysiloxane moieties include those of the formulae

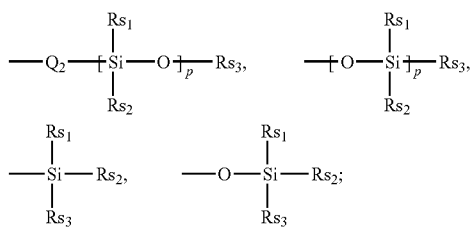

examples for cationic moieties include those of the formulae

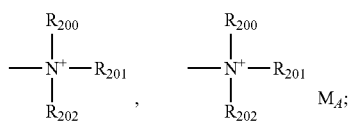

Q$_1$ is O, S or NR$_9$;
Q$_2$ is O, S, NR$_9$, COO, OCO, CONR$_9$, NR$_9$CO, CO, single bond or C$_1$-C$_6$ alkylene;
R$_{s1}$, R$_{s2}$ or R$_{s3}$ are independently of one another hydrogen, C$_1$-C$_{25}$alkyl, C$_1$-C$_{25}$alkyl which is interrupted with oxygen or sulphur, phenyl, C$_7$-C$_9$phenylalkyl, —CH$_2$—CH=CH$_2$,

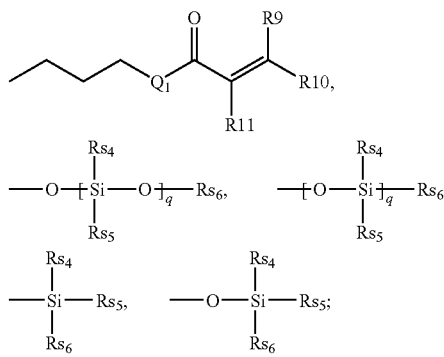

R$_{s4}$, R$_{s5}$ or R$_{s6}$ are independently of one another hydrogen, C$_1$-C$_{25}$alkyl, C$_1$-C$_{25}$alkyl which is interrupted with oxygen or sulphur, phenyl, C$_7$-C$_9$phenylalkyl, —CH$_2$—CH=CH$_2$,

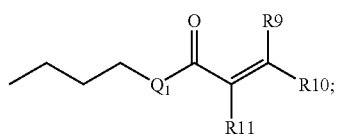

R$_{200}$, R$_{201}$ or R$_{202}$ are independently of one another R$_G$;
R$_G$ is hydrogen, C$_1$-C$_{20}$alkyl, C$_5$-C$_{12}$cycloalkyl, phenyl, naphthyl, biphenyl, C$_1$-C$_{20}$alkyl substituted by one or more D, C$_2$-C$_{20}$alkyl interrupted by one or more E, C$_2$-C$_{20}$alkyl substituted by one or more D and interrupted by one or more E, C$_5$-C$_{12}$cycloalkyl substituted by one or more D, C$_2$-C$_{12}$cycloalkyl interrupted by one or more E, C$_2$-C$_{12}$cycloalkyl substituted by one or more D and interrupted by one or more E, or phenyl substituted by one or more D;
f is a number from 0 to 100;
p is a number from 0 to 100; and
q is a number from 0 to 100.

Nanoparticles suitable for use in the personal care compositions of component a) according to the invention usually are of the formula I as defined above.

One type of nanoparticle or mixtures of different nanoparticles can be used in the personal care compositions and methods according to the instant invention.

The nanoparticle core can be dense or porous.

The core nanoparticle usually consists of only one type of material; however, it is alternatively possible to use a core nanoparticle which comprises an inner core consisting of one material, e.g. a metal or an inorganic oxide, which is covered by one or more layers by another material, e.g. an organic polymer material or another inorganic oxide.

The core nanoparticle usually expresses said inorganic materials on its surface, and preferably consists on one of said materials.

The inorganic nanoparticles (cores) can be produced by sol-gel processes, vapor deposition techniques etc.; the organic nanoparticles can e.g. be produced by microencapsulation techniques (described e.g. in WO 2005/023878). Inorganic nanoparticles as e.g. MT-ST (silicon oxide nano particles) from Nissan Chemical American Corporation, T-1 (ITO) from Mitsubishi Materials Corporation, Passtran (ITO, ATO) form Mitsui Mining & Smelting Co., Ltd., SN-100P (ATO) from Ishihara Sangyo Kaisha, Ltd., NanoTek ITO from C.I. Kasei Co., Ltd., ATO and FTO from Nissan Chemical Industries, Ltd., and other nano particles, e.g. disclosed in WO 2004/090053 are commercially available as e.g. dispersions, e.g. in water, methyl ethyl ketone or alcohols.

The preparation of the compounds of the formula (I) may be carried out in analogy to methods known in the art, e.g. as described in WO06045713 or WO05040289 and literature cited therein, or US-A-2004-138343, or to the examples given below. In general, the particle surface is first modified with a suitable silane coupling agent introducing an active linking group, which is then reacted with the agent(s) introducing the desired functionality or functionalities. Alternatively, the unmodified particle may be reacted directly with one or more coupling agents containing the desired functionality or functionalities. Reaction with more than one modifying agent may be carried out simultaneously or subsequently.

A variety of components as mentioned above, e.g. polymerizable moieties or other functional components such as additives, may be chemically bonded to nanoparticle surfaces such as silica, alumina and silicon aluminum oxide. Possible synthetic routes include the following ones:

1) Particles showing active linkage groups such as —SH or —$NH_2$ (prepared e.g. in accordance or analogy to Example 1 of WO06045713) may easily be surface modified with additives bearing, for instance, a functional group selected from ester-, epoxy-, carboxy-, carbonyl-, acrylic-, methacrylic-, alkylhalogenide-, alkylsulfate-, anhydride-, terminal double bond-, nitrile- and α,β-unsaturated carbonyl-groups. The chemistry of these substances and the molecular organic syntheses (like nucleophilic substitutions, nucleophilic additions, Michael additions, ring-opening reactions, radical addition, etc.) is well known or can easily be adapted to the present solid phase organic chemistry (see also Ex. 9, 10, 11, etc. of WO06045713).

2) Particles showing functional groups on their surfaces such as ester-, epoxy-, carboxy-, carbonyl, acrylic-, methacrylic-, alkylhalogenide-, alkylsulfate-, anhydride-, terminal double bond-, nitrile- and for instance α,β-unsaturated carbonyl-groups may easily be further reacted with an additive bearing a group like —SH, —RNH or —$NH_2$ with the chemical reactions mentioned above.

3) Components such as additives containing a group —OH, —RNH or —$NH_2$ may be activated by using acryloylchlorid under basic conditions to generate a functional acrylate (acylation), which may easily be reacted with particles bearing —SH or —$NH_2$ groups by using a Michael addition; other syntheses leading to functional groups mentioned under 1) and 2) are well known and described in standard chemical literature.

4) Components such as additives may be functionalized by using a reactive agent, such as an alkoxysilane, using functional groups and mechanisms as mentioned under 1), 2) or 3) above, and then directly grafted onto the particle surface, e.g. oxide particle surface such as nanosilica using a state of the art silanisation reaction.

In general, the reactions can be carried out without using a solvent, e.g. with one of the reaction components which is liquid acting as solvent. It is also possible, however, to carry out the reactions in an inert solvent. Examples of suitable solvents are aliphatic or aromatic hydrocarbons such as alkanes and alkane mixtures, cyclohexane, benzene, toluene or xylene, alcohols like methanol, isopropanol or ethanol, ethers like diethylether, dibutylether, dioxane, tetrahydrofuran (THF), for example. Water or aqueous mixtures of solvent are also suitable.

The reactions are conveniently carried out at temperatures adapted to the starting materials and solvents used. The temperatures and other reaction conditions required for the corresponding reactions are generally known and are familiar to the skilled worker. The reaction products can be separated and purified by general, customary methods, for example using centrifugation, precipitation, distillation, recrystallization, etc.

The meanings of the substituents defined in formula (I) in the different radicals are explained below.

Alkyl such as $C_1$-$C_{20}$alkyl is linear or branched and is, for example, $C_1$-$C_{18}$—, $C_1$-$C_{14}$—, $C_1$-$C_{12}$—, $C_1$-$C_8$—, $C_1$-$C_6$— or $C_1$-$C_4$alkyl. Specific examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, dodecyl, tetradecyl, pentadecyl, hexadecyl, octadecyl, icosyl.

$C_2$-$C_{20}$Alkyl interrupted by one or more E, that is by O, S, COO, OCO, CO, $NR_9$, $NCOR_9$, $NR_9CO$, $CONR_9$, OCOO, $OCONR_9$, $NR_9COO$, $SO_2$, SO,

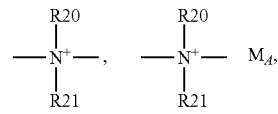

$CR_9$=$CR_{10}$ or

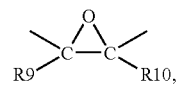

C≡C, N=C—$R_9$, $R_9$C=N, phenylene and/or phenylene substituted by D, for example, interrupted 1-20 times, for example 1-15, 1-10, 1-8, 1-6, 1-5, 1-3, 1-2, or once or twice. The alkyl is linear or branched. This produces structural units such as, for example, —$CH_2$—O—$CH_2$—,

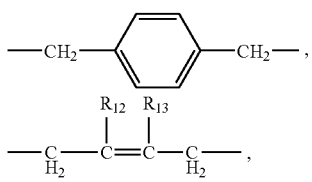

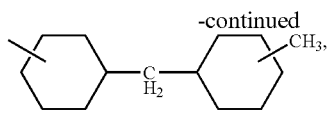

as well as bridged or fused ring systems, e.g.

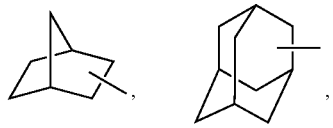

etc. are also meant to be covered by the term.

$C_2$-$C_{20}$Alkynyl radicals are mono or polyunsaturated, linear or branched and are for example $C_2$-$C_8$—, $C_2$-$C_6$— or $C_2$-$C_4$alkynyl. Examples are ethynyl, propynyl, butynyl, 1-butynyl, 3-butynyl, 2-butynyl, pentynyl hexynyl, 2-hexynyl, 5-hexynyl, octynyl, etc.

$C_5$-$C_{12}$Cycloalkylene ($C_5$-$C_{12}$Cycloalkyldiyl) is for example $C_5$-$C_{10}$—, $C_5$-$C_8$—, $C_5$-$C_8$cycloalkylene. Examples are cyclopentylene, cyclohexylene, cyclooctylene, cyclododecylene, especially cyclopentylene and cyclohexylene, preferably cyclohexylene. $C_5$-$C_{12}$cycloalkylene in the context of the present invention is to be also understood as alkylene (alkanediyl) which at least comprises one ring. For example methylcyclopentylene, methyl- or dimethylcyclohexylene,

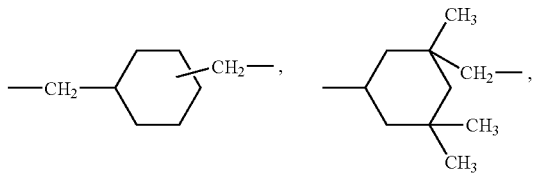

as well as bridged or fused ring systems, e.g.

etc. are also meant to be covered by the term.

Any aryl radical usually stands for an aromatic hydrocarbon moiety of 6 to 14 carbon atoms; specific examples are phenyl, alpha- or beta-naphthyl, biphenylyl.

$C_7$-$C_9$Phenylalkyl is for example benzyl, phenylethyl, alpha-methylbenzyl, phenylpropyl, or alpha,alpha-dimethylbenzyl, especially benzyl.

Any acyl radical such as $R_{101}$ as $C_1$-$C_{24}$acyl is usually selected from mono-acyl residues of $C_1$-$C_{24}$ carboxylic acids, which may be aliphatic or aromatic; examples include $R_{101}$, as —CO—$C_1$-$C_{23}$alkyl; —CO-phenyl; —CO-alkyl which is substituted by COOR$_1$' or COOH or COOMe', where the sum of carbon atoms in the CO, alkyl and COOR$_1$' or COOH or COOMe' moiety in total is from the range 3 to 24; —CO-phenyl which is substituted by R$_1$', COOR$_1$', COOH and/or COOMe', where the sum of carbon atoms in the CO, phenyl, R$_1$' and/or COOR$_1$', COOH, COOMe' present is in total from the range 8 to 24; while R$_1$' is alkyl within the range of carbon —CH$_2$—S—CH$_2$—, —CH$_2$—N(CH$_3$)—CH$_2$—, —CH$_2$CH$_2$—O—CH$_2$CH$_2$—, [CH$_2$CH$_2$O]$_y$—, —[CH$_2$CH$_2$O]$_y$—CH$_2$—, where e.g. y=1-10, —(CH$_2$CH$_2$O)$_7$CH$_2$CH$_2$—, —CH$_2$—CH(CH$_3$)—O—CH$_2$—CH(CH$_3$)— or —CH$_2$—CH(CH$_3$)—O—CH$_2$—CH$_2$CH$_2$—. Interrupting O-atoms are non-successive. If E is O the structural units for interrupted alkyl may also be derived from conventional polyethyleneglycols or polypropyleneglycols, or polytetrahydrofuran of diversified chain lengths. Preferred are such structures to be derived from commercially available polyethyleneglycols, polypropyleneglycols, and polytetrahydrofuran, with for example, MW up to 35000 for polyethyleneglycols, MW up to 35000 for polypropyleneglycols, and MW up to 50000 for polytetrahydrofuran.

Interrupted $C_2$-$C_{20}$alkyl is for example $C_2$-$C_{18}$—, $C_2$-$C_{15}$—, $C_2$-$C_{12}$—, $C_2$-$C_{10}$—, $C_2$-$C_8$—, $C_2$-$C_5$—, $C_2$-$C_3$alkyl. $C_2$-$C_{20}$—, $C_2$-$C_{18}$—, $C_2$-$C_{15}$—, $C_2$-$C_{12}$—, $C_2$-$C_{10}$—, $C_2$-$C_8$—, $C_2$-$C_5$—, $C_2$-$C_3$alkyl interrupted by one or more E have the same meanings as given for $C_2$-$C_{20}$alkyl interrupted by one or more E up to the corresponding number of C-atoms.

If any of the definitions combined with one another lead to consecutive O-atoms, these should be considered excluded in the compounds of formula I in the context of the present application.

$C_2$-$C_{20}$Alkenyl radicals are mono or polyunsaturated, linear or branched and are for example $C_2$-$C_{12}$—, $C_2$-$C_{10}$—, $C_2$-$C_8$—, $C_2$-$C_8$— or $C_2$-$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_3$-$C_{20}$Alkenyl interrupted by one or more E produces similar units as described for interrupted alkyl, wherein one or more alkylene units will be replaced by unsaturated units, that is, the interrupted alkenyl is mono- or polyunsaturated and linear or branched.

$C_5$-$C_{12}$Cycloalkyl is for example $C_4$-$C_{12}$—, $C_5$-$C_{10}$cycloalkyl. Examples are cyclopentyl, cyclohexyl, cyclooctyl, cyclododecyl, especially cyclopentyl and cyclohexyl, preferably cyclohexyl. $C_5$-$C_{12}$cycloalkyl in the context of the present application is to be also understood as alkyl which at least comprises one ring. For example methylcyclopentyl, methyl- or dimethylcyclohexyl,

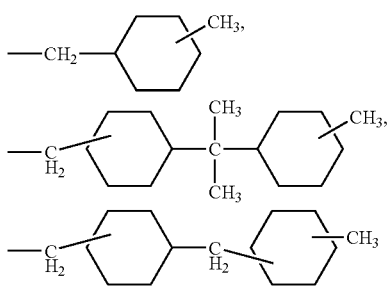

atoms as defined above, preferably $C_1$-$C_4$alkyl, and Me' is an equivalent of a metal cation in oxidation state 1+ or 2+ as defined below for Mc, especially, Li+, Na+, K+. Preferred acyl are residues of $C_1$-$C_{12}$ monocarboxylic acids such as formyl, acetyl, propanoyl, butanoyl, pentanoyl, hexanoyl, heptanoyl, ocanoyl, nonanoyl, decanoyl, undecanoyl (each including straight chain as well as branched variants such as trimethylacetyl), dodecanoyl, acryloyl, methacryloyl, pentenoyl, cinnamoyl, cyclopentanoyl, cyclohexanoyl, cycloheptanoyl, benzoyl, phenylacetyl, hydroxybenzoyl, methylbenzoyl; more preferred are $C_2$-$C_8$alkanoyl, especially acetyl.

Substituted phenyl is substituted one to four times, for example once, twice or three times, especially once. The substituents are for example in 2-, 3-, 4-, 2,4-, 2,6-, 2,3-, 2,5-, 2,4,6-2,3,4-, 2,3,5-position of the phenyl ring.

Halogen is fluorine, chlorine, bromine and iodine. If alkyl is substituted one or more times by halogen, then there are for example 1 to 3 or 1 or 2 halogen substituents on the alkyl radical.

$M_C$ is an inorganic or organic cation; $M_C$ as an n-valent cation is for example $M_{C1}$, a monovalent cation, $M_{C2}$, a divalent cation, $M_{C3}$, a trivalent cation or $M_{C4}$, a tetravalent cation. $M_C$ is for example a metal cation in the oxidation state +1, such as $Li^+$, $Na^+$, $K^+$, $Cs^+$, an "onium" cation, such as ammonium-, phosphonium-, iodonium- or sulfonium cation, a metal cation in the oxidation state +2, such as $Mg^{2+}$, $Ca^{2+}$, $Zn^{2+}$, $Cu^{2+}$, a metal cation in the oxidation state +3, such as $Al^{3+}$, a metal cation in the oxidation state +4, such as $Sn^{4+}$ or $Ti^{4+}$. Examples for onium cations are ammonium, tetraalkylammonium, trialkylarylammonium, dialkyldiarylammonium, tri-arylalkylammonium, tetraarylammonium, tetraalkylphosphonium, tri-alkyl-aryl-phosphonium, di-alkyl-diaryl-phosphonium, tri-aryl-alkyl-phosphonium, tetra-arylphosphonium. For example, $N^+R_{A1}R_{A2}R_{A3}R_{A4}$ or $P^+R_{A1}R_{A2}R_{A3}R_{A4}$, wherein $R_{A1}$, $R_{A2}$, $R_{A3}$, $R_{A4}$ independently of one another are hydrogen, $C_1$-$C_{20}$alkyl, phenyl; $C_1$-$C_{20}$alkyl substituted by OH or phenyl; phenyl substituted by OH or $C_1$-$C_4$ alkyl.

$M_{C1}$ is for example, a metal cation in the oxidation state +1, $N^+R_{A1}R_{A2}R_{A3}R_{A4}$ or $P^+R_{A1}R_{A2}R_{A3}R_{A4}$, wherein $R_{A1}$, $R_{A2}$, $R_{A3}$, $R_{A4}$ independently of one another are hydrogen, $C_1$-$C_{20}$alkyl, phenyl; $C_1$-$C_{20}$alkyl substituted by OH or phenyl; phenyl substituted by OH or $C_1$-$C_4$ alkyl.

$M_{C1}$ is preferably $Li^+$, $Na^+$, $K^+$, $Cs^+$, $N^+R_{A1}R_{A2}R_{A3}R_{A4}$ or $P^+R_{A1}R_{A2}R_{A3}R_{A4}$; in particular $Li^+$, $Na^+$, $K^+$, $N^+R_{A1}R_{A2}R_{A3}R_{A4}$ or $P^+R_{A1}R_{A2}R_{A3}R_{A4}$.

$M_{C2}$ is for example a metal cation in the oxidation state +2; such as for example $Mg^{2+}$, $Ca^{2+}$, $Zn^{2+}$, $M_2$ is preferably $Mg^{2+}$ or $Ca^{3+}$.

$M_{C3}$ is a metal cation in the oxidation state +3; such as for example $Al^{3+}$; $M_{C4}$ is a metal cation in the oxidation state +4; such as for example $Sn^{4+}$ or $Ti^{4+}$. Monovalent cations $M_{C1}$ are preferred.

$M_A$ is an inorganic or organic anion; $M_A$ as an n-valent cation is for example $M_{A1}$, a monovalent anion, $M_{A2}$, a divalent anion, $M_{A3}$, a trivalent anion or $M_{A4}$, a tetravalent anion.

$M_{A1}$ is for example $F^-$, $Cl^-$, $Br^-$, $I^-$, $OH^-$, $C_1$-$C_{20}$—$COO^-$, $C_6$-$C_{12}$aryl-$COO^-$, $C_7$-$C_9$alkylphenyl-$COO^-$, $C_1$-$C_{20}$—$SO_3^-$, haogenated $C_1$-$C_{20}$—$SO_3^-$, $C_7$-$C_9$alkylphenyl-$SO_3^-$ or $C_6$-$C_{12}$aryl-$SO_3^-$; $M_{A1}$ is preferably $F^-$, $Cl^-$, $Br^-$, $I^-$, $C_1$-$C_{20}$—$COO^-$, $CF_3$—$COO^-$, $C_1$-$C_{20}$—$SO_3^-$, $CF_3$—$SO_3^-$ or $C_7$-$C_9$alkylphenyl-$SO_3^-$; $M_{A1}$ is more preferably $Cl^-$, $Br^-$ or $C_1$-$C_6$—$COO^-$;

$M_{A2}$ is for example $CO_3^{2-}$, $SO_4^{2-}$, $^-OOC$—$C_1$-$C_8$-alkylene-$COO^-$ or $^-OOC$-phenylene-$COO^-$; $M_{A2}$ is preferably $CO_3^{2-}$, $SO_4^{2-}$,

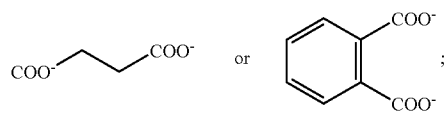

$M_{A2}$ is more preferably $CO_3^{2-}$ or $SO_4^{2-}$;
$M_{A3}$ is for example $PO_4^{3-}$ or

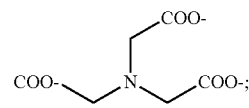

$M_{A4}$ is for example

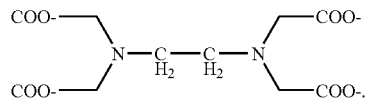

Monovalent anions $M_{A1}$ are preferred.

The above-given examples for the definitions of the radicals are considered illustrative and non-limiting in view of the claimed scope.

The terms "and/or" or "or/and" in the present context are meant to express that not only one of the defined alternatives (substituents) may be present, but also several of the defined alternatives (substituents) together, namely mixtures of different alternatives (substituents).

The term "at least" is meant to define one or more than one, for example one or two or three, etc.

The term "optionally substituted" means that the radical to which it refers is either unsubstituted or substituted.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

The above cationic nanoparticles of the formula I in the personal care compositions according to the invention may be used singly or in any combination with one another or with further known nanoparticles and in principle any compounds and mixtures that form a nanoparticle modified surface.

The above cationic nanoparticles of the formula I in the compositions comprised within personal care products according to the invention may be used singly or in any combination with one another or with further known nanoparticles and in principle any compounds and mixtures that form a nanoparticle modified surface.

The cationic nanoparticles of formula (I) of the instant invention may be fully dissolved or partially dissolved in the personal care composition. The cationic nanoparticles of formula (I) may be in the personal care composition in the form of particles or complexes.

Although there are no critical size limitations to the particles of the cationic nanoparticles of formula (I), the particles having a size of about 0.001 to about 500 micrometers are particularly advantageous. Another embodiment of the instant invention is a particle size for the cationic nanoparticles of formula (I) of about 0.01 to 300 micrometers. Another embodiment of the instant invention is a particle size for the cationic nanoparticles of formula (I) of about 1 to 300 micrometers. Another embodiment of the instant invention is a particle size for the cationic nanoparticles of formula (I) of about 5 to 200 micrometers. Another embodiment of the instant invention is a particle size for the cationic nanoparticles of formula (I) of about 10 to 200 micrometers. Another embodiment of the instant invention is a particle size for the cationic nanoparticles of formula (I) of about 10 to 100 micrometers. Another embodiment of the instant invention is a particle size for the cationic nanoparticles of formula (I) of about 10 to 50 micrometers.

The instant cationic nanoparticles can be present in various physical forms, i.e. solutions, dispersions, suspensions, granules, powders, beads, blocks, etc. In the case of liquid forms such as solutions, dispersions, suspensions, etc., the liquid phase can be aqueous and/or non-aqueous such as a dispersion in soybean oil, an ester or mineral oil. Preferred hydrocarbons as the non-aqueous solvent or dispersion medium include, but are not limited to, naphthol spirits, ESCAID 110 from Exxon, LPA 170 from Condea Vista and CONOSOL 200 from Penreco, an aromatics/paraffins/naphthalenes mixture.

The term "effective amount" means for example the amount necessary to achieve the desired effect.

The cationic nanoparticles of formula (I) of the personal care compositions preferably comprise no more than about 50 weight percent of the composition; more preferably no more than about 25 weight percent of the personal care composition; even more preferably no more than about 7 weight percent; and still more preferably no more than about 5 weight percent. The cationic nanoparticles of formula (I) of the personal care composition preferably comprise at least about 0.0001 weight percent of the personal care composition, more preferably at least about 0.01 weight percent, even more preferably at least about 0.1 weight percent, and still more preferably at least about 0.2 by weight of the composition.

The present personal care compositions may comprise further traditional additives, for example ultraviolet (UV) light absorbers and antioxidants.

Accordingly, the present invention further pertains to a personal care composition comprising
(a) an effective amount of at least one cationic nanoparticle of formula (I)

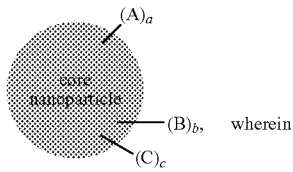

(I)

wherein the core nanoparticle comprises an inorganic or organic material and where A is an organic substituents covalently bound to the core nanoparticle surface and containing at least one cationic group L;

B is an organic substituent covalently bound to the core nanoparticle surface and containing at least one cationic moiety G;

C is an organic substituent covalently bound to the core nanoparticle surface containing at least one functional group Z;

a is a number from 1 to $n_a$;
b is a number from 0 to $n_b$;
c is a number from 0 to $n_c$;

where the sum of $n_a+n_b+n_c$ is a number from 1 up to $n_t$, where $n_t$ is limited by the geometry and surface area of the core nanoparticle and the steric requirements of the respective substituents A, B, C;

(b) a cosmetically acceptable adjuvant; and
(c) at least one compound selected from the group consisting of ultraviolet light absorbers, antioxidants, tocopherol, tocopherol acetate, hindered amine light stabilizers, complex formers, optical brighteners, surfactants and polyorganosiloxanes.

The definition of the substituents and or groups of formula (I) of component a) are defined above.

The additional additives of present component (c) are for example those disclosed in co-pending U.S. application Ser. No. 09/830,788, filed May 1, 2001 and Ser. No. 09/830,787, filed May 1, 2001. The disclosures of these co-pending applications are hereby incorporated by reference. These applications are published as WO 00/25730 and WO 00/25731.

The UV (ultraviolet light) absorbers are for example selected from the group consisting of 2H-benzotriazoles, s-triazines, benzophenones, alpha-cyanoacrylates, oxanilides, benzoxazinones, benzoates and alpha-alkyl cinnamates.

The UV absorbers are, for example:
2,4,6-tris(2-hydroxy-4-octyloxyphenyl)-1,3,5-triazine;
2-(2,4-dihydroxyphenyl)-4,6-bis(2,4-dimethylphenyl)-1,3,5-triazine;
2,4-bis(2-hydroxy-4-propyloxyphenyl)-6-(2,4-dimethylphenyl)-1,3,5-triazine;
2-(2-hydroxy-4-octyloxyphenyl)-4,6-bis(4-methylphenyl)-1,3,5-triazine;
2-(2-hydroxy-4-dodecyloxyphenyl)-4,6-bis(2,4-dimethylphenyl)-1,3,5-triazine;
2-[2-hydroxy-4-(2-hydroxy-3-butyloxypropyloxy)phenyl]-4,6-bis(2,4-dimethylphenyl)-1,3,5-triazine;
2-[2-hydroxy-4-(2-hydroxy-3-octyloxypropyloxy)phenyl]-4,6-bis(2,4-dimethylphenyl)-1,3,5-triazine;
2-[2-hydroxy-4-(2-hydroxy-3-tridecyloxy-propyloxy)phenyl]-4,6-bis(2,4-dimethylphenyl)-1,3,5-triazine;
5-chloro-2-(2-hydroxy-3,5-di-tert-butylphenyl)-2H-benzotriazole;
2-(2-hydroxy-3-dodecyl-5-methylphenyl)-2H-benzotriazole;
5-chloro-2-(2-hydroxy-3-tert-butyl-5-methylphenyl)-2H-benzotriazole;
bis-(3-(2H-benzotriazol-2-yl)-2-hydroxy-5-tert-octyl)methane;
2-(2-hydroxy-3,5-di-tert-butylphenyl)-2H-benzotriazole;
2-(2-hydroxy-3,5-di-tert-amylphenyl)-2H-benzotriazole;
2-(2-hydroxy-3,5-di-alpha-cumylphenyl)-2H-benzotriazole;
2-(2-hydroxy-3-alpha-cumyl-5-tert-octylphenyl)-2H-benzotriazole;
2-(2-hydroxy-5-tert-octylphenyl)-2H-benzotriazole;
3-(2H-benzotriazol-2-yl)-4-hydroxy-5-(1-methylpropyl)-benzenesulfonic acid monosodium salt;
3-tert-butyl-4-hydroxy-5-(2H-benzotriazol-2-yl)-hydrocinnamic acid and sodium salt;
12-hydroxy-3,6,9-trioxadodecyl 3-tert-butyl-4-hydroxy-5-(2H-benzotriazol-2-yl)-hydrocinnamate;
octyl 3-tert-butyl-4-hydroxy-5-(2H-benzotriazol-2-yl)-hydrocinnamate;
4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers);
4,6-bis(2,4-dimethylphenyl)-2-(4-octyloxy-2-hydroxyphenyl)-s-triazine;
2,4-dihydroxybenzophenone;

2,2'-dihydroxy-4,4'-dimethoxy-5,5'-disulfobenzophenone, disodium salt;
2-hydroxy-4-octyloxybenzophenone;
2-hydroxy-4-dodecyloxybenzophenone;
2,4-dihydroxybenzophenone;
2,2',4,4'-tetrahydroxybenzophenone;
4-aminobenzoic acid;
2,3-dihydroxypropyl-4-aminobenzoic acid;
3-(4-imidazolyl)acrylic acid;
2-phenyl-5-benzimidazole sulfonic acid;
N,N,N-trimethyl-alpha-(2-oxo-3-bornylidene)-p-toluidinium methyl sulfate;
5-benzoyl-4-hydroxy-2-methoxybenzenesulfonic acid, sodium salt;
3-(4-benzoyl-3-hydroxyphenoxy)-2-hydroxy-N,N,N-trimethyl-1-propanaminium chloride;
3-[4-(2H-benzotriazol-2-yl)-3-hydroxyphenoxy]-2-hydroxy-N,N,N-trimethyl-1-propanaminium, chloride;
2-(2-hydroxy-5-methylphenyl)-2H-benzotriazole; and
2,2'-dihydroxy-4,4'-dimethoxybenzophenone (Uvinul® 3049).

For instance, suitable UV absorbers are selected from:
3-(2H-benzotriazol-2-yl)-4-hydroxy-5-(1-methylpropyl)-benzenesulfonic acid monosodium salt;
3-tert-butyl-4-hydroxy-5-(2H-benzotriazol-2-yl)-hydrocinnamic acid and sodium salt;
2-(2-hydroxy-3,5-di-tert-butylphenyl)-2H-benzotriazole;
2-(2-hydroxy-3,5-di-tert-amylphenyl)-2H-benzotriazole;
4,6-bis(2,4-dimethylphenyl)-2-(4-(3-dodecyloxy*-2-hydroxypropoxy)-2-hydroxyphenyl)-s-triazine (*is mixture of $C_{12-14}$oxy isomers);
12-hydroxy-3,6,9-trioxadodecyl 3-tert-butyl-4-hydroxy-5-(2H-benzotriazol-2-yl)-hydrocinnamate;
2,4-dihydroxybenzophenone;
2,2'-dihydroxy-4,4'-dimethoxy-5,5'-disulfobenzophenone, disodium salt;
2,2',4,4'-tetrahydroxybenzophenone;
3-(4-benzoyl-3-hydroxyphenoxy)-2-hydroxy-N,N,N-trimethyl-1-propanaminium chloride;
3-[4-(2H-benzotriazol-2-yl)-3-hydroxyphenoxy]-2-hydroxy-N,N,N-trimethyl-1-propanaminium, chloride;
5-benzoyl-4-hydroxy-2-methoxy-benzenesulfonic acid, sodium salt; and
2-(2-hydroxy-3-alpha-cumyl-5-tert-octylphenyl)-2H-benzotriazole.

Additional suitable antioxidants are for example selected from the hindered phenolic and benzofuranone stabilizers.

Suitable antioxidants are, for example, selected from the group consisting of

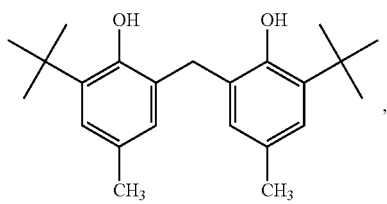
,

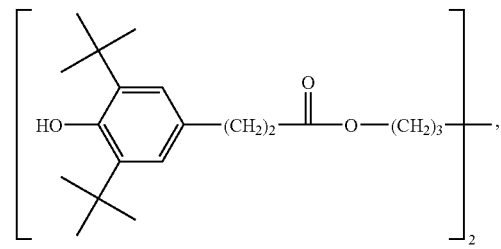
,

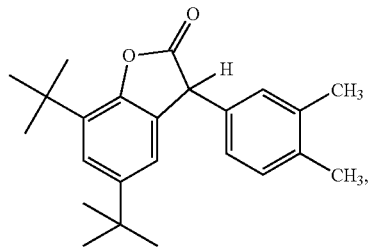
,

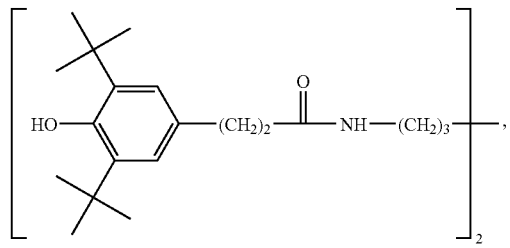
,

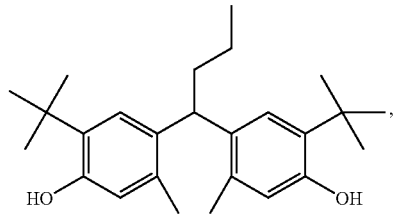
,

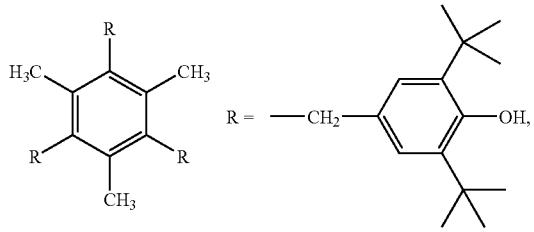

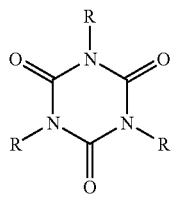

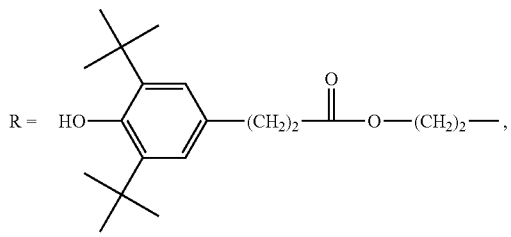
,

33
-continued
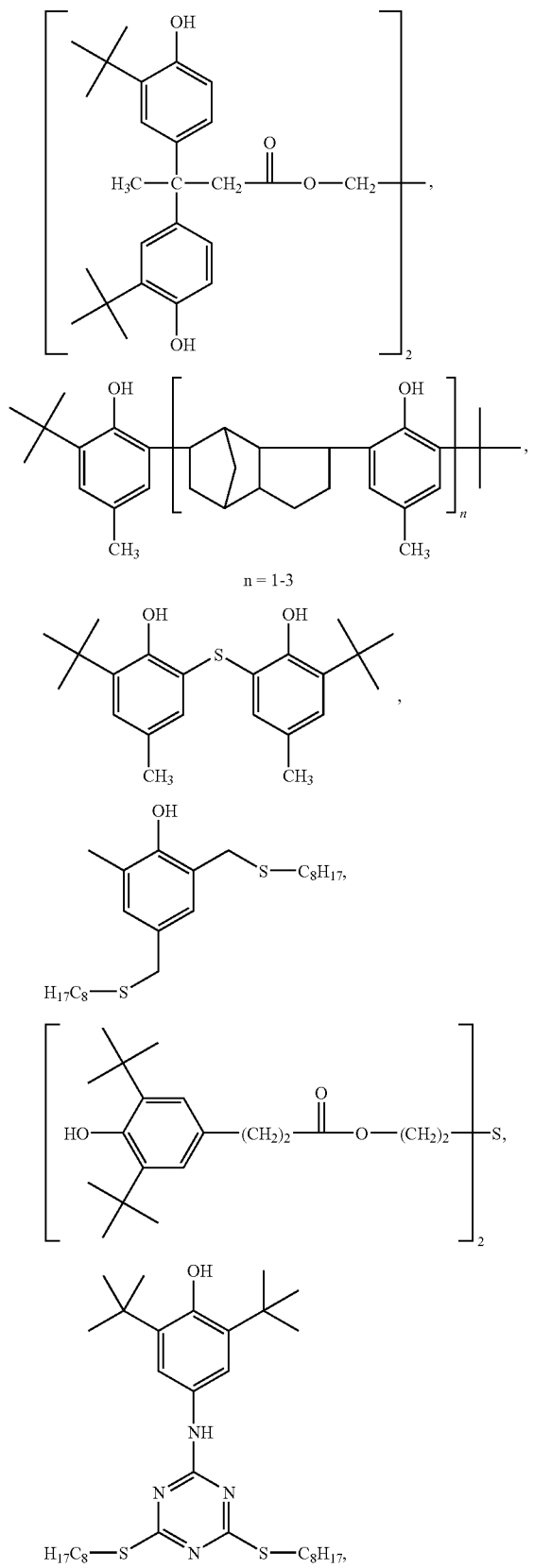
34
-continued
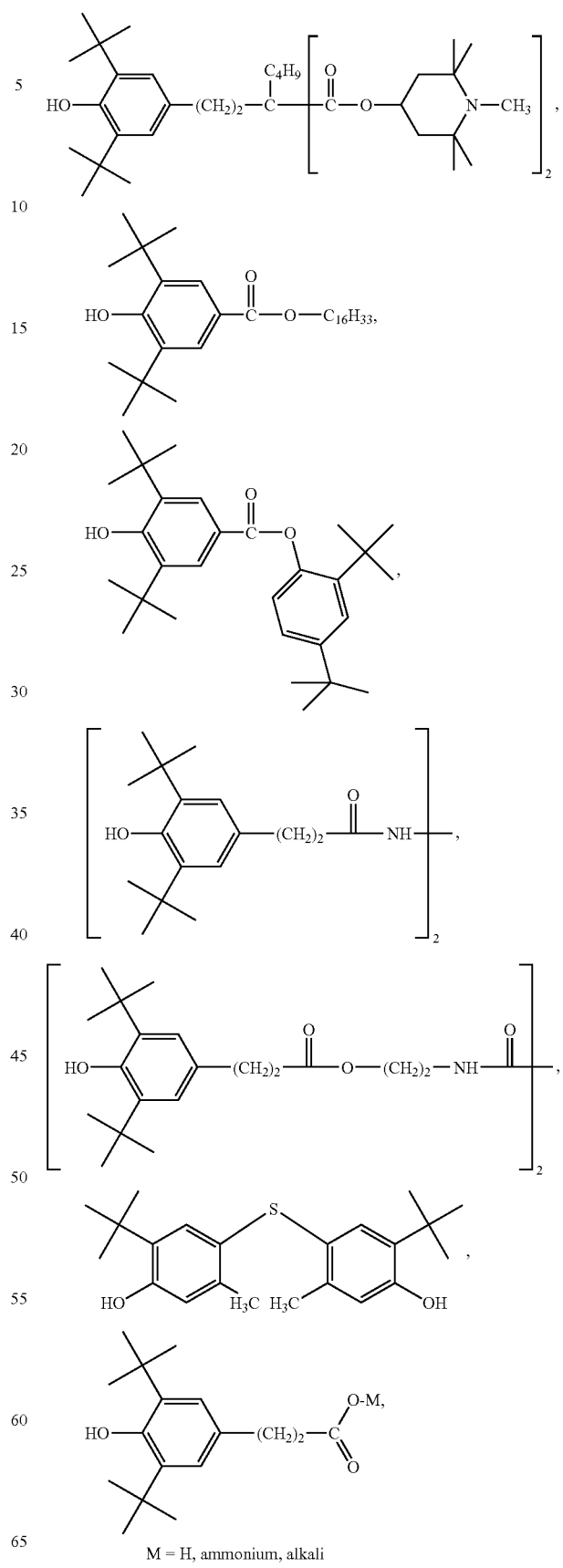
M = H, ammonium, alkali

-continued

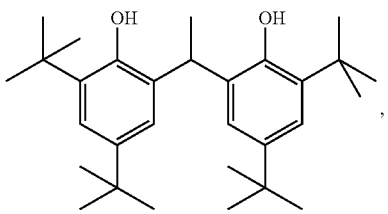

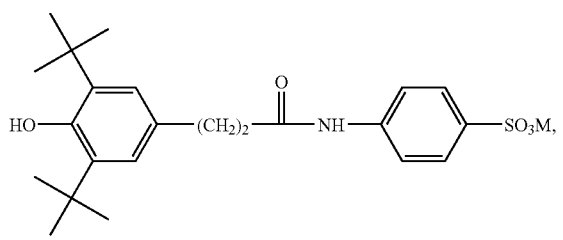

M = H, Na

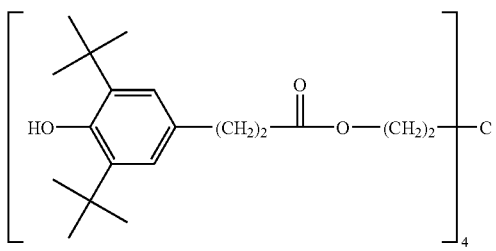

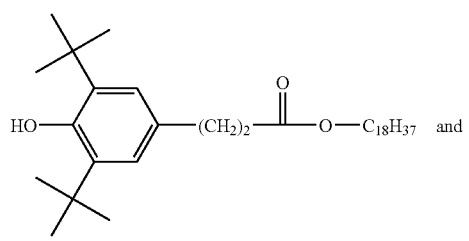

and

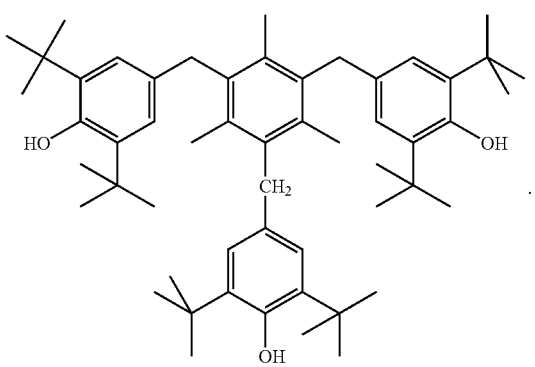 [SMILES: Cc1c(Cc2cc(C(C)(C)C)c(O)c(C(C)(C)C)c2)c(C)c(Cc2cc(C(C)(C)C)c(O)c(C(C)(C)C)c2)c(C)c1Cc1cc(C(C)(C)C)c(O)c(C(C)(C)C)c1]

The hindered amine light stabilizers (HALS) of component (c) are for example known commercial compounds. They are for example selected from the group consisting of bis(2,2,6,6-tetramethylpiperidin-4-yl)sebacate, bis(2,2,6,6-tetramethylpiperidin-4-yl)succinate, bis(1,2,2,6,6-pentamethylpiperidin-4-yl)sebacate, n-butyl-3,5-di-tert-butyl-4-hydroxybenzylmalonic acid-bis(1,2,2,6,6-pentamethylpiperidyl)ester, the condensate of 1-hydroxyethyl-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, the condensate of N,N-bis(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)-pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and 4-butylamino-2,2,6,6-tetramethylpiperidine (CAS reg. No. [136504-96-6]); (2,2,6,6-tetramethyl-4-piperidyl)-n-dodecylsuccinimide, (1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, the reaction product of 7,7,9,9-tetramethyl-2-cycloundecyl-1-oxa-3,8-diaza-4-oxospiro[4,5]decane and epichlorohydrin, tetra(2,2,6,6-tetramethylpiperidin-4-yl)-butane-1,2,3,4-tetracarboxylate, tetra(1,2,2,6,6-pentamethylpiperidin-4-yl)-butane-1,2,3,4-tetracarboxylate, 2,2,4,4-tetramethyl-7-oxa-3,20-diaza-21-oxo-dispiro[5.1.11.2]-heneicosan, 8-acetyl-3-dodecyl-1,3,8-triaza-7,7,9,9-tetramethylspiro[4,5]-decane-2,4-dione,

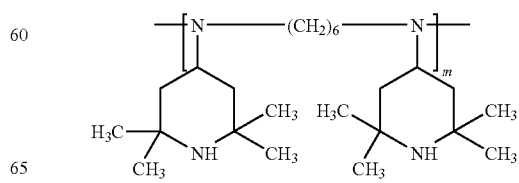

wherein m is a value from 5-50,

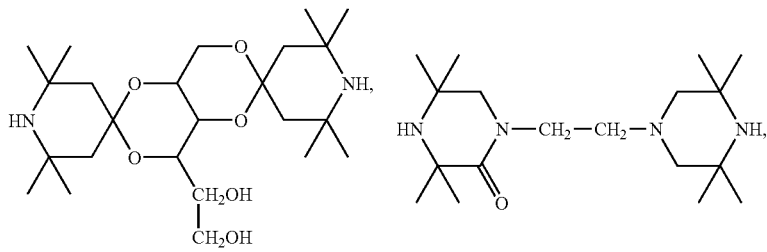

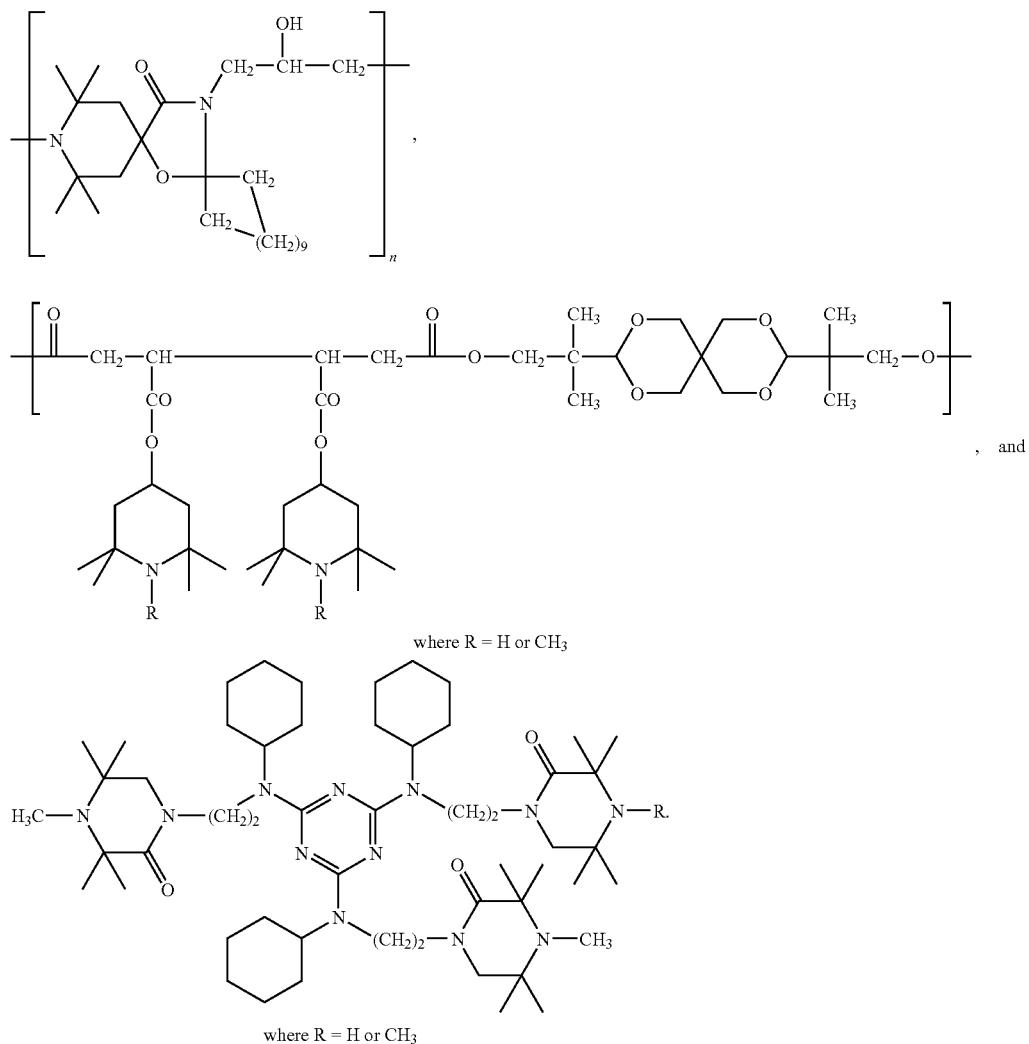

The complex formers of component (c) are for example nitrogen-containing complex formers or polyanionically-derived natural polysaccharides, for example those containing phosphate, phosphonate or methylphosphonate groups, such as chitin derivatives, e.g. sulfochitin, carboxymethylchitin, phosphochitin or chitosan derivatives, for example sulfochitosan, carboxymethylchitosan or phosphochitosan.

The complex formers of component (c) are, for example, selected from the group consisting of ethylenediaminetetracetic acid (EDTA), nitrilotriacetic acid (NTA), beta-alaninediacetic acid (EDETA) or ethylenediaminedisuccinic acid (EDDS), aminetrimethylenephosphoric acid (ATMP) conforming to formula

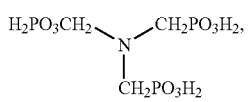

serinediacetic acid (SDA) conforming to formula

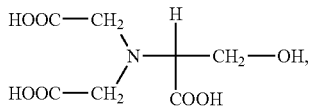

asparaginediacetic acid conforming to formula

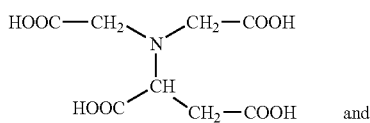 [SMILES: O=C(O)CC(C(=O)O)N(CC(=O)O)CC(=O)O ; "and"]   and methylglycinediacetic acid (MGDA) conforming to formula

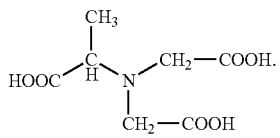

The polyorganosiloxanes of component (c) are, for example, listed in WO 2001/41719, U.S. Pat. No. 6,432,894, U.S. Pat. No. 6,383,995, US 2004/0105832 and U.S. Pat. No. 6,403,542, the US references are herein incorporated by reference.

Component (c) of the personal care compositions preferably comprise no more than about 10 weight percent of the composition; more preferably no more than about 7 weight percent of the personal care composition; even more preferably no more than about 5 weight percent; and still more preferably no more than about 3 weight percent. The component (c) of the personal care composition preferably comprise at least about 0.0001 weight percent of the personal care composition, more preferably at least about 0.01 weight percent, even more preferably at least about 0.1 weight percent, and still more preferably at least about 0.2 by weight of the composition.

The present cationic nanoparticles of formula (I) are particularly suitable for personal care compositions or products, in particular for use in skin-care products, as bath and shower products, preparations containing fragrances and odoriferous substances, hair-care products, dentifrices, deodorizing and antiperspirant preparations, decorative preparations, light protection formulations and preparations containing active ingredients.

Suitable skin-care products are, in particular, body oils, body lotions, body gels, treatment creams, skin protection ointments, shaving preparations, such as shaving foams or gels, skin powders, such as baby powder, moisturizing gels, moisturizing sprays, revitalizing body sprays, cellulite gels and peeling preparations.

Preparations containing fragrances and odoriferous substances are in particular scents, perfumes, and shaving lotions (aftershave preparations).

Suitable hair-care products are, for example, shampoos for humans and animals, in particular dogs and cats, hair conditioners, products for styling and treating hair, perming agents, hair sprays and lacquers, hair gels, hair fixatives and hair dyeing or bleaching agents.

Suitable dentifrices are in particular tooth creams, toothpastes, mouthwashes, mouth rinses, anti-plaque preparations and cleaning agents for dentures.

Suitable decorative preparations are in particular lipsticks, nail varnishes, eye shadows, mascaras, dry and moist make-up, rouge, powders, depilatory agents and suntan lotions.

Suitable cosmetic formulations containing active ingredients are in particular hormone preparations, vitamin preparations, vegetable extract preparations and antibacterial preparations.

The present personal care compositions or products can be in the form of creams, ointments, pastes, foams, gels, lotions, powders, make-ups, sprays, sticks or aerosols. The present cationic nanoparticles of formula (I) may be present in the oil phase or in the aqueous or aqueous/alcoholic phase.

Creams are oil-in-water emulsions containing more than 50% water. The oil-containing base used therein is usually mainly fatty alcohols, for example lauryl, cetyl or stearyl alcohol, fatty acids, for example palmitic or stearic acid, liquid to solid waxes, for example isopropylmyristate or beeswax and/or hydrocarbon compounds, such as paraffin oil. Suitable emulsifiers are surfactants having primarily hydrophilic properties, such as the corresponding non-ionic emulsifiers, for example fatty acid esters of polyalcohols of ethylene oxide adducts, such as polyglycerol fatty acid ester or polyoxyethylenesorbitan fatty acid ether (TWEEN trademarks); polyoxyethylene fatty alcohol ether or their esters or the corresponding ionic emulsifiers, such as the alkali metal salts of fatty alcohol sulfonates, sodium cetyl sulfate or sodium stearyl sulfate, which are usually used together with fatty alcohols, such as cetyl alcohol or stearyl alcohol. In addition, creams contain agents which reduce water loss during evaporation, for example polyalcohols, such as glycerol, sorbitol, propylene glycol, and/or polyethylene glycols.

Ointments are water-in-oil emulsions which contain up to 70%, for instance not more than 20 to 50%, of water or of an aqueous phase. The oil-containing phase contains predominantly hydrocarbons, such as paraffin oil and/or solid paraffin which for instance contains hydroxy compounds, for example fatty alcohol or their esters, such as cetyl alcohol or wool wax for improving the water absorption. Emulsifiers are corresponding lipophilic substances, such as sorbitan fatty acid ester. In addition, the ointments contain moisturizers such as polyalcohols, for example glycerol, propylene glycol, sorbitol and/or polyethylene glycol as well as preservatives.

Rich creams are anhydrous formulations and are produced on the basis of hydrocarbon compounds, such as paraffin, natural or partially synthetic fats, for example coconut fatty acid triglycerides or, for instance, hardened oils and glycerol partial fatty acid esters.

Pastes are creams and ointments containing powdered ingredients which absorb secretions, for example metal oxides, such as titanium dioxide or zinc oxide, and also tallow and/or aluminium silicates which bind the moisture or the absorbed secretion.

Foams are liquid oil-in-water emulsions in aerosol form. Hydrocarbon compounds are used, inter alia, for the oil-containing phase, for example paraffin oil, fatty alcohols, such as cetyl alcohol, fatty acid esters, such as isopropylmyristate and/or waxes. Suitable emulsifiers are, inter alia, mixtures of emulsifiers having predominantly hydrophilic properties, for example polyoxyethylenesorbitan fatty acid ester, and also emulsifiers having predominantly lipophilic properties, for example sorbitan fatty acid ester. Commercially available additives are usually additionally employed, for example preservatives.

Gels are, in particular, aqueous solutions or suspensions of active substances in which gel formers are dispersed or swelled, in particular cellulose ethers, such as methyl cellulose, hydroxyethyl cellulose, carboxymethyl cellulose or vegetable hydrocolloids, for example sodium alginate, tragacanth or gum Arabic and polyacrylate thickener systems. The gels for example additionally contain polyalcohols, such as propylene glycol or glycerol as moisturizers and wetting agents, such as polyoxyethylenesobitan fatty acid ester. The gels furthermore contain commercially available preservatives, such as benzyl alcohol, phenethyl alcohol, phenoxyethanol and the like.

The following is a partial list of examples of personal care products of this invention and their ingredients:

| Body care product | Ingredients |
|---|---|
| moisturizing cream | vegetable oil, emulsifier, thickener, perfume, water, antioxidant, UV absorbers, cationic nanoparticles of the instant invention |
| shampoo | surfactant, emulsifier, preservatives, perfume, antioxidant, UV absorbers, cationic nanoparticles of the instant invention |
| toothpaste | cleaning agent, thickener, sweetener, flavor, colorant, antioxidant, water, UV absorbers, cationic nanoparticles of the instant invention |
| lip-care stick | vegetable oil, wax, $TiO_2$, antioxidant, UV absorbers, cationic nanoparticles of the instant invention |

The present personal care compositions may further comprise dyes, pigments or mixtures thereof.

Accordingly, the present invention further pertains to a personal care composition comprising
(a) an effective amount of at least one cationic nanoparticle of formula (I)

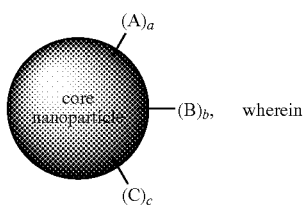

$$(A)_a \quad (B)_b \quad (C)_c \quad \text{(I)}$$

wherein the core nanoparticle comprises an inorganic or organic material and where
A is an organic substituents covalently bound to the core nanoparticle surface and containing at least one cationic group L;
B is an organic substituent covalently bound to the core nanoparticle surface and containing at least one cationic moiety G;
C is an organic substituent covalently bound to the core nanoparticle surface containing at least one functional group Z;
a is a number from 1 to $n_a$;
b is a number from 0 to $n_b$;
c is a number from 0 to $n_c$;
where the sum of $n_a + n_b + n_c$ is a number from 1 up to $n_l$, where $n_l$ is limited by the geometry and surface area of the core nanoparticle and the steric requirements of the respective substituents A, B, C;
(b) a cosmetically acceptable adjuvant, and
(d) a dye or a pigment or mixtures thereof.

Dyes of component (d) according to the present invention are for example:
disperse dyes which may be solubilized in solvents like direct hair dyes of the HC type, for example HC Red No. 3, HC Blue No. 2 and all other hair dyes listed in International Cosmetic Ingredient Dictionary and Handbook, 7$^{th}$ edition 19997) or the dispersion dyes listed in Color Index International or Society of Dyers and Colourists;
color varnishes (insoluble salts of soluble dyes, like many Ca-, Ba- or Al-salts of anionic dyes);
soluble anionic or cationic dyes, like acid dyes (anionic), basic dyes (cationic), direct dyes, reactive dyes or solvent dyes.

Generally, for the coloration of personal care compositions, all substances are suitable which have an absorption in the visible light of electromagnetic radiation (wavelength of ca. 4000 to 700 nm). The absorption is often caused by the following chromophores:

Azo- (mono-, di, tris-, or poly-)stilbene-, carotenoide-, diarylmethan-, triarylmethan-, xanthen-, acridin-, quinoline, methin- (also polymethin-), thiazol-, indamin-, indophenol-, azin-, oxazin, thiazin-, anthraquinone-, indigoid-, phtalocyanine- and further synthetic, natural and/or inorganic chromophores.

According to the instant invention, pigments of component (d) include inorganic pigments, metal oxides and hydroxides, mica, organic pigments, pearlescent pigments, mineral silicates, porous materials, carbons, interference pigments, and the like.

Examples of the inorganic pigments of component (d) capable of being utilized according to the present invention are ultramarine blue, ultramarine violet, Prussian blue, manganese violet, titanium-coated mica, bismuth oxychloride, iron oxides, iron hydroxide, titanium dioxide, titanium lower oxides, chromium hydroxide and oxides, and carbon based pigments (e.g. Carbon Black). Of these inorganic pigments, ultramarine blue and Prussian blue are particular advantageous.

According to the instant invention, the range of useful organic pigments of component (d) may comprise monoazo, disazo, naphthol, dioxazone, azomethin, azocondensation, metal complex, nitro, perinone, quinoline, anthraquinone, benzimidozolone, isoindoline, isoindolinone, triarylmethane, quinacridone, hydroxyanthraquinone, aminoanthraquinone, anthrapyrimidine, indanthrone, flavanthrone, pyranthrone, anthantrone, isoviolanthrone, diketopyrrolopyrrole, carbazole, indigo or thiolndigo pigments.

According to the instant invention, examples of the organic pigments of component (d) are C.I. 15850, C.I. 15850:1, C.I. 15585:1, C.I. 15630, C.I. 15880:1, C.I. 73360, C.I. 12085, C.I. 15865:2, C.I. 12075, C.I. 21110, C.I. 21095, and C.I. 11680, C.I. 74160 and zirconium, barium, or aluminum lakes of C.I. 45430, C.I. 45410, C.I. 45100, C.I. 17200, C.I. 45380, C.I. 45190, C.I. 14700, C.I. 15510, C.I. 19140, C.I. 15985, C.I. 45350, C.I. 47005, C.I. 42053, C.I. 42090.

C.I. means Colour Index as compiled by the by The Society of Dyers and Colourists and The American Association of Textile Chemists and Colourists.

According to the instant invention, mixtures of the organic pigments of component (d) may be used.

According to the instant invention, mixtures of the inorganic and organic pigments of component (d) may be used.

According to the instant invention, mixtures of dyes and organic and/or inorganic pigments of component (d) may be used.

Component (d) of the personal care compositions preferably comprise no more than about 10 weight percent of the composition; more preferably no more than about 7 weight percent of the personal care composition; even more preferably no more than about 5 weight percent; and still more preferably no more than about 3 weight percent. The component (d) of the personal care composition preferably comprise at least about 0.0001 weight percent of the personal care composition, more preferably at least about 0.01 weight percent, even more preferably at least about 0.1 weight percent, and still more preferably at least about 0.2 by weight of the composition.

Personal care compositions according to the invention may be generally applied to the skin and/or hair of humans and/or animals.

Another embodiment of the instant invention is a method for the conditioning treatment of mammalian keratin-containing fibers, wherein said method comprises contacting said fibers with an effective amount of a personal care composition or formulation comprising one or more cationic nanoparticles of formula (I).

Another embodiment of the instant invention is a method for the conditioning treatment of mammalian skin, wherein said method comprises contacting said skin with an effective amount of a personal care composition or formulation comprising one or more cationic nanoparticles of formula (I).

Another embodiment of the instant invention is a method for the antimicrobial treatment of mammalian keratin-containing fibers, wherein said method comprises contacting said fibers with an effective amount of a personal care composition or formulation comprising one or more cationic nanoparticles of formula (I).

Another embodiment of the instant invention is a method for the antimicrobial treatment of mammalian skin, wherein said method comprises contacting said skin with an effective amount of a personal care composition or formulation comprising one or more cationic nanoparticles of formula (I).

Another embodiment of the instant invention is a method for the manufacture of an antimicrobial personal care composition or formulation, wherein said method comprises incorporating into said personal care composition or formulation an effective antimicrobial amount of one or more cationic nanoparticles of formula (I).

Personal care compositions according to the invention may be contained in a wide variety of personal care preparations. Especially the following preparations, for example, come into consideration:

shaving preparations, e.g. shaving soap, foaming shaving creams, non-foaming shaving creams, foams and gels, preshave preparations for dry shaving, aftershaves or aftershave lotions;

skin-care preparations, e.g. skin emulsions, multi-emulsions or skin oils, body powders, hot-oil treatments, and exfoliating masques;

cosmetic personal care preparations, e.g. facial make-up in the form of lipsticks, eye shadow, eye liners, liquid make-up, day creams or powders, facial lotions, foundations, creams and powders (loose or pressed), hair removal systems;

light-protective preparations, such as sun tan lotions, creams and oils, sun blocks, pretanning preparations and sunless tanning preparations;

manicure preparations, e.g. nail polishes, nail enamels, enamel removers, nail treatments deodorants, e.g. deodorant sprays, pump-action sprays, deodorant gels, sticks or roll-ons;

antiperspirants, such as antiperspirant sticks, creams or roll-ons; and solid/liquid personal cleaning products, such as soap, cleansers, shampoo, conditioners, hair treatments.

Another embodiment of the instant invention is a personal care composition comprising said cationic nanoparticles of formula (I) which is formulated as a water-in-oil or oil-in-water emulsion, as an alcoholic or alcohol-containing formulation, as a vesicular dispersion of an ionic or non-ionic amphiphilic lipid, as a gel, or a solid stick as an aqueous or non-aqueous system.

Another embodiment of the instant invention is a personal care composition wherein the personal care or cosmetic composition additionally comprises a blend of pigment particles that are individually provided in a single matrix material.

The personal care compositions of the present invention may contain one or more additional skin care or hair care components. In a preferred embodiment, where the composition is to be in contact with human or animal keratinous tissue, the additional components should be suitable for application to keratinous tissue, that is, when incorporated into the composition they are suitable for use in contact with human or animal keratinous tissue without undue toxicity, incompatibility, instability, allergic response, and the like within the scope of sound medical judgment.

The instant compositions may further comprise, cosmetically acceptable ingredients and adjuvants of component (b) selected, in particular but not limited to, from among fatty substances, organic solvents, oil structurants, surfactants, emulsifiers, thickeners, organic cationic deposition polymers, demulcents, opacifiers, additional colorants colorants, effect pigments, additional stabilizers, emollients, antifoaming agents, moisturizing agents, antioxidants, vitamins, peptides, amino acids, botanical extracts, particulates, perfumes, preservatives, polymers, fillers, sequestrants, propellants, alkalinizing or acidifying agents or other optional ingredients customarily formulated into cosmetics or other personal care compositions according to the invention.

The fatty substances may be an oil or a wax or mixtures thereof, and they also comprise fatty acids, fatty alcohols and esters of fatty acids. The oils may be selected from among animal, vegetable, mineral or synthetic oils and, in particular, from among liquid paraffin, paraffin oil, silicone oils, volatile or otherwise, isoparaffins, polyolefins, fluorinated or perfluorinated oils. Likewise, the waxes may be animal, fossil, vegetable, mineral or synthetic waxes which are also known per se.

Exemplary organic solvents may include the lower alcohols and polyols.

Of course, one skilled in this art will take care to select this or these optional additional compounds and/or their quantities such that the advantageous properties, in particular the resistance to water, the stability, which are intrinsically associated with the sunscreen compositions in accordance with the invention are not, or not substantially, altered by the addition(s) envisaged.

The CTFA Cosmetic Ingredient Handbook, Second Edition (1992) describes a wide variety of non-limiting cosmetic and pharmaceutical ingredients commonly used in the personal care industry, which are suitable for use in the personal care compositions of the present invention.

The present invention may optionally comprise an oil structurant. The structurant can provide the dispersed phase with the correct rheological properties. This can aid in providing effective deposition and retention to the skin, the structured oil or oil phase should have a viscosity in the range of 100 to about 200,000 poise measured at 1 Sec-1, preferably 200 to about 100,000 poise, and most preferably 200 to about 50,000 poise. The amount of structurant required to produce this viscosity will vary depending on the oil and the structurant, but in general, the structurant will preferably be less than 75 weight percent of the dispersed oil phase, more preferably less than 50 weight percent, and still more preferably less than 35 weight percent of the dispersed oil phase.

The structurant can be either an organic or inorganic structurant. Examples of organic thickeners suitable for the invention are solid fatty acid esters, natural or modified fats, fatty acid, fatty amine, fatty alcohol, natural and synthetic waxes, and petrolatum, and the block copolymers sold under the name KRATON by Shell. Inorganic structuring agents include hydrophobically modified silica or hydrophobically modified clay. Nonlimiting examples of inorganic structurants are BENTONE 27V, BENTONE 38V or BENTONE GEL MIO V from Rheox; and CAB-O-SIL TS720 or CAB-O-SIL M5 from Cabot Corporation.

Structurants meeting the above requirements with the selected skin compatible oil can form 3-dimensional network to build up the viscosity of the selected oils. It has been found that such structured oil phases, i.e., built with the 3-dimensional network, are extremely desirable for use as wet-skin treatment compositions used in bathing. These structured oils can deposit and be retained very effectively on wet skin and retained after rinsing and drying to provide long-lasting after wash skin benefit without causing a too oily/greasy wet and dry feel. It is believed that the highly desirable in-use and after-use properties of such structured oils are due to their shear thinning rheological properties and the weak structure of the network. Due to its high low-shear viscosity, the 3-dimensional network structured oil can stick and retain well on the skin during application of the skin conditioner. After being deposited on the skin, the network yields easily during rubbing due to the weak structuring of the crystal network and its lower high-shear viscosity.

A wide variety of surfactants can be useful herein, both for emulsification of the dispersed phase as well as to provide acceptable spreading and in use properties for non-lathering systems. For cleansing applications, the surfactant phase also serves to clean the skin and provide an acceptable amount of lather for the user. The composition preferably contains no more than about 50 weight percent of a surfactant, more preferably no more than about 30 weight percent, still more preferably no more than about 15 weight percent, and even more preferably no more than about 5 weight percent of a surfactant. The composition preferably contains at least about 5 weight percent of a surfactant, more preferably at least about 3 weight percent, still more preferably at least about 1 weight percent, and even more preferably at least about 0.1 weight percent of a surfactant. For cleansing applications the personal care compositions preferably produces a Total Lather Volume of at least 300 ml, more preferably greater than 600 ml as described in the Lathering Volume Test. The personal care compositions preferably produces a Flash Lather Volume of at least 100 ml, preferably greater than 200 ml, more preferably greater than 300 ml as described in the Lathering Volume Test.

Preferable surfactants useful in the personal care compositions of the instant invention include those selected from the group consisting of anionic surfactants, nonionic surfactants, amphoteric surfactants, non-lathering surfactants, emulsifiers and mixtures thereof. Non-limiting examples of surfactants useful in the compositions of the present invention are disclosed in U.S. Pat. No. 6,280,757, to McAtee et al., issued Aug. 28, 2001, herein incorporated by reference.

Non-limiting examples of anionic surfactants useful in the personal care compositions of the present invention are disclosed in McCutcheon's, Detergents and Emulsifiers, North American edition (1986), published by Allured Publishing Corporation; McCutcheon's, Functional Materials, North American Edition (1992); and U.S. Pat. No. 3,929,678, to Laughlin et al., issued Dec. 30, 1975, herein incorporated by reference.

A wide variety of anionic surfactants are useful herein. Non-limiting examples of anionic surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are fatty acid soaps (i.e., alkali metal salts, e.g., sodium or potassium salts) typically having from a fatty acid having about 8 to about 24 carbon atoms, preferably from about 10 to about 20 carbon atoms. These fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps and their preparation are described in detail in U.S. Pat. No. 4,557,853, herein incorporated by reference.

Other anionic materials include phosphates such as monoalkyl, dialkyl, and trialkylphosphate salts. Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein are ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Non-limiting examples of nonionic surfactants for use in the personal care compositions of the present invention are disclosed in McCutcheon's, Detergents and Emulsifiers, North American edition (1986), published by Allured Publishing Corporation; and McCutcheon's, Functional Materials, North American Edition (1992), herein incorporated by reference.

Nonionic surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Non-limiting examples of preferred nonionic surfactants for use herein are those selected from the group consisting of C8-C14 glucose amides, C8-C14 alkyl polyglucosides, sucrose cocoate, sucrose laurate, lauramine oxide, cocoamine oxide and mixtures thereof.

The term "amphoteric surfactant," as used herein, is also intended to encompass zwitterionic surfactants, which are well known to formulators skilled in the art as a subset of amphoteric surfactants.

A wide variety of amphoteric lathering surfactants can be used in the personal care compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American edition (1986), published by Allured Publishing Corporation; and McCutcheon's, Functional Materials, North American Edition (1992), herein incorporated by reference.

Non-limiting examples zwitterionic surfactants are those selected from the group consisting of betaines, sultaines, hydroxysultaines, alkyliminoacetates, iminodialkanoates, aminoalkanoates, and mixtures thereof.

Preferred surfactants for use herein are the following, wherein the anionic surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the non-ionic surfactant is selected from the group consisting of lauramine oxide, cocoamine oxide, decyl polyglucose, lauryl polyglucose, sucrose cocoate, C12-14 glucosamides, sucrose laurate, and mixtures thereof; and wherein the amphoteric surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

A wide variety of non-lathering surfactants are useful herein. The personal care compositions of the present invention can comprise a sufficient amount of one or more non-lathering surfactants to emulsify the dispersed phase to yield an appropriate particle size and good application properties on wet skin.

Nonlimiting examples of these non-lathering compositions are: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

In addition, there are several commercial emulsifier mixtures that are useful in some embodiments of the personal care compositions according to the present invention. Examples include PROLIPID 141 (glyceryl stearate, behenyl alcohol, palmitic acid, stearic acid, lecithin, lauryl alcohol, myristyl alcohol and cetyl alcohol) and 151 (Glyceryl stearate, cetearyl alcohol, stearic acid, 1-propanamium, 3-amino-N-(2-(hydroxyethyl-)-N—N-Dimethyl, N—C(16-18) Acyl Derivatives, Chlorides) from ISP; POLAWAX NF (Emulsifying wax NF), INCROQUAT BEHENYL TMS (behentrimonium sulfate and cetearyl alcohol) from Croda; and EMULLIUM DELTA (cetyl alcohol, glyceryl stearate, PEG-75 stearate, ceteth-20 and steareth-20) from Gattefosse.

The personal care compositions of the present invention, in some embodiments, may further include one or more thickening/aqueous phase stability agents. Because different stability agents thicken with different efficiencies, it is difficult to provide an accurate compositional range, however, when present, the composition preferably comprises no more than about 20 weight percent, more preferably no more than about 10 weight percent, more preferably no more than about 8 weight percent, and still more preferably no more than about 7 weight percent of the personal care composition. When present, the thickening/aqueous phase stability agent preferably comprises at least about 0.01 weight percent, more preferably at least about 0.05 weight percent, and still more preferably at least about 0.1 weight percent of the personal care composition. A better method of describing the stability agent is to say that it must build viscosity in the product. This can be measured using the Stability Agent Viscosity Test; preferably, the stability agent produces a viscosity in this test of at least 1000 cps, more preferably at least 1500 cps, and still more preferably at least 2000 cps.

Nonlimiting examples of thickening agents useful herein include carboxylic acid polymers such as the carbomers (such as those commercially available under the trade name CARBOPOL® 900 series from B.F. Goodrich; e.g., CARBOPOL® 954). Other suitable carboxylic acid polymeric agents include copolymers of C10-30 alkyl acrylates with one or more monomers of acrylic acid, methacrylic acid, or one of their short chain (i.e., C1-4 alcohol) esters, wherein the cross linking agent is an allyl ether of sucrose or pentaerytritol. These copolymers are known as acrylates/C10-30 alkyl acrylate crosspolymers and are commercially available as CARBOPOL® 1342, CARBOPOL® (1382, PEMULEN TR-1, and PEMULEN TR-2, from B.F. Goodrich.

Other nonlimiting examples of thickening agents include crosslinked polyacrylate polymers including both cationic and nonionic polymers.

Still other nonlimiting examples of thickening agents include the polyacrylamide polymers, especially nonionic polyacrylamide polymers including substituted branched or unbranched polymers. More preferred among these polyacrylamide polymers is the nonionic polymer given the CTFA designation polyacrylamide and isoparaffin and laureth-7, available under the Trade name SEPIGEL 305 from Seppic Corporation (Fairfield, N.J.). Other polyacrylamide polymers useful herein include multi-block copolymers of acrylamides and substituted acrylamides with acrylic acids and substituted acrylic acids. Commercially available examples of these multi-block copolymers include HYPAN SR150H, SS500V, SS500W, SSSA100H, from Lipo Chemicals, Inc., (Patterson, N.J.).

Another nonlimiting class of thickening agents useful herein is the polysaccharides. Nonlimiting examples of polysaccharide gelling agents include those selected from cellulose, and cellulose derivatives. Preferred among the alkyl hydroxyalkyl cellulose ethers is the material given the CTFA designation cetyl hydroxyethylcellulose, which is the ether of cetyl alcohol and hydroxyethylcellulose, sold under the trade name NATROSEL® CS PLUS from Aqualon Corporation (Wilmington, Del.). Other useful polysaccharides include scleroglucans which are a linear chain of (1-3) linked glucose units with a (1-6) linked glucose every three units, a commercially available example of which is CLEAROGEL™ CS 11 from Michel Mercier Products Inc. (Mountainside, N.J.).

Another nonlimiting class of thickening agents useful herein is the gums. Nonlimiting examples of gums useful herein include hectorite, hydrated silica, xantham gum, cellulose gums, guar gum, biosaccharide gums and mixtures thereof.

Yet another nonlimiting class of thickening agents useful herein is the modified starches. Acrylate modified starches such as WATERLOCK® from Grain Processing Corporation may be used. Hydroxypropyl starch phosphate, tradename STRUCTURE XL from National Starch is another example of a useful modified starch, and other useful examples include ARISTOFLEX HMB (Ammonium Acrylodimethyltaruate/Beheneth-25 Methacrylate Crosspolymer) from Clariant and cationic stabylens.

The personal care compositions according to the present invention may also contain organic cationic deposition polymers. Concentrations of the cationic deposition polymers preferably range from about 0.025% to about 10%, more preferably from about 0.05% to about 2%, even more preferably from about 0.1% to about 1%, by weight of the personal care composition.

Suitable cationic deposition polymers for use in the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the personal care composition. The average molecular weight of the cationic deposition polymer is between about 5,000 to about 10 million, preferably at least about 100,000, more preferably at least about 200,000, but preferably not more than about 2 million, more preferably not more than about 1.5 million. The polymers also have a cationic charge density ranging from about 0.2 meq/gm to about 5 meq/gm, preferably at least about 0.4 meq/gm, more preferably at least about 0.6 meq/gm, at the pH of intended use of the personal care composition, which pH will generally range from about pH 4 to about pH 9, preferably between about pH 5 and about pH 8.

Nonlimiting examples of cationic deposition polymers for use in the personal care compositions include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their POLYMER KG, JR and LR series of polymers with the most preferred being KG-30M.

Other suitable cationic deposition polymers include cationic guar gum derivatives, such as guar hydroxypropyltrimonium chloride, specific examples of which include the Jaguar series (preferably JAGUAR C-17) commercially available from Rhodia Inc., and N-HANCE polymer series commercially available from Aqualon.

Other suitable cationic deposition polymers include synthetic cationic polymers. The cationic polymers suitable for use in the personal cleansing composition herein are water soluble or dispersible, non cross linked, cationic polymers having a cationic charge density of from about 4 meq/gm to about 7 meq/gm, preferably from about 4 meq/gm to about 6 meq/gm, more preferably from about 4.2 meq/gm to about 5.5 meq/gm. The select polymers also must have an average molecular weight of from about 1,000 to about 1 million, preferably from about 10,000 to about 500,000, more preferably from about 75,000 to about 250,000.

A non limiting example of a commercially available synthetic cationic polymer for use in the cleansing compositions is polymethyacrylamidopropyl trimonium chloride, available under the trade name POLYCARE 133, from Rhodia, Cranberry, N.J., U.S.A.

Other non limiting examples of optional ingredients include benefit agents that are selected from the group consisting of vitamins and derivatives thereof (e.g., ascorbic acid, vitamin E, tocopheryl acetate, and the like); sunscreens; thickening agents (e.g., polyol alkoxy ester, available as CROTHIX from Croda); preservatives for maintaining the anti microbial integrity of the cleansing compositions; anti-acne medicaments (resorcinol, salicylic acid, and the like); antioxidants; skin soothing and healing agents such as aloe vera extract, allantoin and the like; chelators and sequestrants; and agents suitable for aesthetic purposes such as fragrances, essential oils, skin sensates, pigments, pearlescent agents (e.g., mica and titanium dioxide), lakes, colorings, and the like (e.g., clove oil, menthol, camphor, eucalyptus oil, and eugenol), antibacterial agents and mixtures thereof. These materials can be used at ranges sufficient to provide the required benefit, as would be obvious to one skilled in the art.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

EXAMPLE 1

3-Iodopropylsilane Modified Silica Nanoparticles

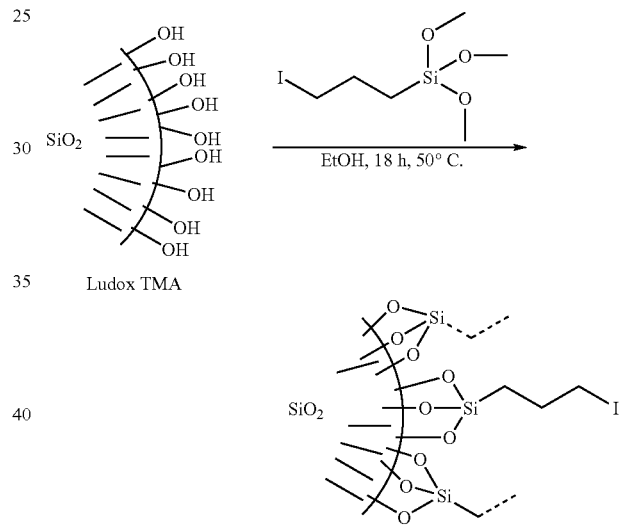

An aqueous dispersion of Ludox TMA (33.4 g, 34% nanosilica dispersion in water, Helm AG) is mixed with 190 ml ethanol in a laboratory flask with appropriate auxiliary equipment. 3-iodopropyl-trimethoxysilane (25 g, Fluka, purum) is added drop wise during 45 minutes at ambient temperature to this stirred dispersion. After the addition is complete, the mixture is heated to 50 C for 18 hours. After cooling to room temperature, the dispersion is extracted twice with 300 ml hexane to remove all unreacted 3-iodopropyl-trimethoxysilane and than 75% of the ethanolic phase is evaporated in the rotary evaporator. The concentrate is re-dispersed in 120 ml ethanol and a white resin is obtained. The product is re-dispersed in 50 ml ethanol to obtain 123.1 g of a yellow dispersion with a solid content of 24 percent by weight. Thermographimetric analysis (TGA) (heating rate: 10 C/min from 50 C to 800 C) gives a weight loss of 46.6 percent, corresponding to the amount of organic material covalently attached to the silica nanoparticles. Elemental analysis of the modified silica nanoparticles is found: C 11.58%, H 2.12%, I 31.69%: which corresponds to an organic content of about 50 percent which is in good agreement with the TGA analysis. Particle size analysis is done by dynamic light scattering (DLS) and the average particle size is 37 nm.

EXAMPLE 2

N,N-Dimethyl-N-Dodecylammonium-Iodide-N-Propylsilane Modified Silica Nanoparticles

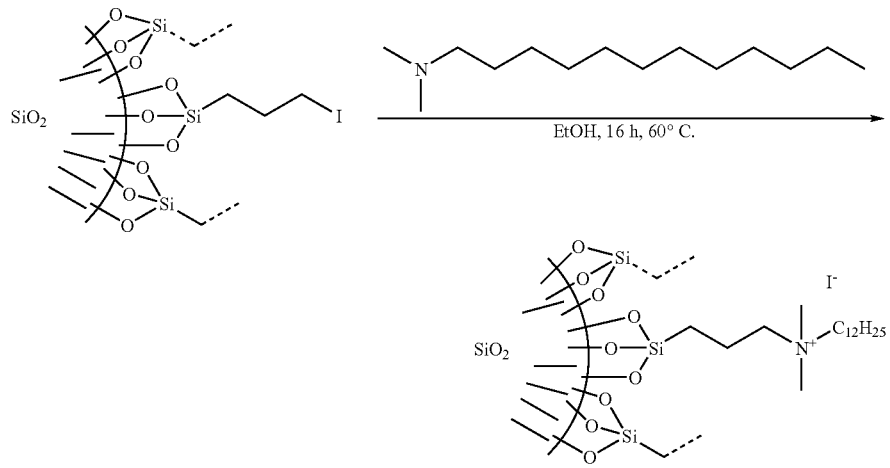

The ethanolic dispersion of Instant Example 1 (10 g, iodo content: 0.76 g or 6 mmol) is mixed with N,N-dimethylaminododecane (1.28 g, 6 mmol, Fluka, purum) and heated to 60 C for 16 hours. Over the course of the reaction, the reaction mass color becomes white. After cooling, all solvent is evaporated in a rotary evaporator to obtain 3.26 g of the title compound as a white solid. Thermographimetric analysis (TGA) (heating rate: 10° C./min from 50 C to 800 C) gives a weight loss of 66.0 percent, corresponding to the organic material. This is in good agreement with the theoretical value of 66.8 percent. The product is re-dispersed in ethanol to obtain a dispersion with a solid content of 10 percent by weight. Particle size analysis is done by dynamic light scattering (DLS) and the average particle size is 214.9 nm.

EXAMPLE 3

N,N-Dimethyl-N-Dodecylammonium-Chloride-N-Propylsilane Modified Organic Polymeric Nanoparticles

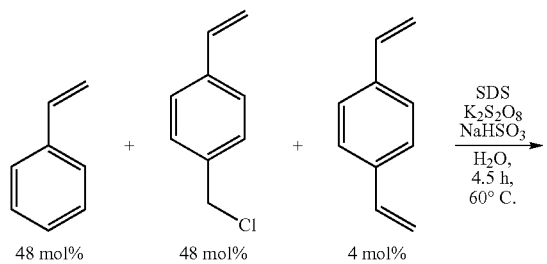

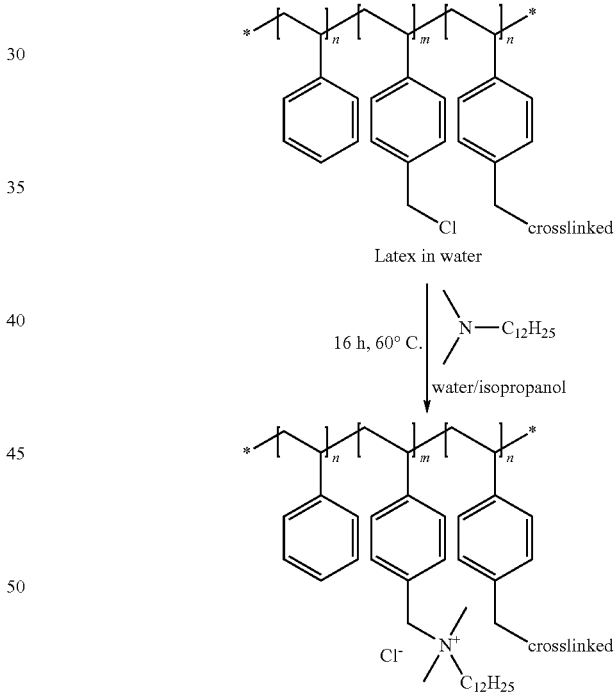

In a 1 L round bottom flask with mechanical stirring, sodiumdodecylsulfate (5.15 g, SDS, Fluka techn.) and 385 ml water are introduced and purged with nitrogen for 30 minutes. A mixture of styrene (50.02 g, 0.48 mol, Fluka, purum), 4-chloromethyl styrene (73.25 g, 0.48 mol, Fluka technical) and 5.20 g (0.04 mol) divinylbenzene (5.20 g, 0.04 mol, Fluka technical) is made separately and 15 ml of this mixture is added into the reactor. After homogenization by stirring during 1 hour under $N_2$, 10 ml of a 5% aqueous solution of potassium peroxodisulfate (KPS; Fluka puriss p.a.) and 0.16 g of a sodium hydrogensulfite (40% solution in water) solution is added and the emulsion is heated with an oil bath to 60

C for 10 minutes. At this point, the rest of the monomer mixture is added drop wise over 1.5 hours. After that, a second portion of 10 ml of a 5% aqueous solution of potassium peroxodisulfate (KPS) and 0.16 g of sodium hydrogensulfite solution (40% in water) and polymerization continued at 60 C for 3 hours. A polymeric white emulsion (492.3 g) is obtained after cooling. Particle size is done by dynamic light scattering (DLS) and the average particle size is 87.2 nm. The solid content of the polymeric emulsion (graphimetric analysis after coagulation by precipitation in 10% aqueous $MgSO_4$ solution and drying) is determined to be 18.2 percent by weight.

| Elemental analysis: | Cl content: | calculated: | 13.3 percent |
|---|---|---|---|
| | | found: | 12.2 percent |

In a 1 L round bottom flask with a mechanical stirrer, the polymeric emulsion (100 g) described above, water (190 g) and isopropanol (74 g) are added and the mixture is stirred at room temperature. N,N-dimethylaminododecane (13.34 g, 62.5 mmol, Fluka, purum), dissolved in 30 g isopropanol/water (2:1 ratio by weight), is added drop wise over 1 hour. The mixture is then heated to 60 C for 16 hours. The title product is obtained as a white homogeneous emulsion. Particle size analysis is done by dynamic light scattering (DLS) and the average particle size is 120.9 nm.

EXAMPLE 4

3-Aminopropylsilane Modified Silica Nanoparticles

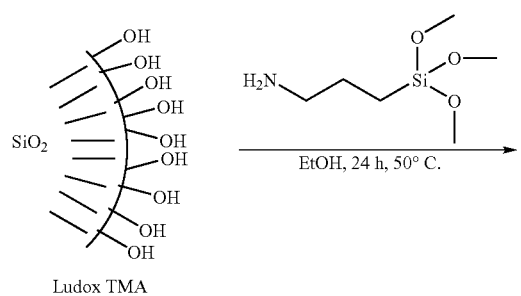

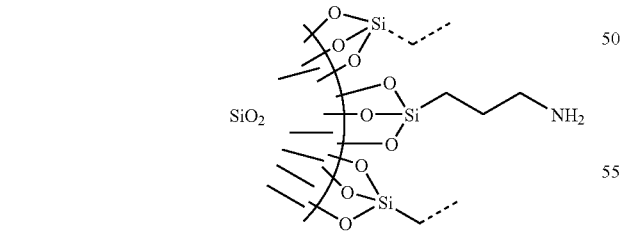

An aqueous dispersion of Ludox TMA (510 g, 34% nano-silica dispersion in water, Helm AG) is mixed with ethanol (1933.3 g) in a 5-L laboratory flask with appropriate auxiliary equipment. 3-aminopropyl-trimethoxysilane (345 g, Aldrich) is added drop wise during 120 minutes at ambient temperature to this stirred dispersion. After the addition is complete, the mixture is heated to 50 C for 24 hours. After the reaction hold period, about 50% of the ethanolic phase is evaporated in a rotary evaporator. The concentrate (1278.6 g) is obtained a yellowish-white dispersion with a solid content of 29.8 percent by weight.

EXAMPLE 5

Quaternarized Ammonium Functioned Modified Silica Nanoparticles

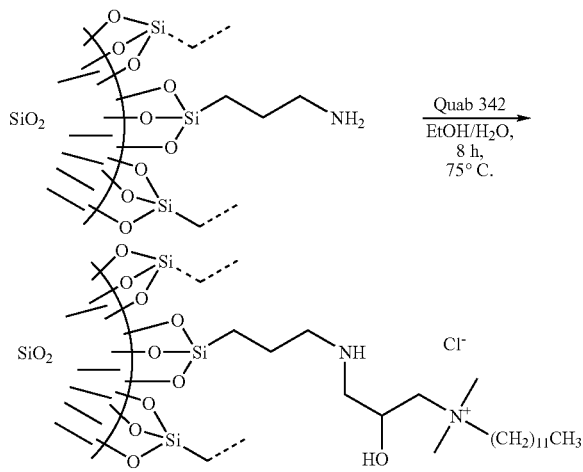

The 3-aminopropylsilane modified silica nanoparticles of Instant Example 4 (100 g, 29.8% solids) are placed into a round-bottomed flask equipped with a stirrer, nitrogen inlet and a thermoregulator and heated. When the temperature reaches 75 C, of 3-chloro-2-hydroxypropyl-dimethyldodecy-lammonium chloride (19.8 g, 21.96 mmol, 38% solids, QUAB 342, Degussa) is added over 4 hours to the reaction flask. After the addition, the reaction temperature is maintained at 75 C for four hours with stirring. At this time, the consumption of QUAB 342 is determined to be complete by High Pressure Liquid Chromatographic (HPLC) analysis. After the analysis is complete, the mixture is cooled to room temperature and deionized water (51.02 g) is added to reduce viscosity. The quaternarized ammonium functionalized modified silica nanoparticles are obtained as a bluish-white emulsion having a solids content of 23.0 percent by weight.

EXAMPLE 6

Tertiary-Amide Functioned Modified Silica Nanoparticles

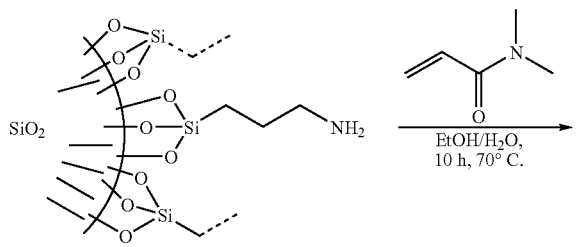

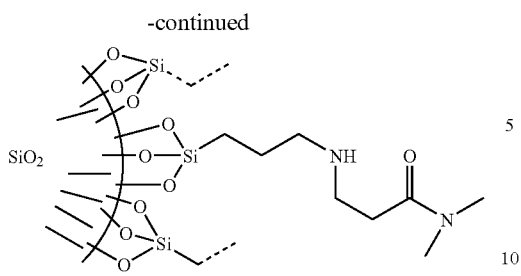

The 3-aminopropylsilane modified silica nanoparticles of Instant Example 4 (40.2 g, 29.8% solids) are placed into a round-bottomed flask equipped with a stirrer, nitrogen inlet and a thermoregulator and heated. When the temperature reaches 70 C, N,N-dimethylacrylamide (3.7 g, 37 mmol, Ciba) is added over 1 hour to the reaction flask. After the addition, the reaction mixture is maintained at 70 C for nine hours with stirring. At this time, the consumption of N,N-dimethylacrylamide is determined to be 97.3 percent by Gas Chromatographic (GC) analysis of the reaction liquor. The tertiary-amide functionalized modified silica nanoparticles are obtained as a white emulsion having a solids content of 31.8 percent by weight.

EXAMPLE 7

Amide Functioned Modified Silica Nanoparticles

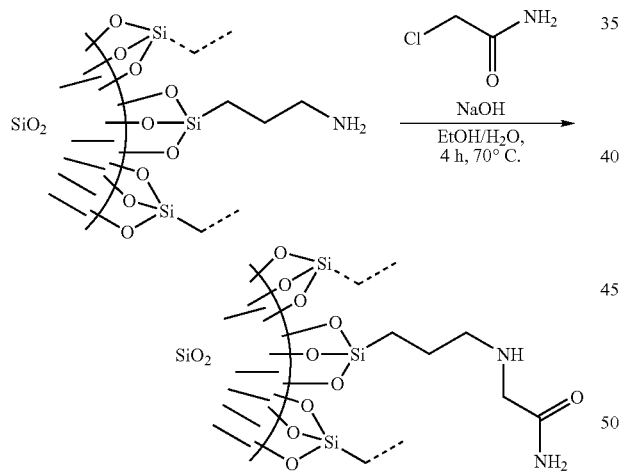

The 3-aminopropylsilane modified silica nanoparticles of Instant Example 4 (40.5 g, 29.8% solids) are placed into a round-bottomed flask equipped with a stirrer, nitrogen inlet and a thermoregulator and heated. When the temperature reaches 70 C, 2-chloroacetamide (13.3 g, 0.14 mol, Aldrich) is added over 5 minutes to the reaction flask. After the addition, the reaction mixture is maintained at 70 C for four hours with stirring and the pH of the reaction mass is maintained at 10 with 50% NaOH (15.6 g total). The reaction is determined to be complete when the pH no longer decreased. The mixture is cooled to room temperature and 20.8 g of deionized water and 3.3 g of ethanol are added to decrease turbidity. The amide functionalized modified silica nanoparticles are obtained as a white slightly turbid emulsion having a solids content of 27.2 percent by weight.

EXAMPLE 8

Tertiary-Amide Functioned Modified Silica Nanoparticles

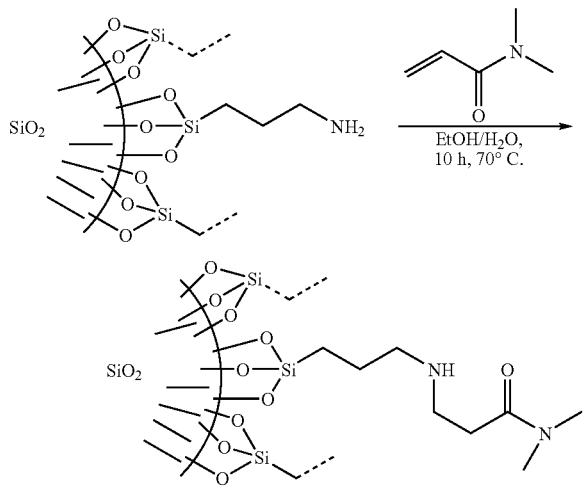

The 3-aminopropylsilane modified silica nanoparticles of Instant Example 4 (42 g, 29.8% solids) are placed into a round-bottomed flask equipped with a stirrer, nitrogen inlet and a thermoregulator and heated. When the temperature reaches 70 C, N,N-dimethylacrylamide (5.5 g, 55 mmol, Ciba) is added over 1 hour to the reaction flask. After the addition, the reaction mixture is maintained at 70 C for nine hours with stirring. At this time, the consumption of N,N-dimethylacrylamide is determined to be 94.4 percent by Gas Chromatographic (GC) analysis of the reaction liquor. Some of the ethanol and water is distilled off and replaced with deionized water (29 g). The reaction mass is cooled and discharged. The tertiary-amide functionalized modified silica nanoparticles are obtained as a white emulsion having a solids content of 33.1 percent by weight.

EXAMPLE 9

Phenoxy Functionalized Modified Silica Nanoparticles

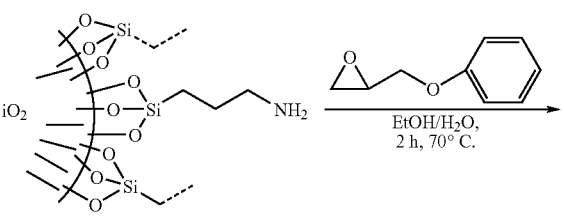

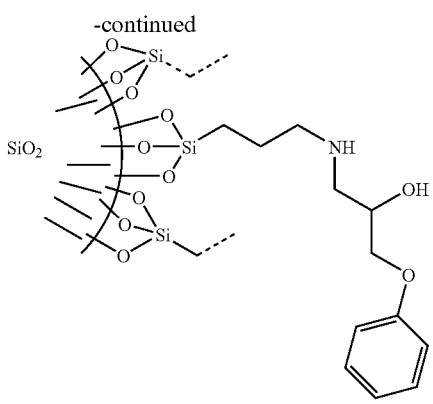

The 3-aminopropylsilane modified silica nanoparticles of Instant Example 4 (40.5 g, 29.8% solids) are placed into a round-bottomed flask equipped with a stirrer, nitrogen inlet and a thermoregulator and heated. When the temperature reaches 70 C, phenylglycidylether (10.5 g, 69.9 mmol, Aldrich) is added over 1 hour to the reaction flask. After the addition and the exotherm are complete, the reaction mixture is maintained at 70 C for two hours with stirring. At this time, the consumption of phenylglycidyl ether is determined to be 100 percent by Gas Chromatographic (GC) analysis of the reaction liquor. Some of the ethanol and water are distilled off and replaced with 22.7 g of ethanol. The reaction mass is cooled and discharged. The phenoxy-functionalized modified silica nanoparticles are obtained as a bluish-white transparent emulsion having a solids content of 30.6 percent by weight.

EXAMPLE 10

Phenoxy Functionalized Modified Silica Nanoparticles

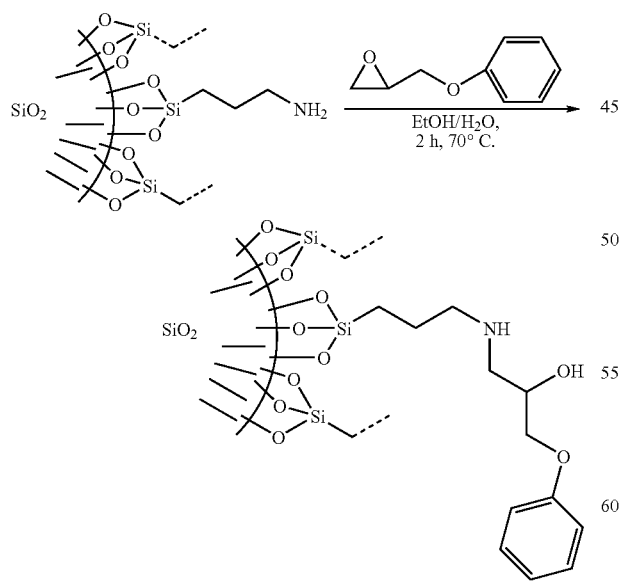

The 3-aminopropylsilane modified silica nanoparticles of Instant Example 4 (81 g, 29.8% solids) are placed into a round-bottomed flask equipped with a stirrer, nitrogen inlet and a thermoregulator and heated. When the temperature reaches 70 C, phenylglycidylether (10.5 g, 69.9 mmol, Aldrich) is added over 1 hour to the reaction flask. After the addition and the exotherm are complete, the reaction mixture is maintained at 70 C for two hours with stirring. At this time, the consumption of phenylglycidyl ether is determined to be 100 percent by Gas Chromatographic (GC) analysis of the reaction liquor. The reaction mass is cooled and discharged. The phenoxy-functionalized modified silica nanoparticles are obtained as a bluish-white transparent emulsion having a solids content of 37.9 percent by weight.

EXAMPLE 11

1-Methyl-3-Benzyl-Imidazolium-Chloride Modified Organic Polymeric Nanoparticles

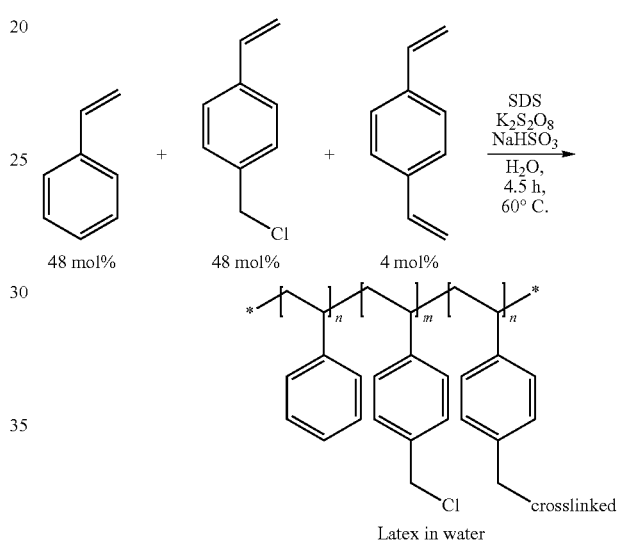

The first part, formation of a crosslinked latex of styrene and 4-chloromethyl styrene, is as described in Example 3.

In a 0.75 L round bottom flask with a mechanical stirrer, the polymeric emulsion (116 g) described above, water (190 g) and isopropanol (74 g) are added and the mixture is stirred at room temperature. 1-Methyl-imidazol (5.95 g, 72.5 mmol, Fluka, puriss p.a.), dissolved in 30 g isopropanol/water (2:1 ratio by weight), is added drop wise over 1 hour. The mixture is then heated to 60 C for 16 hours, followed by 2 hours in an ultrasound bath with continuous stirring. The title product is obtained as a white homogeneous emulsion. Particle size analysis is done by dynamic light scattering (DLS) and the average particle size is 388.1 nm.

EXAMPLE 12

Antimicrobial Applications Testing Using *Escherichia Coli*

The cationic nanoparticles of the instant invention are tested for in vitro bactericidal activity by the Suspension Test. This test method is used to determine the bactericidal activity of substances in solution or formulations, i.e. the ability of a product to achieve a reduction in the number of viable bacteria cells of relevant organisms according to the modified conditions defined in European Standard Method EN 1040.

An appropriate volume of test formulation or solution with solubilized or homogenously suspended test substances is inoculated with a suspension of bacteria cells. After specified contact times, aliquots are taken, inactivated and diluted. The number of surviving cells in each sample is determined by surface plate-count method.

The compounds of invention are tested at a concentration of 1% (10,000 ppm) and 0.1% (1000 ppm) against *Escherichia coli* ATCC 10,536. The number of surviving bacteria cells per milliliter of assay is determined by counting the cfu/mL (colony forming unit/milliliter) on the agar plates and calculating the dilution steps. The difference of the surviving cells determined in the assay containing test substance and the surviving bacteria in the water reference is given as log reduction. The minimal cell count reduction is given as <1 and the maximum cell count reduction as >5.

To test the sensitivity of the inoculum, an antibacterial benchmark is tested in the same way as the test samples. As a benchmark, the following compound is used: Benzalkonium chloride (Alkylbenzyldimethylammonium chloride, CAS No.: 63449-41-2, Fluka): test concentration for *E. coli* is 7 ppm.

Test Principle:

1 g stock solution with an appropriate concentration of test products are mixed with 8 g water and then inoculated with 1 ml of the selected test organisms. After a given contact period, aliquots are taken, inactivated and diluted. The number of surviving bacteria per ml incubation assay is determined by plate count. Proper inactivation by the inactivating medium used was checked each time.

Diluent: tryptone water for microorganisms
(0.1% tryptone (Oxoid L42), 0.85% NaCl, deionized water)
deionized water for test substances
inactivating medium for detection of surviving microorganisms
Growth medium: casein soybean peptone agar (Merck)
Inactivating Medium: tryptic soy broth special
(10% w/w Tween 80, 3% w/w Lecithine, 0.1% w/w L-Histidine, 0.055% w/w Sodium thiosulfate)
Test organisms: *Escherichia coli* ATCC 10536
Test concentration: 10,000 ppm
Contact times: 5 and 30 minutes at 22° C.
Incubation time: 24 h at 37° C.
Log Reduction: The Log Reduction in bacterial growth is calculated according to the following equation:

Log Reduction=log [water blank, cfu/mL]−log [sample, cfu/mL]

Microbiocidal activity of Cationic Nanoparticles [log reduction] at 10,000 ppm concentration:

| Sample | E. coli cfu/mL | Log Reduction 5 minutes | Log Reduction 30 minutes |
|---|---|---|---|
| inoculum | 3.13E+08 | — | — |
| water blank | 1.34E+07* | 0 | — |
| water blank | 1.34E+07** | — | 0 |
| Example 1 | 0.00E+00 | >5 | — |
| Example 1 | 0.00E+00 | — | >5 |
| Example 2 | 0.00E+00 | >5 | — |
| Example 2 | 0.00E+00 | — | >5 |
| Example 3 | 0.00E+00 | >5 | — |
| Example 3 | 0.00E+00 | — | >5 |
| Example 11 | 3.25E+05 | 1.6 | — |
| Example 11 | 2.85E+03 | — | 3.7 |

*The number of surviving bacteria cells per milliliter of assay five minutes after treatment with water blank.
**The number of surviving bacteria cells per milliliter of assay thirty minutes after treatment with water blank.

The cationic nanoparticles of the instant invention showed excellent activity against the gram-negative strain. For both strains, a log reduction of >5 is found, which demonstrates excellent antimicrobial activity.

EXAMPLE 13

Antimicrobial Applications Testing Using *Staphylococcus Aureus*

The cationic nanoparticles of the instant invention are tested for in vitro bactericidal activity by the Suspension Test. This test method is used to determine the bactericidal activity of substances in solution or formulations, i.e. the ability of a product to achieve a reduction in the number of viable bacteria cells of relevant organisms according to the modified conditions defined in European Standard Method EN 1040.

An appropriate volume of test formulation or solution with solubilized or homogenously suspended test substances is inoculated with a suspension of bacteria cells. After specified contact times, aliquots are taken, inactivated and diluted. The number of surviving cells in each sample is determined by surface plate-count method.

The compounds of invention are tested at a concentration of 1% (10,000 ppm) and 0.1% (1000 ppm) against *Staphylococcus aureus* ATCC 6538. The number of surviving bacteria cells per milliliter of assay is determined by counting the cfu/mL (colony forming unit/milliliter) on the agar plates and calculating the dilution steps. The difference of the surviving cells determined in the assay containing test substance and the surviving bacteria in the water reference is given as log reduction. The minimal cell count reduction is given as <1 and the maximum cell count reduction as >5.

To test the sensitivity of the inoculum, an antibacterial benchmark is tested in the same way as the test samples. As a benchmark, the following compound is used: Benzalkonium chloride (Alkylbenzyldimethylammonium chloride, CAS No.: 63449-41-2, Fluka): test concentration for *S. aureus* is 10 ppm.

Test Principle:

1 g stock solution with an appropriate concentration of test products are mixed with 8 g water and then inoculated with 1 ml of the selected test organisms. After a given contact period, aliquots are taken, inactivated and diluted. The number of surviving bacteria per ml incubation assay is determined by plate count. Proper inactivation by the inactivating medium used was checked each time.

Diluent: tryptone water for microorganisms
(0.1% tryptone (Oxoid L42), 0.85% NaCl, deionized water)
deionized water for test substances
inactivating medium for detection of surviving microorganisms
Growth medium: casein soybean peptone agar (Merck)
Inactivating Medium: tryptic soy broth special
(10% w/w Tween 80, 3% w/w Lecithine, 0.1% w/w L-Histidine, 0.055% w/w Sodium thiosulfate)
Test organisms: *Staphylococcus aureus* ATCC 6538
Test concentration: 10,000 ppm
Contact times: 5 and 30 minutes at 22° C.
Incubation time: 24 h at 37° C.
Microbiocidal activity of Cationic Nanoparticles [log reduction] at 10,000 ppm concentration:

| Sample | *S. aureus* cfu/mL | Log Reduction 5 minutes | Log Reduction 30 minutes |
|---|---|---|---|
| inoculum | 1.35E+08 | — | — |
| water blank | 3.17E+07* | 0 | — |
| water blank | 1.66E+07** | — | 0 |
| Example 1 | 0.00E+00 | >5 | — |
| Example 1 | 0.00E+00 | — | >5 |
| Example 2 | 0.00E+00 | >5 | — |
| Example 2 | 0.00E+00 | — | >5 |
| Example 3 | 0.00E+00 | >5 | — |
| Example 3 | 0.00E+00 | — | >5 |

*The number of surviving bacteria cells per milliliter of assay five minutes after treatment with water blank.
**The number of surviving bacteria cells per milliliter of assay thirty minutes after treatment with water blank.

The cationic nanoparticles of the instant invention showed excellent activity against the gram-positive and the gram-negative strain.

EXAMPLE 14

Antimicrobial Applications Testing Using *Escherichia Coli*

Following the procedure of Instant Example 11, the cationic nanoparticles of the instant invention are tested for antimicrobial activity against *E. coli* at a concentration of 1000 ppm.
Microbiocidal activity of Cationic Nanoparticles [log reduction] at 1000 ppm concentration:

| Sample | *E. coli* cfu/mL | Log Reduction 5 minutes | Log Reduction 30 minutes |
|---|---|---|---|
| inoculum | 1.77E+08 | — | — |
| water blank | 1.70E+07* | 0 | — |
| water blank | 1.81E+07** | — | 0 |
| Example 2 | 0.00E+00 | >5 | — |
| Example 2 | 0.00E+00 | — | >5 |
| Example 3 | 0.00E+00 | >5 | — |
| Example 3 | 0.00E+00 | — | >5 |

*The number of surviving bacteria cells per milliliter of assay five minutes after treatment with water blank.
**The number of surviving bacteria cells per milliliter of assay thirty minutes after treatment with water blank.

The cationic nanoparticles of the instant invention showed excellent activity against the gram-positive and the gram-negative strain. For both strains, a log reduction of >5 is found, which demonstrates excellent antimicrobial activity.

EXAMPLE 15

Antimicrobial Applications Testing Using *Staphylococcus Aureus*

Following the procedure of Instant Example 12, the cationic nanoparticles of the instant invention are tested for antimicrobial activity against *S. aureus* at a concentration of 1000 ppm.
Microbiocidal activity of Cationic Nanoparticles [log reduction] at 1000 ppm concentration:

| Sample | *S. aureus* cfu/mL | Log Reduction 5 minutes | Log Reduction 30 minutes |
|---|---|---|---|
| inoculum | 1.16E+08 | — | — |
| water blank | 1.66E+07* | 0 | — |
| water blank | 1.48E+07** | — | 0 |
| Example 2 | 1.02E+02 | >5 | — |
| Example 2 | 0.00E+00 | — | >5 |
| Example 3 | 2.34E+03 | 3.9 | — |
| Example 3 | 0.00E+00 | — | >5 |

*The number of surviving bacteria cells per milliliter of assay five minutes after treatment with water blank.
**The number of surviving bacteria cells per milliliter of assay thirty minutes after treatment with water blank.

The cationic nanoparticles of the instant invention showed excellent activity against the gram-positive and the gram-negative strain. For both strains, a log reduction of >5 is found, which demonstrates excellent antimicrobial activity.

EXAMPLE 16

Antimicrobial Testing of Cationic Nanoparticles Contained in a Personal Care Formulation This test method is used to determine the microbiocidal activity of substances in solution (0.5%). The instant cationic nanoparticles are tested in combination with 1% PEG-40 to prove the ability of the instant invention to achieve a reduction in the number of viable bacteria cells, mold spores and yeast cells of relevant organisms, according to the modified conditions defined in EN 1040/1275, in a personal care composition.

An appropriate volume of test formulation is inoculated with a suspension of bacteria cells, mold spores or yeast cells. After 48 hours and 72 hours, aliquots are taken, inactivated and diluted. The number of surviving cells in each sample is determined by surface plate-count method. The difference of the surviving cells determined in the assay after contact time and the inoculation concentration ($1.55*10^6$ cfu, cfu=colony forming units) is given as log reduction according to the formula given in Instant Example 12. The minimal cell count reduction is given as <1, the maximum cell count reduction as >3.

Test Organisms: *Staphylococcus aureus* ATCC 6538
*Escherichia coli* ATCC 10536
*Pseudomonas aeruginosa* ATCC 15442
*Candida albicans* ATCC 10231
*Aspergillus niger* ATCC 16404
Microbiocidal activities of Cationic Nanoparticles [log reduction] at 5000 ppm concentration are given below:

TABLE 1

Microbiocidal activity of Cationic nanoparticles [log reduction]

| | S. aureus | | E. coli | |
|---|---|---|---|---|
| Instant Example | 5000 ppm/ 48 hr | 5000 ppm/ 72 hr | 5000 ppm/ 48 hr | 5000 ppm/ 72 hr |
| 2 (in 1% PEG-40) | >3 | >3 | >3 | >3 |
| 3 | >3 | >3 | >3 | >3 |
| 3 (in 1% PEG-40) | 1.2 | 2.2 | >3 | >3 |

PEG-40 is hydrogenated castor oil from Cognis Deutschland.

TABLE 2

Microbiocidal activity of Cationic nanoparticles [log reduction] at 5000 ppm

| Instant Example | P. aeruginosa 48 hours | P. aeruginosa 72 hours |
|---|---|---|
| 2 (in 1% PEG-40 & Castor Oil) | >3 | >3 |
| 3 | >3 | >3 |
| 3 (in 1% PEG-40 & Castor Oil) | >3 | >3 |

TABLE 3

Microbiocidal activity of Cationic nanoparticles [log reduction]

| | C. albicans | | A. niger | |
|---|---|---|---|---|
| Instant Example | 5000 ppm/ 48 hr | 5000 ppm/ 72 hr | 5000 ppm/ 48 hr | 5000 ppm/ 72 hr |
| 2 (in 1% PEG-40) | 1.7 | 2.2 | <1 | <1 |
| 3 | <1 | >3 | <1 | 2.4 |
| 3 (in 1% PEG-40) | <1 | <1 | <1 | <1 |

The cationic nanoparticles of the instant invention showed excellent activity against the gram-positive and the gram-negative strain.

EXAMPLES 17-20

Hair Conditioning Formulations

Hair conditioning formulations are prepared according to Table 4.

TABLE 4

| Ingredients, wt % | Typical Range Based on Activity | 17 | 18 | 19 | 20 |
|---|---|---|---|---|---|
| Water | qs to 100% | qs to 100% | qs to 100% | qs to 100% | qs to 100% |
| Conditioning Agent | | | | | |
| Guar Hydroxypropyltrimonium Chloride | 0-2% | | | | |
| Polyquaternium-10 | 0-5% | | | | |
| Acrylamidopropyltrimonium Chloride/Acrylamide Copolymer | 0-0.5% | 0.05 | | | 0.5 |
| Cationic Nanoparticles of Examples 1-11 | 0-10% | 3.0 | 1.0 | 2.0 | 5.0 |
| Thickeners | | | | | |
| Polyquaternium 37 and Mineral Oil and PPG-1 Trideceth-6 | 0-5% | 3.0 | 2.0 | | 2.5 |
| Polyquaternium 37 and Propylene Dicaprylate Dicaprate and PPG-1 Trideceth-6 | 0-5% | | | 1.0 | |
| Waxes, alcohols & emulsifiers | | | | | |
| PEG-45 Palm Kernel Glycerides | 0-5% | 0.5 | — | 1.0 | — |
| Glycereth-31 | 0-10% | 1.0 | 2.0 | — | 1.0 |
| PPG-5-Ceteth-20 | 0-5% | — | 0.5 | — | 0.5 |
| Glyceryl Stearate and PEG-100 Stearate | 0-10% | 1.0 | — | 1.5 | — |
| Cetyl Alcohol | 0-10% | 1.0 | — | 0.5 | 1.0 |
| Glycol Stearate | 0-10% | 2.0 | 1.0 | — | 2.0 |
| Ethylene Glycol Distearate | 0-10% | — | 2.0 | 1.0 | — |
| Esters/Silicones | | | | | |
| Dimethicone PEG-8 Meadowfoamate | 0-5% | — | 1.0 | 2.0 | 3.0 |
| Amodimethicone | 0-5% | | 2.0 | | |

TABLE 4-continued

Hair Conditioning Formulations

| Ingredients, wt % | Typical Range Based on Activity | 17 | 18 | 19 | 20 |
|---|---|---|---|---|---|
| Vitamins | | | | | |
| Tocopherol | 0-1% | 0.1 | 0.1 | — | — |
| Panthenol | 0-1% | — | 0.1 | 0.1 | 0.1 |
| Fragrance | 0-2% | 0.5 | 0.5 | 0.5 | 0.5 |
| Chelating Agent | | | | | |
| Disodium EDTA | <0.10% | 0.1 | 0.1 | — | — |
| Tetrasodium EDTA | <0.10% | — | — | 0.1 | 0.1 |
| pH Adjuster | | | | | |
| NaOH | <0.50% | qs to 4.5-5.5 | qs to 4.5-5.5 | qs to 4.5-5.5 | qs to 4.5-5.5 |
| TEA | <0.50% | qs to 4.5-5.5 | qs to 4.5-5.5 | qs to 4.5-5.5 | qs to 4.5-5.5 |
| Preservative | | | | | |
| DMDM Hydantoin | 0-1% | 1.0 | 1.0 | — | — |
| Phenoxyethanol and Methylparaben and Propylparaben and Butylparaben and Isobutylparaben | 0-1% | — | — | 1.0 | 1.0 |

EXAMPLES 21-24

Lotion/Cream Formulation

Lotions and/or cream formulations are prepared according to Table 5.

TABLE 5

Lotions and/or Cream Formulations

| Ingredients, wt % | Typical Range Based on Activity | 21 | 22 | 23 | 24 |
|---|---|---|---|---|---|
| Water | qs to 100% | qs to 100% | qs to 100% | qs to 100% | qs to 100% |
| Humectant | | | | | |
| Glycerin | 0-10% | 5.0 | 2.5 | — | 4.0 |
| Propylene Glycol | 0-5% | — | 1.0 | 1.5 | 2.0 |
| Conditioner | | | | | |
| Cationic Nanoparticles of Examples 1-11 | 0-5% | 2.5 | 1.0 | 5.0 | 4.0 |
| Thickening agent | | | | | |
| Carbomer | 0-1% | — | — | — | 0.8 |
| Polyacrylamide and C13-14 Isoparaffin and Laureth-7 | 0-5% | — | — | 0.8 | — |
| Acrylates/Beheneth-25 Methacrylate Copolymer | 0-5% | — | 2.5 | — | — |
| Sodium Acrylates Copolymer and Mineral Oil and PPG-1 Trideceth-6 | 0-3% | 1.0 | — | — | — |
| Emulsifiers | | | | | |
| Glyceryl Stearate | 0-5% | 3.0 | 1.0 | 1.0 | 1.5 |
| Steareth-2 | 0-5% | — | — | 0.7 | — |
| PEG-100 Stearate | 0-5% | 2.0 | — | 0.5 | — |
| Waxes | | | | | |
| Cetyl Alcohol | 0-5% | 2.0 | 1.0 | — | 1.0 |
| Cetearyl Alcohol | 0-5% | — | — | — | 1.5 |
| Stearyl Alcohol | 0-5% | — | — | 1.0 | — |

TABLE 5-continued

Lotions and/or Cream Formulations

| Ingredients, wt % | Typical Range Based on Activity | 21 | 22 | 23 | 24 |
|---|---|---|---|---|---|
| Fatty Acids | | | | | |
| Stearic Acid | 0-10% | — | 2.5 | — | 3.0 |
| Behenic Acid | 0-10% | — | — | 1.0 | — |
| Oils/Esters | | | | | |
| Caprylic/Capric Triglyceride | 0-10% | 2.0 | 1.5 | — | 2.0 |
| Decyl Oleate | 0-5% | — | 0.5 | 0.8 | 1.5 |
| Cetyl Palmitate | 0-5% | 1.0 | 0.5 | — | 1.0 |
| Silicone | | | | | |
| Cyclomethicone | 0-5% | 1.0 | 1.0 | 4.0 | 2.0 |
| Dimethicone | 0-5% | — | — | — | 0.8 |
| Vitamins | | | | | |
| Tocopherol | 0-1% | 0.1 | — | 0.1 | 0.1 |
| Panthenol | 0-1% | — | 0.1 | — | 0.1 |
| Fragrance | 0-2% | 0.5 | 0.5 | 0.5 | 0.5 |
| Chelating Agent | | | | | |
| Disodium EDTA | <0.10% | 0.1 | — | 0.1 | — |
| Tetrasodium EDTA | <0.10% | — | 0.1 | — | 0.1 |
| pH Adjuster | | | | | |
| TEA | <0.50% | qs to 5.5-6.5 | qs to 5.5-6.5 | qs to 5.5-6.5 | qs to 5.5-6.5 |
| Preservative | | | | | |
| DMDM Hydantoin | 0-1% | — | — | 1.0 | — |
| Phenoxyethanol and Methylparaben and Propylparaben and Butylparaben and Isobutylparaben | 0-1% | 1.0 | 1.0 | — | 1.0 |

EXAMPLE 25

2 in 1 Shampoo Formulation

Table 6 gives a formulation for a 2 and 1 shampoo. The inventive cationic nanoparticles are added to the formulation below at 0.05 and 0.1 weight percent concentration. The formulations below incorporating the cationic nanoparticles are compared to control shampoo formulations wherein the inventive cationic nanoparticles is replaced with a cationic polymer at 0.05 and 0.1 weight % (cationic cellulose, Polyquaternium 10 or Guar hydroxypropyl trimethylammonium chloride) and 2 weight % polydimethylsiloxane.

TABLE 6

2 in 1 Shampoo Formulations

| Component | Weight % |
|---|---|
| Water | qs to 100% |
| ALES-3[1] | 10 |
| ALS[2] | 4 |
| Cocamidopropyl Betaine | 3 |
| Ethylene Glycol distearate | 2 |
| Cetyl Alcohol | 1.5 |
| Cocamide MEA | 1.0 |
| Cationic Nanoparticles of the Present Invention (Examples 1-11) | 0.10 and 0.05 |

[1]Ammonium lauryl ether (3 ethoxylate untis) sulfate.
[2]Ammonium lauryl sulfate.

The shampoo pH is adjusted to 5.5. Sodium chloride is used to adjust the viscosity of the shampoos to approximately 6000 cps. The control formulations with polysiloxane and Polyquaternium 10 or Guar hydroxypropyl trimethylammonium chloride polyquaternium 10 are homogenized until a polysiloxane droplet size ranging from 0.1 to about 20.0 microns are attained.

The measured values of hair treated with the inventive nanoparticles and the results for substantivity and build-up of silicone, and reductions in wet and dry combing energies on hair demonstrate the excellent conditioning properties of the inventive cationic nanoparticles in a 2 in 1 shampoo formulation.

EXAMPLES 26-27

2 in 1 Shampoo Formulations

Examples 26 and 27 are formulated in the 2 and 1 shampoo as in Table 6 except the inventive cationic nanoparticles are added at 0.5 wt. %. Comparisons are made using the cationic nanoparticles alone and in combination with a cationic potato starch.

EXAMPLE 28

Facial Moisturizer Formulation

A facial moisturizer formulation is prepared comprising the list of ingredients below.

| Facial Moisturizer Formulation | |
| --- | --- |
| Ingredient | Amount (wt-%) |
| Aqua | qs to 100 |
| Cationic Nanoparticles of the Present Invention (Examples 1-11) | 2.00 |
| Coco-caprylate/Caprate | 2.50 |
| Squalane | 2.00 |
| Hexyl Laurate | 2.00 |
| Ethylhexyl Palmitate | 2.00 |
| Dimethicone | 2.50 |
| Ethylhexyl Methoxycinnamate | 5.00 |
| Parfum | 0.20 |
| Preservative | 0.20 |

EXAMPLE 29

Body Moisturizer Formulation

A body moisturizer formulation is prepared comprising the list of ingredients below.

| Body Moisturizer Formulation | |
| --- | --- |
| Ingredient | Amount (wt-%) |
| Aqua | qs to 100 |
| Cationic Nanoparticle of the Present Invention (Examples 1-11) | 1.00 |
| Stearyl Alcohol | 5.00 |
| Cetyl Alcohol | 5.00 |
| Dimethicone | 5.00 |
| Cetearyl Stearate | 2.00 |
| Glycerin | 2.00 |
| Propylene Glycol | 2.00 |
| Parfum | 0.20 |
| Preservative | 0.20 |

EXAMPLE 30

Spray Moisturizer Formulation

A spray moisturizer formulation is prepared comprising the list of ingredients below.

| Spray Moisturizer Formulation | |
| --- | --- |
| Ingredient | Amount (wt-%) |
| Aqua | qs to 100 |
| Cationic Nanoparticle of the Present Invention (Examples 1-11) | 1.50 |
| Cyclomethicone | 3.00 |
| Hydrogenated Polydecene | 5.00 |
| Isostearyl Lactate | 1.50 |
| Sodium Hyaluronate | 1.00 |
| Glyceryl Myristate | 1.00 |
| Parfum | 0.20 |
| Preservative | 0.20 |

EXAMPLE 31

Leave-On Conditioner Formulation

A leave-on conditioner formulation is prepared comprising the list of ingredients below.

| Leave-on Conditioner Formulation | |
| --- | --- |
| Ingredient | Amount (wt-%) |
| Aqua | qs to 100 |
| Cationic Nanoparticles of the Present Invention (Examples 1-11) | 1.50 |
| Propylene Glycol | 2.00 |
| Glycerin | 2.00 |
| Dimethicone Copolyol | 2.00 |
| Preservative | 0.25 |
| Parfum | 0.30 |
| Ethylhexyl Methoxycinnamate | 2.00 |

EXAMPLE 32

Silicone Conditioner Formulation

A silicone conditioner formulation is prepared comprising the list of ingredients below.

| Silicone Conditioner Formulation | |
| --- | --- |
| Ingredient | Amount (wt-%) |
| Aqua | qs to 100 |
| Cationic Nanoparticles of the Present Invention (Examples 1-11) | 2.00 |
| Cyclopentasiloxane (and) Dimethiconol | 2.00 |
| Cyclomethicone | 2.00 |
| Ceteareth-5 | 0.75 |
| Preservative | 0.20 |
| Dimethicone PEG-8 Meadowfoamate | 0.50 |
| Parfum | 0.20 |

EXAMPLE 33

Rinse-Off Conditioner Formulation

A rinse-off conditioner formulation is prepared comprising the list of ingredients below.

| Rinse-Off Conditioner Formulation | |
| --- | --- |
| Ingredient | Amount (wt-%) |
| Aqua | qs to 100 |
| Cationic Nanoparticles of the Present Invention (Examples 1-11) | 2.00 |
| Decyl Oleate | 2.00 |
| *Helianthus Annuus* | 2.50 |
| Dimethicone (and) Dimethiconol | 2.50 |
| Preservative | 0.20 |
| Parfum | 0.30 |
| CI 18965 | 0.02 |
| Sodium Benzotriazolyl Butylphenol Sulfonate (and) Buteth-3 (and) Tributyl Citrate | 0.20 |

EXAMPLE 34

Sunless Tanning Cream with Sunscreen Formulation

A sunless tanning cream with sunscreen formulation is prepared comprising the list of ingredients below.

| Sunless Tanning Cream with Sunscreen Formulation | |
|---|---|
| Ingredient | Amount (wt-%) |
| Aqua | qs to 100 |
| Cationic Nanoparticles of the Present Invention (Examples 1-11) | 2.00 |
| Ethylhexyl Methoxycinnamate | 5.00 |
| Dihydroxyacetone | 3.00 |
| Methylene bis-Benzotriazolyl Tetramethyl Butylphenol | 3.00 |
| Paraffinum Liquidum | 7.50 |
| Preservative | 0.50 |
| Glycerin | 2.00 |
| Parfum | 0.50 |

EXAMPLE 35

Moisturizing Lipstick Formulation

A moisturizing lipstick formulation is prepared comprising the list of ingredients below.

| Moisturizing Lipstick Formulation | |
|---|---|
| Ingredient | Amount (wt-%) |
| *Ricinus Communis* | 25.00 |
| *Euphorbia Cerifera* | 5.40 |
| *Copernicia Cerifera* | 4.00 |
| Ozokerite | 5.00 |
| Hydrogenated Lanolin | 11.10 |
| Microcrystalline Wax | 4.50 |
| Cationic Nanoparticles of the Present Invention (Examples 1-11) | 2.25 |
| Octyldodecanol | 6.60 |
| Isocetyl Palmitate | 5.00 |
| Beeswax | 2.00 |
| Cetearyl Alcohol | 20.00 |
| Preservative | 0.10 |
| Tetradibutyl Pentaerythrityl Hydroxyhydrocinnamate | 0.05 |
| Pigment | 9.00 |

EXAMPLE 36

Moisturizing Soap Base Formulation

A moisturizing soap base formulation is prepared comprising the list of ingredients below.

| Moisturizing Soap Base Formulation | |
|---|---|
| Ingredient | Amount (wt-%) |
| Cationic Nanoparticles of the Present Invention (Examples 1-11) | 1.00 |
| Sodium Tallowate (and) Sodium Cocoate | 98.10 |
| Tetrasodium EDTA | 0.10 |
| Titanium Dioxide | 0.10 |
| Tetradibutyl Pentaerythrityl Hydroxyhydrocinnamate | 0.05 |
| Parfum | 0.50 |

EXAMPLE 37

Anti-Acne Skin Cream Formulation

An anti-acne skin cream formulation is prepared comprising the list of ingredients below.

| Anti-Acne Skin Cream Formulation | |
|---|---|
| Ingredient | Amount (wt-%) |
| Aqua | qs to 100 |
| Cationic Nanoparticles of the Present Invention (Examples 1-11) | 4.00 |
| Alcohol | 5.00 |
| Isocetyl Palmitate | 2.00 |
| Salicylic Acid | 2.00 |
| Paraffinum Liquidum | 1.00 |
| Preservative | 0.50 |
| Glycerin | 2.00 |
| Parfum | 0.50 |

EXAMPLE 38

Conditioner Formulation

A conditioner formulation is prepared comprising the list of ingredients below.

| Conditioner Formulation | |
|---|---|
| Ingredient | Amount (wt-%) |
| Aqua | qs to 100 |
| Glycerin | 5.00 |
| DMDM Hydantoin | 0.50 |
| Methylparaben | 0.20 |
| Polysorbate 80 | 1.00 |
| Parfum | 0.20 |
| Phenoxyethanol | 0.50 |
| Polyquaternium-6 | 2.00 |
| Cationic Nanoparticles of the Present Invention (Examples 1-11) | 5.60 |

What is claimed is:

1. A personal care composition comprising
   (a) an effective amount of at least one cationic nanoparticle of formula (I)

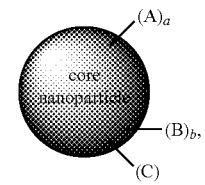

wherein
said cationic nanoparticle core comprises an inorganic material and where
A is an organic substituent covalently bound to the core nanoparticle surface and containing at least one cationic group L;
B is an organic substituent covalently bound to the core nanoparticle surface and containing at least one cationic moiety G;
C is an organic substituent covalently bound to the core nanoparticle surface containing at least one functional group Z;
a is a number from 1 to $n_a$;
b is a number from 0 to $n_b$;
c is a number from 0 to $n_c$;

where the sum of $n_a+n_b+n_c$ is a number from 1 up to $n_t$, where $n_t$ is limited by the geometry and surface area of the core nanoparticle and the steric requirements of the respective substituents A, B, C; and
(b) a cosmetically acceptable adjuvant.

2. A composition according to claim 1 wherein the organic substituent covalently bound to the core nanoparticle surface is A, B, and/or C wherein

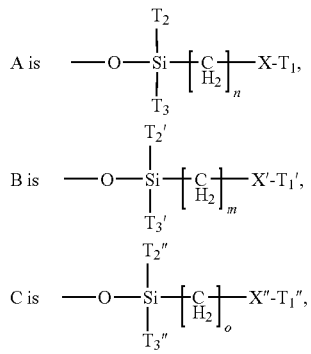

X, X' and X" are independently of one another —O—, —S—, —NR$_1$—, —NR$_{101}$—, —OCO—, —SCO—, —NR$_1$CO—, —OCOO—, —OCONR$_1$—, —NR$_1$COO—, —NR$_1$CONR$_2$— or a single bond;

n, m or o are independently of each other numbers from 0 to 8, and if n is 0, then X is a single bond;
if m is 0, then X' is a single bond;
if o is 0, then X" is a single bond;

$R_1$ and $R_2$ are independently of one another hydrogen, $C_1$-$C_{25}$ alkyl, $C_3$-$C_{25}$ alkyl which is interrupted by oxygen or sulfur, $C_6$-$C_{12}$ aryl or R;

$R_{101}$ is $C_1$-$C_{24}$acyl;

$T_1$ has the meaning of R and contains at least one cationic group L;

$T_1'$ has the meaning of R and contains at least one cationic moiety G;

$T_1''$ has the meaning of R and contains at least one moiety Z;

$T_2$, $T_2'$, $T_2''$, $T_3$, $T_3'$, $T_3''$ are independently of one another hydrogen, $C_1$-$C_{25}$alkyl, $C_3$-$C_{25}$alkyl which is interrupted by oxygen or sulphur, $C_2$-$C_{24}$alkenyl, phenyl, $C_7$-$C_9$phenylalkyl, —OR$_3$,

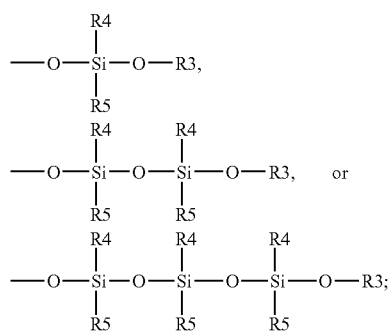

$R_3$ is hydrogen, $C_1$-$C_{25}$alkyl, $C_3$-$C_{25}$alkyl which is interrupted by oxygen or sulphur, $C_2$-$C_{24}$alkenyl, phenyl, $C_7$-$C_9$phenylalkyl,

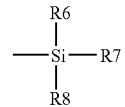

or nanoparticle surface;

$R_4$ and $R_5$ independently of each other are hydrogen, $C_1$-$C_{25}$alkyl, $C_3$-$C_{25}$alkyl which is interrupted by oxygen or sulphur, $C_2$-$C_{24}$alkenyl, phenyl, $C_7$-$C_9$phenylalkyl or —OR$_3$;

$R_6$, $R_7$ and $R_8$ independently of each other are hydrogen, $C_1$-$C_{25}$alkyl, $C_3$-$C_{25}$alkyl which is interrupted by oxygen or sulphur, $C_2$-$C_{24}$alkenyl, phenyl or $C_7$-$C_9$phenylalkyl;

R is $C_1$-$C_{20}$ alkyl, $C_5$-$C_{12}$cycloalkyl, $C_2$-$C_{20}$ alkenyl, $C_5$-$C_{12}$cycloalkenyl, $C_2$-$C_{20}$ alkynyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$ alkenyl substituted by one or more D, $C_3$-$C_{20}$ alkenyl interrupted by one or more E, $C_3$-$C_{20}$ alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D or, provided that X, X', or X", has the meaning of a single bond, R can be L, G, or Z;

D is L, G, Z, $R_9$, $OR_9$, $SR_9$, $NR_9R_{10}$, halogen, $NO_2$, CN, O-glycidyl, O-vinyl, O-allyl, $COR_9$, $NR_9COR_{10}$, $COOR_9$, $OCOR_9$, $CONR_9R_{10}$, $OCOOR_9$, $OCONR_9R_{10}$, $NR_9COOR_{10}$, $SO_3H$, $COOM_C$, $COO^-$, $SO_3^-$ or $SO_3M_C$, phenyl, $C_7$-$C_9$alkylphenyl;

E is O, S, COO, OCO, CO, $NR_9$, $NCOR_9$, $NR_9CO$, $CONR_9$, OCOO, $OCONR_9$, $NR_9COO$, $SO_2$, SO,

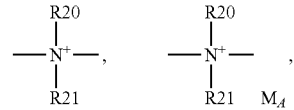

$CR_9$=$CR_{10}$ or

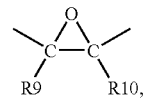

C≡C, N=C—$R_9$, $R_9$C=N, $C_5$-$C_{12}$Cycloalkylene, phenylene and/or phenylene substituted by D;

L and G are independently

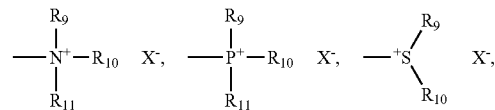

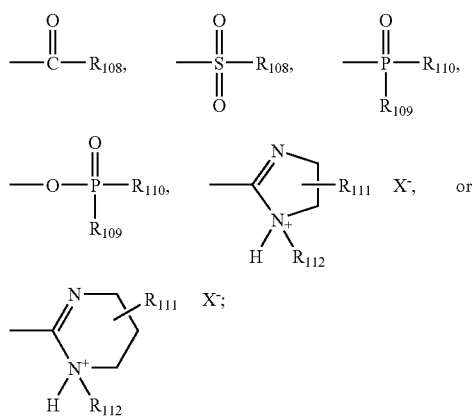

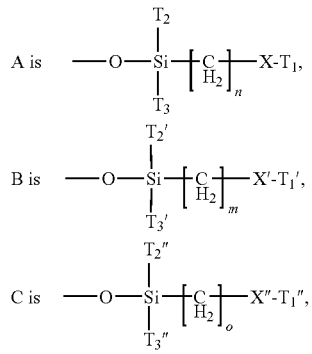

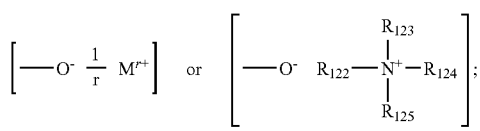

$R_9$, $R_{10}$ or $R_{11}$ independently of one another are hydrogen, $C_1$-$C_{25}$alkyl, benzyl, or phenyl;

$R_{20}$ and $R_{21}$ independently of one another are hydrogen, $C_1$-$C_{25}$alkyl, benzyl, or phenyl;

$R_{108}$, $R_{109}$ and $R_{110}$ are each independently of the others hydroxyl, $R_{111}$ is hydrogen or $C_1$-$C_{25}$alkyl;

$R_{112}$ is hydrogen or $C_1$-$C_{25}$alkyl, $C_3$-$C_{25}$alkyl interrupted by oxygen, sulfur or by or $C_2$-$C_{24}$alkenyl;

$R_{122}$, $R_{123}$, $R_{124}$ and $R_{125}$ are each independently of the others hydrogen, $C_1$-$C_{25}$alkyl or hydroxyl-substituted $C_2$-$C_{24}$alkyl;

M is an r-valent metal cation;

$X^-$ is fluoride, chloride, bromide, iodide, nitrite, nitrate, hydroxide, acetate, hydrogen sulfate, sulfate, methyl sulfate or mixtures thereof;

r is 1, 2 or 3;

Z is halogen, CN, $NO_2$, or a cationic moiety, anionic moiety, hydrophilic moiety, hydrophobic moiety, polysiloxane moiety, polyhalogenated moiety, polyethyleneglycol moiety, polypropyleneglycol moiety, metal complex or a polymer;

$M_C$ is an inorganic or organic cation; and $M_A$ is an inorganic or organic anion.

3. A composition according to claim 1 wherein the organic substituent covalently bound to the core nanoparticle surface is A, B, and/or C X, X' and X" are independently of one another —O—, —$NR_1$—, —$NR_{101}$—, —OCO—, —$NR_1$CO—, —OCOO—, —$NR_1$COO— or a single bond;

n, m or o are independently of each other numbers from 0 to 6, and if n is 0, then X is a single bond;
if m is 0, then X' is a single bond;
if o is 0, then X" is a single bond;

$R_1$ and $R_2$ are independently of one another hydrogen, $C_1$-$C_{18}$ alkyl, $C_3$-$C_{25}$ alkyl which is interrupted by oxygen, $C_6$-$C_{12}$ aryl or R;

$R_{101}$ is $C_1$-$C_{18}$acyl;

$T_1$ has the meaning of R and contains at least one cationic group L;

$T_1'$ has the meaning of R and contains at least one cationic moiety G;

$T_1''$ has the meaning of R and contains at least one moiety Z;

$T_2$, $T_2'$, $T_2''$, $T_3$, $T_3'$, $T_3''$ are independently of one another $C_1$-$C_{18}$alkyl, $C_3$-$C_{25}$alkyl which is interrupted by oxygen, $C_2$-$C_{24}$alkenyl, phenyl, $C_7$-$C_9$phenylalkyl, or —$OR_3$;

$R_3$ is hydrogen, $C_1$-$C_{18}$alkyl, $C_3$-$C_{25}$alkyl which is interrupted by oxygen, $C_2$-$C_{24}$alkenyl, phenyl, $C_7$-$C_9$phenylalkyl, or nanoparticle surface;

R is $C_1$-$C_{18}$alkyl, $C_5$-$C_{12}$cycloalkyl, $C_2$-$C_{20}$alkenyl, $C_5$-$C_{12}$cycloalkenyl, $C_6$-$C_{14}$aryl, $C_1$-$C_{18}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D or, provided that X, X', or X", has the meaning of a single bond, R can be L, G, or Z;

D is L, G, Z, $R_9$, $OR_9$, $SR_9$, $NR_9R_{10}$, Cl, Br, I, $NO_2$, CN, $COR_9$, $NR_9COR_{10}$, $COOR_9$, $COOR_9$, $CONR_9R_{10}$, $OCOOR_9$, $OCONR_9R_{10}$, $NR_9COOR_{10}$, $SO_3H$, $COOM_C$, $COO^-$, $SO_3^-$ or $SO_3M_C$, phenyl, $C_7$-$C_9$alkylphenyl;

E is O, S, COO, OCO, CO, $NR_9$, $NCOR_9$, $NR_9CO$, $CONR_9$, OCOO, OCONR_9, $NR_9COO$, $SO_2$, SO,

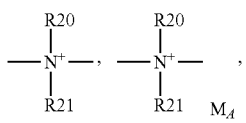

$C_5$-$C_{12}$Cycloalkylene, phenylene and/or phenylene substituted by D;

L and G are independently

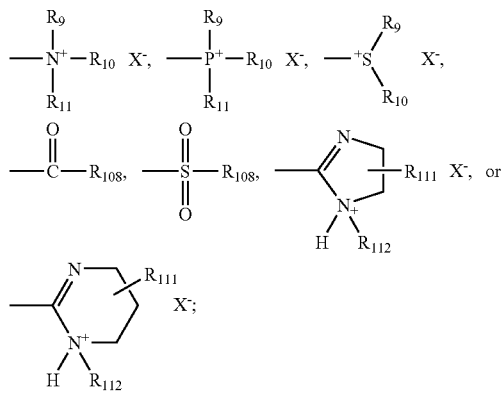

$R_9$, $R_{10}$ or $R_{11}$ independently of one another are hydrogen, $C_1$-$C_{25}$alkyl, benzyl, or phenyl;

$R_{20}$ and $R_{21}$ independently of one another are hydrogen, $C_1$-$C_{25}$alkyl, benzyl, or phenyl;

$R_{108}$ is hydroxyl,

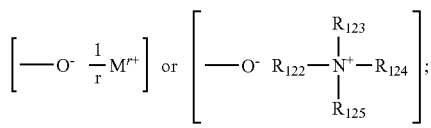

$R_{111}$ is hydrogen or $C_1$-$C_{18}$alkyl;

$R_{112}$ is hydrogen or $C_1$-$C_{18}$alkyl, $C_3$-$C_{25}$alkyl interrupted by oxygen or by

or $C_2$-$C_{24}$alkenyl;

$R_{122}$, $R_{123}$, $R_{124}$ and $R_{125}$ are each independently of the others hydrogen, $C_1$-$C_{18}$alkyl or hydroxyl-substituted $C_2$-$C_{24}$alkyl;

M is an r-valent metal cation;

$X^-$ is fluoride, chloride, bromide, iodide, nitrite, nitrate, hydroxide, acetate, hydrogen sulfate, sulfate, methyl sulfate or mixtures thereof;

r is 1, 2 or 3;

Z is halogen, CN, $NO_2$, or a cationic moiety, anionic moiety, hydrophilic moiety, hydrophobic moiety, polysiloxane moiety, polyethyleneglycol moiety, or, polypropyleneglycol moiety;

$M_C$ is an inorganic or organic cation; and $M_A$ is an inorganic or organic anion.

4. A composition according to claim 1 wherein the organic substituent covalently bound to the core nanoparticle surface is A, B, and/or C

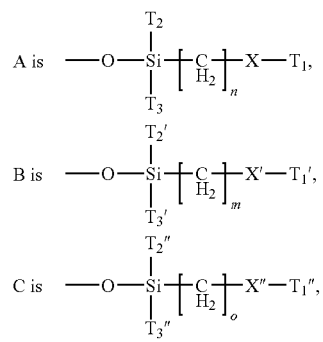

X, X' and X" are independently of one another —O—, —$NR_1$, —OCO—, —$NR_1$COO— or a single bond;

n, m or o is independently of each other numbers from 1 to 3;

$R_1$ is hydrogen, $C_1$-$C_{18}$ alkyl, $C_3$-$C_{25}$ alkyl which is interrupted by oxygen, $C_6$-$C_{12}$ aryl or R;

$R_{101}$ is $C_1$-$C_{18}$acyl;

$T_1$ has the meaning of R and contains at least one cationic group L;

$T_1'$ has the meaning of R and contains at least one cationic moiety G;

$T_1''$ has the meaning of R and contains at least one moiety Z;

$T_2$, $T_2'$, $T_2''$, $T_3$, $T_3'$, $T_3''$ are independently of one another $C_1$-$C_{18}$alkyl, $C_3$-$C_{25}$alkyl which is interrupted by oxygen, phenyl, $C_7$-$C_9$-phenylalkyl, or —$OR_3$;

$R_3$ is $C_1$-$C_{18}$alkyl, $C_3$-$C_{25}$alkyl which is interrupted by oxygen, phenyl, $C_7$-$C_9$phenylalkyl, or nanoparticle surface;

R is $C_1$-$C_{18}$alkyl, $C_5$-$C_{12}$cycloalkyl, $C_6$-$C_{14}$aryl, $C_1$-$C_{18}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, or $C_6$-$C_{14}$aryl substituted by one or more D; or, provided that X, X', or X", has the meaning of a single bond, R can be L, G, or Z;

D is L, G, Z, $R_9$, $OR_9$, $NR_9R_{10}$, Cl, Br, I, $NR_9COR_{10}$, $COOR_9$, $OCOR_9$, $CONR_9R_{10}$, $OCONR_9R_{10}$, $NR_9COOR_{10}$, $SO_3H$, $COOM_C$, $COO^-$, $SO_3^-$ or $SO_3M_C$, phenyl, $C_7$-$C_9$alkylphenyl;

E is O, COO, CO, $NR_9$, $NCOR_9$, $NR_9CO$, $CONR_9$, OCOO, $OCONR_9$, $NR_9COO$, $SO_2$, SO,

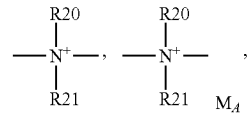

$C_5$-$C_{12}$Cycloalkylene, phenylene and/or phenylene substituted by D;

L and G are independently

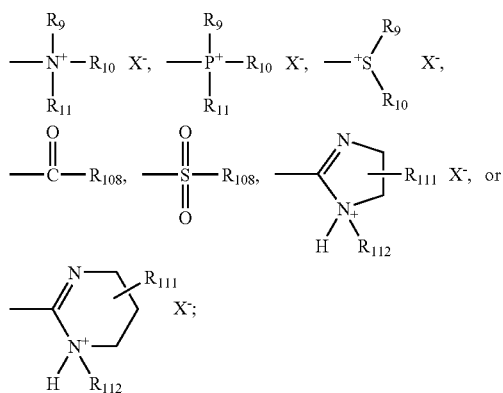

$R_9$, $R_{10}$ or $R_{11}$ independently of one another are hydrogen, $C_1$-$C_{15}$alkyl, benzyl, or phenyl;

$R_{20}$ and $R_{21}$ independently of one another are hydrogen, $C_1$-$C_{15}$alkyl, benzyl, or phenyl;

$R_{111}$ is hydrogen or $C_1$-$C_{18}$alkyl;

$R_{112}$ is hydrogen or $C_1$-$C_{18}$alkyl, $C_3$-$C_{25}$alkyl interrupted by oxygen or by

$X^-$ is fluoride, chloride, bromide, iodide, nitrite, nitrate, hydroxide, acetate, hydrogen sulfate, sulfate, methyl sulfate or mixtures thereof;

Z is halogen or a cationic moiety, anionic moiety, hydrophilic moiety, hydrophobic moiety, polysiloxane moiety, polyethyleneglycol moiety, or, polypropyleneglycol moiety;

$M_C$ is an inorganic or organic cation; and $M_A$ is an inorganic or organic anion.

5. A composition according to claim 1, wherein said cationic nanoparticle core of formula (I) comprises an inorganic material selected from the group consisting of silicon oxide, $Al_2O_3$, $TiO_2$, silicon oxide-coated $TiO_2$, ZnO, $SnO_2$, $ZrO_2$, Ag, Au, Cu, Sb—$SnO_2$, $Fe_2O_3$, magnetite, IndiumTinOxide, antimony-doped tin oxide, indium oxide, antimony oxide, fluorine-doped tin oxide, phosphorous-doped tin oxide, zinc antimonite, indium doped zinc oxide and mixtures thereof.

6. A composition according to claim 1, wherein said cationic nanoparticle core of formula (I) comprises an inorganic material selected from the group consisting of silicon oxide, $Al_2O_3$, $TiO_2$, ZnO, $SnO_2$, $ZrO_2$, Sb—$SnO_2$, $Fe_2O_3$, magnetite, IndiumTinOxide, antimony-doped tin oxide, indium oxide and mixtures thereof.

7. A composition according to claim 1, wherein said cationic nanoparticle core of formula (I) comprises an inorganic material selected from the group consisting of silicon oxide, $Al_2O_3$, $TiO_2$, ZnO, $SnO_2$, $ZrO_2$, $Fe_2O_3$, magnetite, IndiumTinOxide, antimony-doped tin oxide and mixtures thereof.

8. A composition according to claim 1, wherein said cationic nanoparticle core of formula (I) comprises an inorganic material selected from the group consisting of silicon oxide, $Al_2O_3$, and mixtures thereof.

9. A composition according to claim 1 wherein said cationic nanoparticle core of formula (I) comprises an organic material wherein the organic substituent covalently bound to the core nanoparticle surface is A, B, and/or C A is —Y-$T_1$, B is —Y'-$T_1$', C is —Y"-$T_1$";

Y, Y' and Y" are independently of one another $C_1$-$C_{25}$ alkylene, —O—, —S—, —$NR_1$—, —OCO—, —SCO—, —$NR_1$CO—, —OCOO—, —OCON$R_1$—, —$NR_1$COO—, —$NR_1$CON$R_2$—, —COO—, —CON$R_1$—, —CO— or a single bond;

$T_1$ has the meaning of R and contains at least one cationic group L;

$T_1$' has the meaning of R and contains at least one cationic moiety G;

$T_1$" has the meaning of R and contains at least one moiety Z;

$R_1$ and $R_2$ are independently of one another hydrogen, $C_1$-$C_{25}$ alkyl, $C_3$-$C_{25}$ alkyl which is interrupted by oxygen or sulfur, $C_6$-$C_{12}$ aryl or R;

R is $C_1$-$C_{20}$ alkyl, $C_5$-$C_{12}$cycloalkyl, $C_2$-$C_{20}$alkenyl, $C_5$-$C_{12}$cycloalkenyl, $C_2$-$C_{20}$alkynyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D or, provided that Y, Y', or Y", has the meaning of a single bond, R can be L, G, or Z;

D is L, G, Z, $R_9$, $OR_9$, $SR_9$, $NR_9R_{10}$, halogen, $NO_2$, CN, O-glycidyl, O-vinyl, O-allyl, $COR_9$, $NR_9COR_{10}$, $COOR_9$, $OCOR_9$, $CONR_9R_{10}$, $OCOOR_9$, $OCONR_9R_{10}$, $NR_9COOR_{10}$, $SO_3H$, $COOM_C$, $COO^-$, $SO_3^-$ or $SO_3M_C$, phenyl, $C_7$-$C_9$alkylphenyl;

E is O, S, COO, OCO, CO, $NR_9$, $NCOR_9$, $NR_9CO$, $CONR_9$, OCOO, $OCONR_9$, $NR_9COO$, $SO_2$, SO,

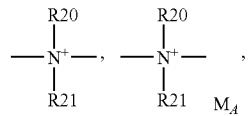

$CR_9$=$CR_{10}$ or

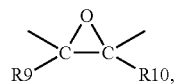

C≡C, N=C—$R_9$, $R_9$C=N, $C_5$-$C_{12}$Cycloalkylene, phenylene and/or phenylene substituted by D;

L and G are independently

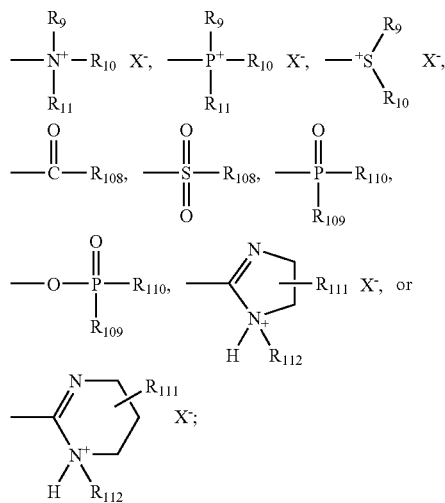

$R_9$, $R_{10}$ or $R_{11}$ independently of one another are hydrogen, $C_1$-$C_{25}$alkyl, benzyl, or phenyl;

$R_{20}$ and $R_{21}$ independently of one another are hydrogen, $C_1$-$C_{25}$alkyl, benzyl, or phenyl;

$R_{108}$, $R_{109}$ and $R_{110}$ are each independently of the others hydroxyl,

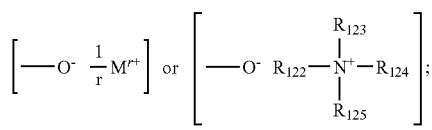

$R_{111}$ is hydrogen or $C_1$-$C_{25}$alkyl;

$R_{112}$ is hydrogen or $C_1$-$C_{25}$alkyl, $C_3$-$C_{25}$alkyl interrupted by oxygen, sulfur or by

or $C_2$-$C_{24}$alkenyl;

$R_{122}$, $R_{123}$, $R_{124}$ and $R_{125}$ are each independently of the others hydrogen, $C_1$-$C_{25}$alkyl or hydroxyl-substituted $C_2$-$C_{24}$alkyl;

M is an r-valent metal cation;

$X^-$ is fluoride, chloride, bromide, iodide, nitrite, nitrate, hydroxide, acetate, hydrogen sulfate, sulfate, methyl sulfate or mixtures thereof;

r is 1, 2 or 3;

Z is halogen, CN, $NO_2$, or a cationic moiety, anionic moiety, hydrophilic moiety, hydrophobic moiety, polysiloxane moiety, polyhalogenated moiety, polyethyleneglycol moiety, polypropyleneglycol moiety, metal complex or a polymer;

$M_C$ is an inorganic or organic cation; and $M_A$ is an inorganic or organic anion.

10. A composition according to claim 1, wherein said cationic nanoparticle core of formula (I) comprises an organic material wherein the organic substituent covalently bound to the core nanoparticle surface is A, B, and/or C A is —Y-$T_1$, B is —Y'-$T_1$', C is —Y"-$T_1$";

Y, Y' and Y" are independently of one another $C_1$-$C_{18}$ alkylene, —O—, —S—, —$NR_1$—, —OCO—, —$NR_1$CO—, —OCONR$_1$—, —$NR_1$COO—, —COO—, —CONR$_1$—, —CO— or a single bond;

$T_1$ has the meaning of R and contains at least one cationic group L;

$T_1$' has the meaning of R and contains at least one cationic moiety G;

$T_1$" has the meaning of R and contains at least one moiety Z;

$R_1$ and $R_2$ are independently of one another hydrogen, $C_1$-$C_{18}$ alkyl, $C_3$-$C_{25}$ alkyl which is interrupted by oxygen or sulfur, $C_6$-$C_{12}$ aryl or R;

R is $C_1$-$C_{18}$alkyl, $C_5$-$C_{12}$cycloalkyl, $C_2$-$C_{20}$alkenyl, $C_5$-$C_{12}$cycloalkenyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, $C_2$-$C_{20}$alkenyl substituted by one or more D, $C_3$-$C_{20}$alkenyl interrupted by one or more E, $C_3$-$C_{20}$alkenyl substituted by one or more D and interrupted by one or more E, $C_5$-$C_{12}$cycloalkenyl substituted by one or more D, $C_3$-$C_{12}$cycloalkenyl interrupted by one or more E, $C_3$-$C_{12}$cycloalkenyl substituted by one or more D and interrupted by one or more E, or $C_6$-$C_{14}$aryl substituted by one or more D or, provided that Y, Y', or Y", has the meaning of a single bond, R can be L, G, or Z;

D is L, G, Z, $R_9$, $OR_9$, $NR_9R_{10}$, Cl, Br, I, $NO_2$, CN, $COR_9$, $NR_9COR_{10}$, $COOR_9$, $COOR_9$, $CONR_9R_{10}$, $OCOOR_9$, $OCONR_9R_{10}$, $NR_9COOR_{10}$, $SO_3H$, $COOM_C$, $COO^-$, $SO_3^-$ or $SO_3M_C$, phenyl, $C_7$-$C_9$alkylphenyl;

E is O, COO, OCO, CO, $NR_9$, $NCOR_9$, $NR_9CO$, $CONR_9$, $OCONR_9$, $NR_9COO$, $SO_2$, SO,

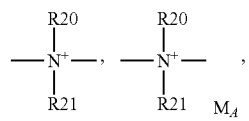

$C_5$-$C_{12}$Cycloalkylene, phenylene and/or phenylene substituted by D;

L and G are independently

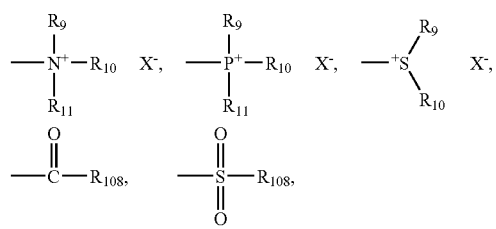

-continued

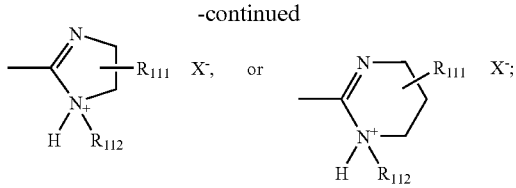

$R_9$, $R_{10}$ or $R_{11}$ independently of one another are hydrogen, $C_1$-$C_{18}$alkyl, benzyl, or phenyl;

$R_{20}$ and $R_{21}$ independently of one another are hydrogen, $C_1$-$C_{18}$alkyl, benzyl, or phenyl;

$R_{108}$ is hydroxyl,

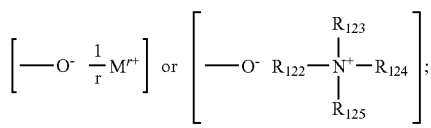

$R_{111}$ is hydrogen or $C_1$-$C_{18}$alkyl;

$R_{112}$ is hydrogen or $C_1$-$C_{18}$alkyl, $C_3$-$C_{25}$alkyl interrupted by oxygen, sulfur or by

$R_{122}$, $R_{123}$, $R_{124}$ and $R_{125}$ are each independently of the others hydrogen, $C_1$-$C_{25}$alkyl or hydroxyl-substituted $C_2$-$C_{24}$alkyl;

M is an r-valent metal cation;

$X^-$ is fluoride, chloride, bromide, iodide, nitrite, nitrate, hydroxide, acetate, hydrogen sulfate, sulfate, methyl sulfate or mixtures thereof;

r is 1, 2 or 3;

Z is halogen, CN, $NO_2$, or a cationic moiety, anionic moiety, hydrophilic moiety, hydrophobic moiety, polysiloxane moiety, polyethyleneglycol moiety, or polypropyleneglycol moiety;

$M_C$ is an inorganic or organic cation; and $M_A$ is an inorganic or organic anion.

11. A composition according to claim 9, wherein said cationic nanoparticle core of formula (I) comprises an organic material wherein the organic substituent covalently bound to the core nanoparticle surface is A, B, and/or C A is —Y-$T_1$,
B is —Y'-$T_1$',
C is —Y"-$T_1$";

Y, Y' and Y" are independently of one another $C_1$-$C_{18}$ alkylene, —O—, —$NR_1$—, —OCO—, —$NR_1$CO—, —OCO$NR_1$—, —$NR_1$COO—, —COO—, —CO$NR_1$— or a single bond;

$T_1$ has the meaning of R and contains at least one cationic group L;

$T_1$' has the meaning of R and contains at least one cationic moiety G;

$T_1$" has the meaning of R and contains at least one moiety Z;

$R_1$ and $R_2$ are independently of one another hydrogen, $C_1$-$C_{18}$ alkyl, $C_3$-$C_{25}$ alkyl which is interrupted by oxygen or sulfur, $C_6$-$C_{12}$ aryl or R;

R is $C_1$-$C_{18}$alkyl, $C_5$-$C_{12}$cycloalkyl, $C_6$-$C_{14}$aryl, $C_1$-$C_{20}$alkyl substituted by one or more D, $C_2$-$C_{20}$alkyl interrupted by one or more E, $C_2$-$C_{20}$alkyl substituted by one or more D and interrupted by one or more E, $C_5$-$C_{12}$cycloalkyl substituted by one or more D, $C_2$-$C_{12}$cycloalkyl interrupted by one or more E, $C_2$-$C_{12}$cycloalkyl substituted by one or more D and interrupted by one or more E, or $C_6$-$C_{14}$aryl substituted by one or more D; or, provided that Y, Y', or Y", has the meaning of a single bond, R can be L, G, or Z;

D is L, G, Z, $R_9$, $OR_9$, $NR_9R_{10}$, Cl, Br, I, $NO_2$, CN, $COR_9$, $NR_9COR_{10}$, $COOR_9$, $OCOR_9$, $CONR_9R_{10}$, $OCOOR_9$, $OCONR_9R_{10}$, $NR_9COOR_{10}$, $SO_3H$, $COOM_C$, $OCO^-$, $SO_3^-$ or $SO_3M_C$, phenyl, $C_7$-$C_9$alkylphenyl;

E is O, COO, OCO, CO, $NR_9$, $NCOR_9$, $NR_9CO$, $CONR_9$, $OCONR_9$, $NR_9COO$, $SO_2$, SO,

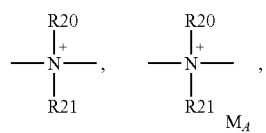

$C_5$-$C_{12}$Cycloalkylene, phenylene and/or phenylene substituted by D;

L and G are independently

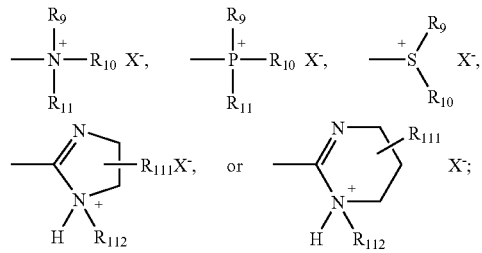

$R_9$, $R_{10}$ or $R_{11}$ independently of one another are hydrogen, $C_1$-$C_{18}$alkyl, benzyl, or phenyl;

$R_{20}$ and $R_{21}$ independently of one another are hydrogen, $C_1$-$C_{18}$alkyl, benzyl, or phenyl;

$R_{111}$ is hydrogen or $C_1$-$C_{18}$alkyl;

$R_{112}$ is hydrogen or $C_1$-$C_{18}$alkyl, $C_3$-$C_{25}$alkyl interrupted by oxygen, sulfur or by

$R_{122}$, $R_{123}$, $R_{124}$ and $R_{125}$ are each independently of the others hydrogen, $C_1$-$C_{25}$alkyl or hydroxyl-substituted $C_2$-$C_{24}$alkyl;

$X^-$ is fluoride, chloride, bromide, iodide, nitrite, nitrate, hydroxide, acetate, hydrogen sulfate, sulfate, methyl sulfate or mixtures thereof;

Z is halogen, CN, $NO_2$, or a cationic moiety, anionic moiety, hydrophilic moiety, hydrophobic moiety, polysiloxane moiety, polyethyleneglycol moiety, or polypropyleneglycol moiety;

$M_C$ is an inorganic or organic cation; and $M_A$ is an inorganic or organic anion.

12. A composition according to claim 1 wherein said cationic nanoparticle core comprises an organic material of formula (II)

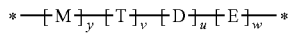     (II)

wherein
u, v, w, and y represent the percentage by weight that each repeating unit or derived monomer is contained within the organic material;
u, v, w, and y add up to total 100 weight percent relative to the total weight of the organic material;
u and w are independently from about 0 to about 94.9999% by weight of the organic material;
y is from about 5% to about 99.9999% by weight of the organic material;
v is from about 0.0001% to about 5% by weight of the organic material;
* is a terminal group, for example, a catalyst residue;
M, T, D and E are covalently bonded to each other;
M is derived from a monomer of formula (III)

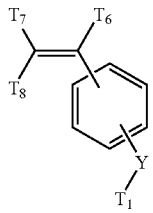     (III)

T6, T7, and T8 are C1-C4 alkyl or hydrogen;
D and E are independently derived from monomers selected from the group consisting of acrylic acid, (meth)acrylic acid, acryloxypropionic acid, crotonic acid, itaconic acid, maleic acid, fumaric acid, citraconic acid, 2-acrylamido-2-methyl propane sulfonic acid, styrene sulfonic acid, vinyl sulfonic acid, sulfoethyl (meth)acrylate, sulfopropyl (meth)acrylate, 2-acrylamido-2-methyl propane sulfinic acid, styrene sulfinic acid, and vinyl sulfinic acid, 2-phosphoethyl (meth)acrylate, vinyl phosphoric acid, vinyl phosphinic acid, N,N-dimethylaminoethyl (meth)acrylate, N,N-diethylaminoethyl (meth)acrylate, N-t-butylaminoethyl (meth)acrylate, N,N-dimethylaminopropyl (meth)acrylamide, p-aminostyrene, N,N-cyclohexylallylamine, allylamine, diallylamine, dimethylallylamine, N-ethyldimethylallylamine, crotyl amines, N-ethylmethallylamine, 2-vinylpyridine, 4-vinylpyridine, vinyl imidazole, oxazolidinylethyl (meth)acrylate, vinylbenzylamines, vinylphenylamines, 2-morpholinoethyl (meth)acrylate, methacrylamidopropyl trimethyl ammonium chloride, diallyl dimethyl ammonium chloride, 2-trimethyl ammonium ethyl methacrylic chloride, dimethyl-N-(3-methacrylamidopropyl)-N-(3-sulfopropyl) ammonium betaine, methyl (meth)acrylate, ethyl (meth)acrylate, propyl (meth)acrylate, butyl (meth)acrylate, isobutyl (meth)acrylate, hexyl (meth)acrylate, cyclohexyl (meth)acrylate, 2-ethylhexyl (meth)acrylate, octyl (meth)acrylate, decyl (meth)acrylate, dodecyl (meth)acrylate, pentadecyl (meth)acrylate, hexadecyl (meth)acrylate, octadecyl (meth)acrylate, nonadecyl (meth)acrylate, styrene, alpha-methylstyrene, vinyltoluene, p-methylstyrene, ethylvinylbenzene, vinylnaphthalene, vinylxylenes, vinyl acetate, vinyl formamide, vinyl chloride, vinyl fluoride, vinyl bromide, vinylidene chloride, vinylidene fluoride, vinylidene bromide and mixtures thereof; and
T is derived from monomers selected from the group consisting of divinyl benzene, trivinylbenzene, divinyltoluene, divinylpyridine, divinylnaphthalene divinylxylene, ethyleneglycol di(meth)acrylate, trimethylolpropane tri(meth)acrylate, diethyleneglycol divinyl ether, trivinylcyclohexane, allyl (meth)acrylate, diethyleneglycol di(meth)acrylate, propyleneglycol di(meth)acrylate, 2,2-dimethylpropane-1,3-di(meth)acrylate, 1,3-butylene glycol di(meth)acrylate, 1,4-butanediol di(meth)acrylate, 1,6-hexanediol di(meth)acrylate, tripropylene glycol di(meth)acrylate, triethylene glycol di(meth)acrylate, tetraethylene glycol di(meth)acrylate, polyethylene glycol di(meth)acrylates, polyethylene glycol 200 di(meth)acrylate, polyethylene glycol 600 di(meth)acrylate, ethoxylated bisphenol A di(meth)acrylate, poly(butanediol) di(meth)acrylate, pentaerythritol tri(meth)acrylate, trimethylolpropane triethoxy tri(meth)acrylate, glyceryl propoxy tri(meth)acrylate, pentaerythritol tetra(meth)acrylate, dipentaerythritol monohydroxypenta(meth)acrylate, divinyl silane, trivinyl silane, dimethyl divinyl silane, divinyl methyl silane, methyl trivinyl silane, diphenyl divinyl silane, divinyl phenyl silane, trivinyl phenyl silane, divinyl methyl phenyl silane, tetravinyl silane, dimethyl vinyl disiloxane, poly(methyl vinyl siloxane), poly(vinyl hydro siloxane), poly(phenyl vinyl siloxane), and mixtures thereof.

13. A composition according to claim 1, wherein said cationic nanoparticle core comprises an organic material of formula (II)

     (II)

wherein
u and w are independently from about 10% to about 84.99% by weight of the organic material;
y is from about 15% to about 89.99% by weight of the organic material;
v is from about 0.01% to about 5% by weight of the organic material;
M is derived from a monomer of formula (III)

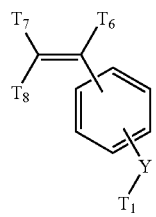     (III)

T6, T7, and T8 are methyl or hydrogen;
D and E are independently derived from monomers selected from the group consisting of acrylic acid, (meth)acrylic acid, acryloxypropionic acid, 2-acrylamido-2-methyl propane sulfonic acid, styrene sulfonic acid, vinyl sulfonic acid, sulfoethyl (meth)acrylate, sulfopropyl (meth)acrylate, 2-phosphoethyl (meth)acrylate, N,N-dimethylaminoethyl (meth)acrylate, N,N-diethylaminoethyl (meth)acrylate, N-t-butylaminoethyl (meth)acrylate, N,N-dimethylaminopropyl (meth)acrylamide, p-aminostyrene, N,N-cyclohexylallylamine, allylamine, diallylamine, dimethylallylamine, N-ethyldimethylallylamine, N-ethylmethallylamine, 2-vinylpyridine, 4-vinylpyridine, vinyl imidazole, methyl (meth)acrylate, ethyl (meth)acrylate, propyl (meth)acrylate, butyl (meth)acrylate, isobutyl (meth)acrylate, hexyl (meth)acrylate, cyclohexyl (meth)acrylate, 2-ethylhexyl (meth)acrylate, octyl (meth)acrylate, decyl (meth)acrylate, dodecyl (meth)acrylate, styrene, alpha-methylstyrene, vinyltoluene, p-methylstyrene, ethylvinylbenzene, vinylxylenes, vinyl acetate, vinyl formamide, vinyl chloride, and mixtures thereof; and T is derived from monomers selected from the group consisting of divinyl benzene, trivinylbenzene, divinyltoluene, divinylpyridine, divinylnaphthalene divinylxylene, ethyleneglycol di(meth)acrylate, trimethylolpropane tri(meth)acrylate, diethyleneglycol divinyl ether, trivinylcyclohexane, allyl (meth)acrylate, diethyleneglycol di(meth)acrylate, propyleneglycol di(meth)acrylate, 2,2-dimethylpropane-1,3-di(meth)acrylate, 1,3-butylene glycol di(meth)acrylate, 1,4-butanediol di(meth)acrylate, 1,6-hexanediol di(meth)acrylate, tripropylene glycol di(meth)acrylate, triethylene glycol di(meth)acrylate, tetraethylene glycol di(meth)acrylate, polyethylene glycol di(meth)acrylates, polyethylene glycol 200 di(meth)acrylate, polyethylene glycol 600 di(meth)acrylate, ethoxylated bisphenol A di(meth)acrylate, poly(butanediol) di(meth)acrylate, pentaerythritol tri(meth)acrylate, trimethylolpropane triethoxy tri(meth)acrylate, glyceryl propoxy tri(meth)acrylate, pentaerythritol tetra(meth)acrylate, di pentaerythritol monohydroxypenta(meth)acrylate, and mixtures thereof.

14. A composition according to claim 1 wherein said cationic nanoparticle core comprises an organic material of formula (II)

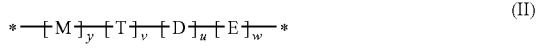
(II)

wherein
u and w are independently from about 25% to about 74.9% by weight of the organic material;
y is from about 25% to about 74.9% by weight of the organic material;
v is from about 0.1% to about 5% by weight of the organic material;
M is derived from a monomer of formula (III)

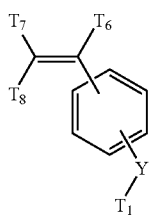
(III)

T6, T7, and T8 are hydrogen;
D and E are independently derived from monomers selected from the group consisting of acrylic acid, (meth)acrylic acid, N,N-dimethylaminoethyl (meth)acrylate, N,N-diethylaminoethyl (meth)acrylate, N-t-butylaminoethyl (meth)acrylate, N,N-dimethylaminopropyl (meth)acrylamide, p-aminostyrene, 2-vinylpyridine, 4-vinylpyridine, vinyl imidazole, methyl (meth)acrylate, ethyl (meth)acrylate, propyl (meth)acrylate, butyl (meth)acrylate, isobutyl (meth)acrylate, hexyl (meth)acrylate, cyclohexyl (meth)acrylate, 2-ethylhexyl (meth)acrylate, styrene, alpha-methylstyrene, vinyltoluene, p-methylstyrene, ethylvinylbenzene, vinyl acetate, and mixtures thereof; and T is derived from monomers selected from the group consisting of divinyl benzene, trivinylbenzene, divinyltoluene, divinylpyridine, ethyleneglycol di(meth)acrylate, trimethylolpropane tri(meth)acrylate, diethyleneglycol divinyl ether, trivinylcyclohexane, allyl (meth)acrylate, diethyleneglycol di(meth)acrylate, propyleneglycol di(meth)acrylate, 2,2-dimethylpropane-1,3-di(meth)acrylate, 1,3-butylene glycol di(meth)acrylate, 1,4-butanediol di(meth)acrylate, 1,6-hexanediol di(meth)acrylate, tripropylene glycol di(meth)acrylate, triethylene glycol di(meth)acrylate, tetraethylene glycol di(meth)acrylate, polyethylene glycol di(meth)acrylates, polyethylene glycol 200 di(meth)acrylate, polyethylene glycol 600 di(meth)acrylate, and mixtures thereof.

15. A composition according to claim 12, wherein said cationic nanoparticle core comprises an organic material of formula (II) wherein the weight average molecular weight of said organic material is from about 1,000 to about 10 million Daltons.

16. A composition according to claim 12 wherein said cationic nanoparticle core comprises an organic material of formula (II) wherein the weight average molecular weight of said organic material is from about 40,000 to about 4 million Daltons.

17. A composition according to claim 12 wherein said cationic nanoparticle core comprises an organic material of formula (II) wherein the weight average molecular weight of said organic material is from about 50,000 to about 2 million Daltons.

18. A composition according to claim 1, wherein the cationic nanoparticles of formula (I) component (a) are in the form of particles and have a particle size from about 0.001 to about 500 micrometers.

19. A composition according to claim 1 wherein the cationic nanoparticles of formula (I) component (a) are in the form of particles and have a particle size from about 0.01 to about 300 micrometers.

20. A composition according to claim 1 wherein the cationic nanoparticles of formula (I) component (a) are in the form of particles and have a particle size from about 1 to about 300 micrometers.

21. A composition according to claim 1, further comprising (c) at least one compound selected from the group consisting of the ultraviolet light absorbers, antioxidants, tocopherol, tocopherol acetate, hindered amine light stabilizers, complex formers, optical brighteners, surfactants, and polyorganosiloxanes.

22. A composition according to claim 1, further comprising (d) a dye or a pigment or mixtures thereof.

23. A composition according to claim 1, wherein the cationic nanoparticle of formula (I) component (a) is present in a concentration of about 0.0001 weight % to about 50 weight % based on the total weight of the composition.

24. A composition according to claim 1 where the cationic nanoparticle of formula (I) component (a) is present in a concentration of about 0.01 weight % to about 25 weight % based on the total weight of the composition.

25. A composition according to claim 1 where the cationic nanoparticle of formula (I) component (a) is present in a concentration of about 0.1 weight % to about 7 weight % based on the total weight of the composition.

26. A composition according to claim 1 where the cationic nanoparticle of formula (I) component (a) is present in a concentration of about 0.2 weight % to about 5 weight % based on the total weight of the composition.

27. A composition according to claim 1, wherein the personal care composition is a product selected from the group consisting of skin-care products, bath and shower products, liquid soaps, bar soaps, preparations containing fragrances and odoriferous substances, hair-care products, dentifrices, deodorizing and antiperspirant preparations, decorative preparations, light protection formulations and preparations containing active ingredients, shaving lotions, body oils, body lotions, body gels, treatment creams, skin protection ointments, shaving preparations, skin powders, shampoos, hair conditioners, 2 in 1 conditioners, leave in and rinse off conditioners, agents for styling and treating hair, hair perming agents, relaxants, hair sprays and lacquers, permanent hair dyeing systems, semi-permanent hair dyeing systems, temporary hair dyeing systems, hair bleaching agents, lipsticks, nail varnishes, eye shadows, mascaras, dry and moist make-up, rouge, powders, depilatory agents, sun care and after sun products.

28. A method for the antimicrobial treatment of mammalian keratin-containing fibers, wherein said method comprises contacting said fibers with an effective amount of a personal care composition or formulation comprising one or more cationic nanoparticles of formula (I) according to claim 1.

29. A method for the antimicrobial treatment of mammalian skin, wherein said method comprises contacting said skin with an effective amount of a personal care composition or formulation comprising one or more cationic nanoparticles of formula (I) according to claim 1.

30. A method for the manufacture of an antimicrobial personal care composition or formulation, wherein said method comprises incorporating into said personal care composition or formulation an effective antimicrobial amount of one or more cationic nanoparticles of formula (I) according to claim 1.

* * * * *